United States Patent [19]

Morimoto et al.

[11] Patent Number: 5,545,608
[45] Date of Patent: Aug. 13, 1996

[54] PYRAZOLE-GLYCOLIC ACID AMIDE DERIVATIVES AS HERBICIDES

[75] Inventors: Katsushi Morimoto; Masatoshi Ohnari, both of Funabashi; Tsutomu Nawamaki, Minamisaitama-gun; Shigeomi Watanabe, Minamisaitama-gun; Kimihiro Ishikawa, Minamisaitama-gun, all of Japan

[73] Assignee: Nissan Chemical Industries, Ltd., Tokyo, Japan

[21] Appl. No.: 211,988

[22] PCT Filed: Nov. 12, 1992

[86] PCT No.: PCT/JP92/01476

§ 371 Date: Apr. 25, 1994

§ 102(e) Date: Apr. 25, 1994

[87] PCT Pub. No.: WO93/10099

PCT Pub. Date: May 27, 1993

[30] Foreign Application Priority Data

Nov. 12, 1991 [JP] Japan .................... 3-295910
Mar. 17, 1992 [JP] Japan .................... 4-060078
Jun. 12, 1992 [JP] Japan .................... 4-153323
Oct. 19, 1992 [JP] Japan .................... 4-279929

[51] Int. Cl.$^6$ .................... A01N 43/56; C07D 231/22; C07D 401/12; C07D 403/12
[52] U.S. Cl. .................... 504/282; 504/209; 504/219; 504/220; 504/249; 504/253; 540/450; 540/603; 546/187; 546/189; 546/265; 548/364.1; 548/366.1; 548/366.7; 548/375.1; 548/377.1

[58] Field of Search .................... 504/209, 219, 504/220, 249, 250, 253, 282; 540/450, 603; 546/256, 265, 279, 187, 189; 548/364.1, 365.1, 366.1, 366.7, 375.1, 377.1

[56] References Cited

FOREIGN PATENT DOCUMENTS

| | | |
|---|---|---|
| 0638555 | 2/1995 | European Pat. Off. . |
| 54-154762 | 12/1979 | Japan . |
| 55-147267 | 11/1980 | Japan . |
| 56-86175 | 7/1981 | Japan . |
| 63-35563 | 2/1988 | Japan . |
| 63-152367 | 6/1988 | Japan . |
| 0185965 | 8/1988 | Japan . |
| 63-185965 | 8/1988 | Japan . |
| 63-233977 | 9/1988 | Japan . |

*Primary Examiner*—Yogendra N. Gupta
*Attorney, Agent, or Firm*—Oliff & Berridge

[57] ABSTRACT

Pyrazole-glycolic acid amides of the following formula (1) (in which $R^1$ to $R^5$ each represent a hydrogen atom or a substituent having a broad definition), and herbicides containing them. The compounds have a high herbicidal effect against paddy weeds, especially *Echinochloa crus-galli*, while highly safe for paddy rice plants.

3 Claims, No Drawings

PYRAZOLE-GLYCOLIC ACID AMIDE DERIVATIVES AS HERBICIDES

This application is 371 of PCT/JP92/01476 filed on Nov. 12, 1995.

TECHNICAL FIELD

The present invention relates to novel pyrazole-glycolic acid amide derivatives and to herbicides containing them as the active ingredients.

BACKGROUND ART

At present, a lot of herbicides have been put to practical use as those applicable to paddy fields, and they are popularly used as single products or combination products.

Herbicides may be applied to various kinds of paddy weeds. A lot of herbicides effective against annual broad-leaved weeds are known, and herbicides effective against perennial weeds are increasing in these several years.

However, since *Echinochloa crus-galli*, which is one serious paddy weed and which grows mostly in large areas of paddy fields, belongs to the same family of Gramineae as a paddy rice plant belongs to, herbicides which are effective against only, *Echinochloa crus-galli*, especially those that have grown tall, without injuring paddy rice plants at all are not almost known.

As the prior art relating to compounds which are similar to the compounds of the present invention with respect to their chemical structures, compounds having a glycolic acid amide moiety bonded to the 2-position of a benzothiazole ring have been disclosed in JP-A 54-154762, compounds having the same moiety bonded to a 5-membered aromatic mono-cyclic ring containing an oxygen atom or a sulfur atom along with from 1 to 3 nitrogen atoms have been disclosed in JP-A 55-147267, compounds having the same moiety bonded to the 5-position of a tetrazole ring have been disclosed in JP-A 56-86175, and compounds having the same moiety bonded to the 5-position of an isoxazole ring have been disclosed in JP-A 63-152367. However, compounds having a glycolic acid amide moiety bonded to a pyrazole ring, such as those of the present invention, are not known at all up to the present and are novel compounds.

DESCRIPTION OF THE INVENTION

We, the present inventors have continued assiduous studies for many years so as to develop herbicides that are selectively effective against only harmful weeds without injuring important crop plants, while having investigated a lot of compounds with respect to their herbicidal activity so as to create herbicidal compounds which have a higher herbicidal activity and a broader selectivity in the activity. As a result, we have found that pyrazole-glycolic acid amide derivatives of the following formula (1) (hereinafter referred to as compounds of the present invention) have a high herbicidal activity against *Echinochloa crus-galli* and other paddy weeds, while having a high safety for paddy rice plants, and that the derivatives are effective even when a small amount of them is used. On the basis of these findings, we have completed the present invention.

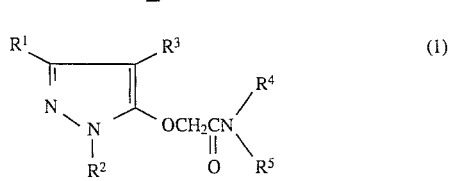

wherein $R^1$ represents a hydrogen atom, a $C_{1-6}$ alkyl group, a $C_{3-6}$ cycloalkyl group, a $C_{2-4}$ alkenyl group, a $C_{2-4}$ alkynyl group, a $C_{3-6}$ cycloalkyl-substituted $C_{1-2}$ alkyl group, a $C_{1-4}$ haloalkyl group, a di-$C_{1-4}$ alkylamino-$C_{1-4}$ alkyl group, a $C_{1-4}$ alkoxy-$C_{1-4}$ alkyl group, a $C_{1-4}$ alkylthio-$C_{1-4}$ alkyl group, a $C_{1-4}$ alkylsulfinyl-$C_{1-4}$ alkyl group, a $C_{1-4}$ alkylsulfonyl-$C_{1-4}$ alkyl group, a phenyl-substituted $C_{1-4}$ alkyl group, a phenyl group (optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a $C_{1-4}$ alkoxy group, a $C_{1-4}$ haloalkoxy group, a benzyloxy group, a $C_{1-4}$ alkylthio group, a benzylthio group, a $C_{1-4}$ alkylsulfinyl group, a $C_{1-4}$ alkylsulfonyl group, a di-$C_{1-4}$ alkylsulfamoyl group, a cyano group, a halogen atom, a di-$C_{1-4}$ alkylamino group or a nitro group;

$R^2$ represents a hydrogen atom, a $C_{1-6}$ alkyl group, a $C_{3-6}$ cycloalkyl group, a $C_{2-4}$ alkenyl group, a $C_{2-4}$ alkynyl group, a $C_{3-6}$ cycloalkyl-substituted $C_{1-2}$ alkyl group, a $C_{1-4}$ haloalkyl group, a $C_{1-4}$ alkylcarbonyl-$C_{1-4}$ alkyl group, a $C_{1-4}$ alkoxycarbonyl-$C_{1-4}$ alkyl group, a di-$C_{1-4}$ alkylamino-$C_{1-4}$ alkyl group, a $C_{1-4}$ alkoxy-$C_{1-4}$ alkyl group, a $C_{1-4}$ alkoxy-$C_{1-4}$ alkoxy-$C_{1-4}$ alkyl group, a $C_{1-4}$ alkylthio-$C_{1-4}$ alkyl group, a $C_{1-4}$ alkylsulfinyl-$C_{1-4}$ alkyl group, a $C_{1-4}$ alkylsulfonyl-$C_{1-4}$ alkyl group, a phenyl-substituted $C_{1-4}$ alkyl group, a phenyl group (optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a naphthyl group, a pyridyl group (optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a $C_{1-4}$ alkylcarbonyl group, a $C_{1-4}$ alkylaminocarbonyl group, a di-$C_{1-4}$ alkylaminocarbonyl group, a $C_{1-4}$ alkoxycarbonyl group, a $C_{1-4}$ alkylsulfonyl group or a di-$C_{1-4}$ alkylsulfamoyl group;

$R^3$ represents a hydrogen atom, a $C_{1-6}$ alkyl group, a $C_{3-6}$ cycloalkyl group, a $C_{2-4}$ alkenyl group, a $C_{2-4}$ alkynyl group, a phenyl group (optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a cyano group, a halogen atom or a nitro group;

$R^4$ and $R^5$ independently represent a hydrogen atom, a $C_{1-6}$ alkyl group, a $C_{3-6}$ cycloalkyl group, a $C_{2-4}$ alkenyl group, a $C_{2-4}$ alkynyl group, a $C_{3-6}$ cycloalkyl-substituted $C_{1-2}$ alkyl group, a $C_{1-4}$ alkoxy-$C_{1-4}$ alkyl group, a phenyl-substituted $C_{1-4}$ alkyl group (in which the phenyl moiety may be optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a phenyl group (optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a pyridyl-substituted $C_{1-4}$ alkyl group (in which the pyridyl moiety may be optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a pyridyl group (optionally substituted by one or more substituents selected from a $C_{1-4}$ alkyl group, a $C_{1-4}$ haloalkyl group, a $C_{1-4}$ alkoxy group, a cyano group, a nitro group and a halogen atom), a naphthyl group, a naphthyl-substituted $C_{1-4}$ alkyl group, a $C_{1-4}$ alkoxy group (provided that both $R^4$ and $R^5$ must not be alkoxy groups), a cyano-$C_{1-4}$ alkyl group, a $C_{1-4}$ alkylcarbonyl group, a $C_{1-4}$ alkoxycarbonyl group, a $C_{1-4}$ alkoxycarbonyl-$C_{1-4}$ alkyl group or a $C_{1-4}$ alkylsulfonyl group; and $R^4$ and $R^5$ may form, along with the nitrogen atom to which they bond, a 3-membered to 9-membered ring; and the ring may have one or more oxygen atoms, sulfur atoms, nitrogen atoms, carbonyl groups, sulfonyl groups or unsaturated bonds, the ring may be substituted by a $C_{1-4}$ alkyl group, a $C_{1-4}$ alkoxy group, a hydroxyl group, a halogen atom, a $C_{1-4}$ haloalkyl group, a $C_{1-4}$ alkoxycarbonyl group, a phenyl group or a benzyl group, the ring may be crosslinked with a $C_{1-4}$ alkylene, and the ring may be condensed with a benzene ring.

Examples of the substituents $R^1$, $R^2$, $R^3$, $R^4$ and $R^5$ in the compounds of the present invention are mentioned hereunder, while the definitions of the abbreviated expressions used therein are mentioned below.

Me: methyl group
Et: ethyl group
Pr-n: normal propyl group
Pr-iso: isopropyl group
Bu-n: normal butyl group
Bu-iso: isobutyl group
Bu-sec: secondary butyl group
Bu-tert: tertiary butyl group
Pen-n: normal pentyl group
Hex-n: normal hexyl group
Pr-cyc: cyclopropyl group
Bu-cyc: cyclobutyl group
Pen-cycl: cylopentyl group
Hex-cyc: cyclohexyl group
Ph: phenyl group
Py: pyridyl group
Naph: naphthyl group Examples of the substituent $R_1$ in the compounds of the present invention:

H, Me, Bt, Pr-n, Pr-iso, Bu-n, Bu-iso, Bu-sec, Bu-tert, Pen-n, Hex-n, Hex-iso, Pr-cyc, Bu-cyc, Pen-cyc, Hex-cyc, $CH_2CH=CH_2$, $CH_2CH=CHMe$, $CH_2CH_2CH=CH_2$, $CH_2C\equiv CH$, $CH_2C\equiv CMe$, $CH_2Pr$-cyc, $CH_2Bu$-cyc, $CH_2Pen$-cyc, $CH_2Hex$-cyc, $CH_2CH_2Pr$-cyc, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2CF_2$, $Cl$ $CH_2CH_2CH_2$, $ClCH_2CH_2CH_2$, $CH_2NMe_2$, $CH_2NEt_2$, $CH_2N(Pr$-n$)_2$, $CH_2N(Pr$-iso$)_2$, $CH_2N(Bu$-n$)_2$, $CH_2CH_2CH_2CH_2NMe_2$, $CH_2OMe$, $CH_2OEt$, $CH_2OPr$-n, $CH_2OBu$-n, $CH_2OBu$-iso, $CH_2OBu$-sec, $CH_2OBu$-tert, $CH_2CH_2OMe$, $CH_2CH_2OEt$, $CH_2CH_2OPr$-n, $CH_2CH_2CH_2OMe$, $CH_2CH_2CH_2OEt$, $CH_2CH_2CH_2CH_2OMe$, $CH_2SMe$, $CH_2SEt$, $CH_2SPr$-n, $CH_2SBu$-n, $CH_2CH_2CH_2SMe$, $CH_2S(O)Me$, $CH_2S(O)Et$, $CH_2S(O)Pr$-n, $CH_2S(O)Bu$-n,, $CH_2CH_2CH_2CH_2S(O)Me$, $CH_2SO_2Me$, $CH_2SO_2Et$, $CH_2SO_2Pr$-n, $CH_2SO_2Bu$-n, $CH_2CH_2CH_2CH_2SO_2Me$, $CH_2Ph$, $CHMePh$, $CMe_2Ph$, Ph, 2-Cl-Ph, 3-Cl-Ph, 4-Cl-Ph, 2,4-Cl$_2$-Ph, 2-F-Ph, 3-F-Ph, 4-F-Ph, 2-F-4-Cl-Ph, 2-Br-Ph, 3-Br-Ph, 4-Br-Ph, 2-Me-Ph, 3-Me-Ph, 4-Me-Ph, 2,4-Me$_2$-Ph, 2,6-Me$_2$-Ph, 2-MeO-Ph, 3-MeO-Ph, 4-MeO-Ph, 2-CF$_3$-Ph, 3-CF$_3$-Ph 4-CF$_3$-Ph, 3,5-Cl$_2$-Ph, 2,6-Cl$_2$-Ph, 2,3-Cl$_2$-Ph, 2,4,6-Cl$_3$-Ph, 2,3,5-Cl$_3$-Ph, 2,3,4-Cl$_3$-Ph, 2-NO$_2$-Ph, 2-CN-Ph, OMe, OEt, OPr-n, OPr-iso, OBu-n, OBu-iso, OBu-tert, OCH$_2$F, OCBrF$_2$, OCHF$_2$, OCF$_3$, OCH$_2$CH$_2$Cl, OCH$_2$CH$_2$CH$_2$CHCl, OCH$_2$Ph, SMe, SEt, SPr-n, SPr-iso, SBu-n, SBu-iso, SBu-tert, SCH$_2$Ph, S(O)Me, S(O)Et, S(O)Pr-n, S(O)Pr-iso, S(O)Bu-n, SO$_2$Me, SO$_2$Et, SO$_2$Pr-n, SO$_2$Pr-iso, SO$_2$Bu-n, SO$_2$NMe$_2$, SO$_2$NEt$_2$, SO$_2$N(Pr-n)$_2$, SO$_2$N(Bu-n)$_2$, CN, F, Cl, Br, I, NMe$_2$, NEt$_2$, N(Pr-n)$_2$, N(Pr-iso)$_2$, N(Bu-n)$_2$, NO$_2$ Examples of the substituent $R^2$ in the compounds of the present invention:

H, Me, Bt, Pr-n, Pt-iso, Bu-n, BU-iso, Bu-sec, Bu-tert, Pen-n, Hex-n, Pr-cyc, Bu-cyc, Pen-cyc, Hex-cyc, $CH_2CH|CH_2$, $CH_2CH|CHMe$, $CH_2CH_2CH|CH_2$, $CH_2C\equiv CH_2C\equiv CMe$, $CH_2Pr$-cyc, $CH_2Bu$-cyc, $CH_2Pen$-cyc, $CH_2Hex$-cyc, $CH_2CH_2$ Pr-cyc, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $CF_3CF_2CF_2$, $ClCH_2CH_2CH_2$, $ClCH_2CH_2CH_2$, $CH_2$, $CH_2COMe$, $CH_2COBt$, $CH_2COPr$-n, $CH_2COPr$-iso, $CH_2COBu$-n, $CHMeCOMe$, $CHMeCOBt$, $CHMeCOPr$-n, $CH_2CH_2CH_2COMe$, $CH_2CO_2Me$, $CH_2CO_2Bt$, $CH_2CO_2Pr$-n, $CH_2CO_2Pr$-iso, $CH_2CO_2Bu$-n, $CHMeCO_2Me$, $CHMeCO_2Bt$, $CHMeCO_2Pr$-n, $CH_2CH_2CH_2CO_2$, $CH_2NMe_2$, $CH_2NBt_2$, $CH_2N(Pr$-n$)_2$, $CH_2N(Pr$-iso$)_2$, $CH_2N(Bu$-n$)_2$, $CH_2CH_2CH_2CH_2NMe_2$, $CH_2OMe$, $CH_2OBt$, $CH_2OPr$-n, $CH_2OBu$-n, $CH_2OBu$-iso, $CH_2OBu$-sec, $CH_2OBu$-tert, $CH_2CH_2OMe$, $CH_2CH_2OBt$, $CH_2CH_2OPr$-n, $CH_2CH_2CH_2OMe$, $CH_2CH_2CH_2OBt$, $CH_2CH_2CH_2CH_2OMe$, $CH_2OCH_2CH_2OMe$, $CH_2OCH_2CH_2OBt$, $CH_2SBt$, $CH_2SPr$-n, $CH_2SBu$-n, $CH_2CH_2CH_2CH_2SMe$, $CH_2S(O)Me$, $CH_2S(O)Bt$, $CH_2S(O)Pr$-n, $CH_2S(O)Bu$-n, $CH_2CH_2CH_2CH_2S(O)Me$, $CH_2SO_2Me$, $CH_2SO_2Bt$, $CH_2SO_2Pr$-n, $CH_2SO_2Bu$-n, $CH_2CH_2CH_2CH_2SO_2Me$, $CH_2Ph$, $CHMePh$, $CMe_2Ph$, Ph, 2-Cl-Ph, 3-Cl-Ph, 4Cl-Ph, 2,4-Cl$_2$-Ph, 2-F-Ph, 3-F-Ph, 4-F-Ph, 2-F-4-Cl-Ph, 2-Br-Ph, 3-Br-Ph, 4-Br-Ph, 2-Me-Ph, 3-Me-Ph, 4-Me-Ph, 2,4-Me$_2$Ph, 2,6-Me$_2$-Ph, 2-MeO-Ph, 3-MeO-Ph, 4-MeO-Ph, 2-CF$_3$-Ph, 3CF$_3$-Ph, 4-CF$_3$-Ph, 3,5-Cl$_2$-Ph, 2,6-Cl$_2$-Ph, 2,3-Cl$_2$-Ph, 2,4,6-Cl$_3$-Ph, 2,3,5-Cl$_3$Ph, 2,3,4-Cl$_3$Ph, 2-Cl-4-CF$_3$-Ph, 2,6-Cl$_2$-4-CF$_3$-Ph, 2-NO$_2$-Ph, 2-CN-Ph, 3-CN-Ph, 4-CN-Ph, 1-Naph, 2-Naph, COMe, COBt, COPr-n, COPr-iso, COBu-n, CONHMe, CONHBt, CONHPr-n, CONHPr-iso, CONHBu-n, CONMe$_2$, CONBt$_2$, CON(Pr-n)$_2$, CON(Pr-iso)$_2$, CON(Bu-n)$_2$, CO$_2$Me, CO$_2$Bt, CO$_2$Pr-n, CO$_2$Pr-iso, CO$_2$Bu-n, SO$_2$Me, SO$_2$Bt, SO$_2$Pr-n, SO$_2$Pr-iso, SO$_2$Bu-n, SO$_2$NMe$_2$, SO$_2$NBt$_2$, SO$_2$N(Pr-n)$_2$, SO$_2$N(Bu-n)$_2$, 2,5-Cl$_2$-Ph, 3,4-Cl$_2$-Ph, 2,4-(NO$_2$)$_2$-Ph, 3-NO$_2$-Ph, 4-NO$_2$-Ph, 2-Py, 3-Py, 4-Py, 3-Cl-2-Py, 4Cl-2-Py, 5Cl-2-Py, 6-Cl-2-Py, 3-F-2-Py, 4-F-2-Py, 5-F-2-Py, 6F-2-Py, 3-Br-2-Py, 4-Br-2-Py, 5-Br-2-Py, 6-Br-2-Py, 3-CF$_3$-2Py, 4CF$_3$-2-Py, 5-CF$_3$-2-Py, 6-CF$_2$-Py, 3-Cl-5-CF$_3$-2Py, 3Me-2-Py, 4Me-2-Py, 5-Me-2-Py, 6-Me-2-Py, 3-NO$_2$2-Py, 4-NO$_2$-2-Py, 5-NO$_2$-Py, 6-NO$_2$-2-Py, 3-Py, 4-Py Examples of the substituent $R^3$ in the compounds of the present invention:

CN, F, Cl, Br, I, NO$_2$, H, Me, Bt, Pr-n, Pr-iso, Bu-n, Bu-iso, Bu-sec, Bu-tert, Pen-n, Hex-n, Hex-iso, Pr-cyc, Bu-cyc, Pen-cyc, Hex-cyc, $CH_2CH|CH_2$, $CH_2CH=CHMe$, $CH_2CH_2CH=CH_2$, $CH_2C\equiv CH$, $CH_2C\equiv CMe$, Ph, 2-Cl-Ph, 3-Cl-Ph, 4-Ph, 2,4-Cl$_2$-Ph, 2-F-Ph, 3-F-Ph, 4-F-Ph, 2F-4-Cl-Ph, 2-Br-Ph, 3-Br-Ph, 4-Br-Ph, 2-Me-Ph, 3-Me-Ph, 4-Me-Ph, 2,4-Me$_2$-Ph, 2,6-Me$_2$-Ph, 2-MeO-Ph, 3MeO-Ph, 4MeO-Ph, 2-CF$_8$-Ph, 3-CF$_8$-Ph, 4-CF$_8$-Ph, 3,5-Cl$_2$-Ph, 2,6-Cl$_2$-Ph, 2,3-Cl$_2$-Ph, 2,4,6-Cl$_8$-Ph, 2,3,5-Cl$_3$ 2,3,4-Cl$_3$-Ph, 2-NO$_2$-Ph, 2-CN-Ph Examples of the substituents $R^4$ and $R^5$ in the compounds of the present invention: H, Me, Bt, Pr-n, Pr-iso, Bu-n, Bu-iso, Bu-sec, Bu-tert, CHMeCHMe$_2$, Pen-n, Hex-n, Hex-iso, Pr-cyc, Bu-cyc Pen-cyc, Hex-cyc, $CH_2Pr$-cyc, $CH_2Bu$-cyc, $CH_2Hex$-cyc, $CH_2CH_2Pr$-cyc, $CH_2CH=CH_2$, CH₂CHlCHMe, CH₂CH₂CH=CH₂, CH₂C≡CH, CH₂C≡CMe, CH₂Ome CH₂OBt, CH₂OPr-n, CH₂OBu-n, CH₂OBu-iso, CH₂OBu-sec, CH₂OBu-tert, CH₂CH₂Ome CH₂CH₂OBt, CH₂CH₂OPr-n, CH₂CH₂CH₂OMe, CH₂CH₂CH₂OBt, CH₂CH₂CH₂CH₂OMe, Ph, 2Cl-Ph, 3-Cl-Ph, 4-Cl-Ph, 2,4-Cl₂-Ph, 3,5-Cl₂-Ph, 2,6-Cl₂-Ph, 2,3-Cl₂-Ph, 2,5-Cl₂-Ph, 2-F-Ph, 3-F-Ph, 4-F-Ph, 2-F-4-Cl-Ph, 2-Br-Ph, 3-Br-Ph, 4-Br-Ph, 2-Me-Ph, 3-Me-Ph, 4-Me-Ph, 2,4-Me₂Ph, 3,5-Me₂-Ph, 2,6-Me₂-Ph, 2,3-Me₂Ph, 2,5Me₂-Ph, 2-MeO-Ph, 3-MeO-Ph, 4-MeO-Ph, 2-CF₈-Ph, 3-CF₈-Ph, 4-CF₈-Ph, 2,4,6-CL₈-Ph, 2,3,5-Cl₈-Ph, 2,3,4-Cl₈Ph, 2-NO₂-Ph, 2-CN-Ph, CH₂-Ph, OMe, OBt, OPr-n, OPr-iso, OBu-n, OBu-iso, OBu-tert, SO₂Bt, SO₂Pr-n, SO₂Pr-iso, SO₂Bu-n, COMe, COBt, COPr-iso, COBu-n, CO₂Me, CO₂Bt, CO₂Pr-n, CO₂Pr-iso, CO₂Bu-n, CH₂CO₂Me, CH₂CO₂Bt, CH₂CO₂Pr-n, CH₂CO₂Bu-n, CHMeCO₂Me, CHMeCO₂Bt, CH₂CH₂CO₂Me, CH₂CH₂CH₂CO₂Me, CH₂CH₂CH₂CH₂CO₂Me, CH(Pr-iso)CO₂Me, CH(Bu-sec)CO₂Me, CH(Bu-iso)CO₂Me, CH(CH₂Ph)CO₂Me, CH₂CH₂CN, 1 Naph, 2-Naph, CH₂-1-Naph, CH₂-2-Naph, CH₂Ph, CHMePh, CMe₂Ph, CH₂-Cl-Ph, CH₂-3-Cl-Ph, CH₂-4-Cl-Ph, 2-Py, 6-MeO-2-Py, 6-Cl-2-Py, 6F-2-2-Py, 5-CF₈-2-Py, 3-Cl-5-CF₈-2-Py, 3-Py, 4-Py, CH₂-5-Cl-2-Py, CH₂-6-Cl-3-Py Examples of saturated 5-membered to 7-membered rings to be formed by the substituents $R^4$ and $R^5$ along with the nitrogen atom to which they bond in the compounds of the present invention:

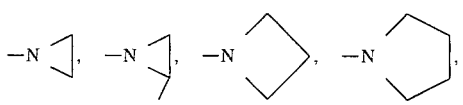

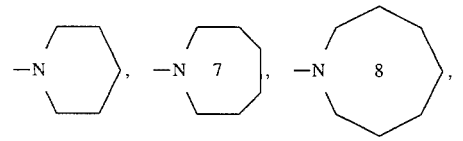

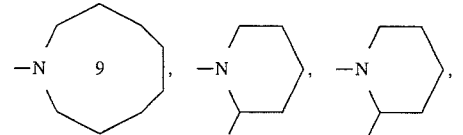

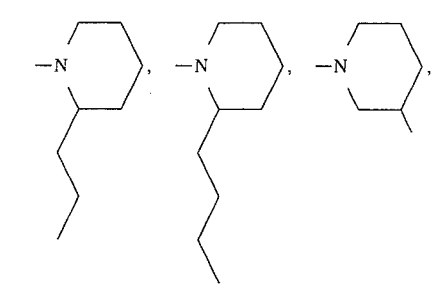

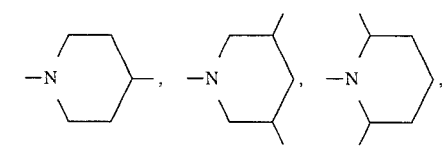

-continued

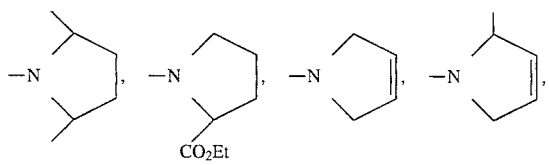

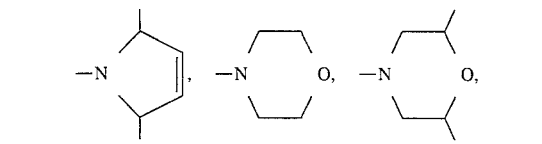

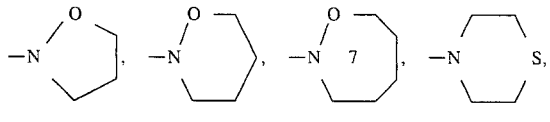

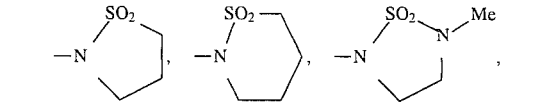

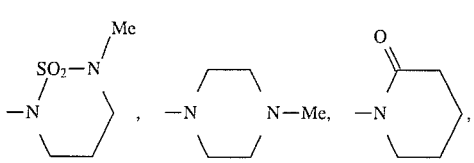

-continued

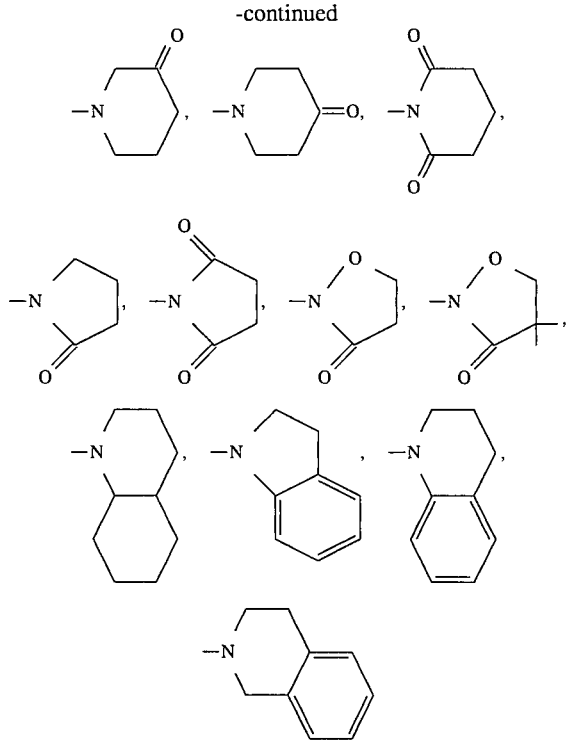

The compounds of the present invention may be produced easily in accordance with anyone of the following reaction schemes 1 to 4.

Reaction Scheme 1:

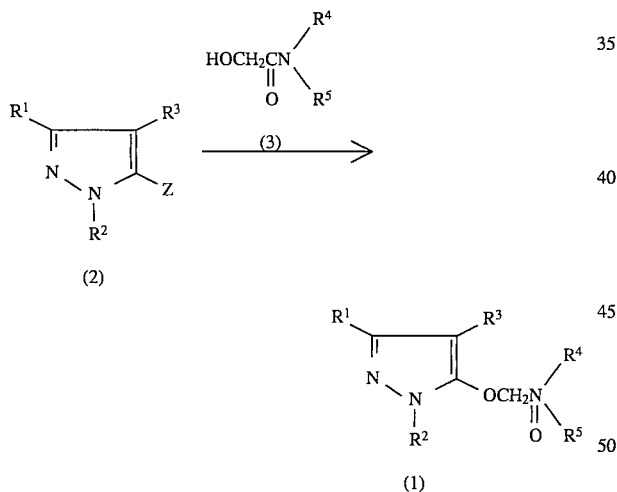

wherein $R^1$, $R^2$, $R^3$, $R^4$ and $R^5$ have the same definitions as those mentioned above, and Z represents a halogen atom.

Precisely, a 5-halogenopyrazole (2) is reacted with a glycolic acid amide (3) in the presence of a base to produce the compound (1) of the present invention. As the base, usable are inorganic bases such as sodium hydroxide, potassium hydroxide, potassium carbonate, sodium hydride, etc.; or organic bases such as pyridine, triethylamine, DBU, etc. This reaction may progress even in the absence of a solvent but, if desired, may be conducted in the presence of a solvent. The solvent usable in the reaction is not specifically defined, provided that it is inert to the reaction. As the usable solvents, for example, mentioned are aliphatic or aromatic hydrocarbons such as hexane, cyclohexane, benzene, toluene, etc.; ethers such as diethyl ether, diisopropyl ether, dioxane, tetrahydrofuran, etc.; ketones such as acetone, methyl ethyl ketone, methyl isobutyl ketone, etc.; nitriles such as acetonitrile, propionitrile, etc.; acid amides such as dimethylformamide, dimethylacetamide, etc.; sulfones such as dimethylsulfoxide, sulforane, etc.; and organic bases such as pyridine, etc. The reaction temperature may be freely selected from the range between –50° C. and 150° C. but is preferably within the range between 0° C. and 60° C.

Reaction Scheme 2:

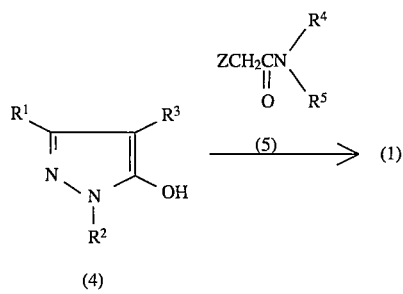

wherein $R^1$, $R^2$, $R^3$, $R^4$, $R^5$ and Z have the same definitions as those mentioned above.

Precisely, a 5-hydroxypyrazole (4) is reacted with a halogenoacetamide (5) in the presence of a base to produce the compound (1) of the present invention. As the base and the solvent, those mentioned for the reaction scheme 1 shall be referred to. The reaction temperature may be freely selected from the range between –50° C. and 150° C. but is preferably within the range between 0° C. and 100° C.

Reaction Scheme 3:

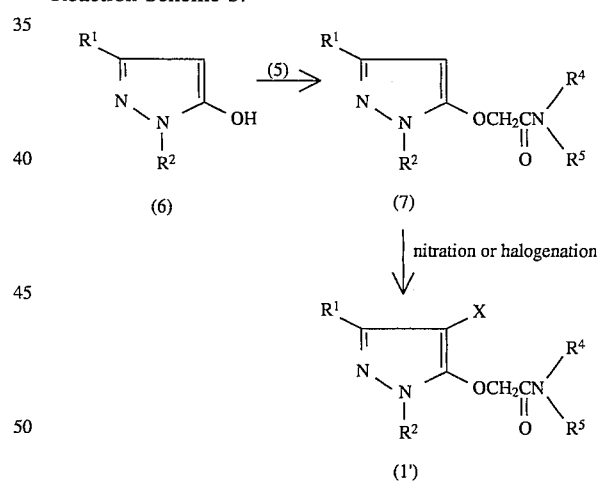

wherein $R^1$, $R^2$, $R^3$, $R^4$ and $R^5$ have the same definitions as those mentioned above, and X represents a nitro group or a halogen atom.

Precisely, a 5-hydroxypyrazole (6) is reacted with a halogenoacetamide (5) in the presence of a base to give a pyrazole-glycolic acid amide (7). As the base, the solvent and the reaction temperature, those mentioned for the reaction scheme 1 shall be referred to. The amide (7) is then treated with a nitrating agent such as a mixed acid or the like or with an electrophilic halogenating agent such as chlorine, bromine, sulfuryl chloride, N-chlorosuccinimide, N-bromosuccinimide, etc., to produce the compound (1') of the present invention.

Reaction Scheme 4:

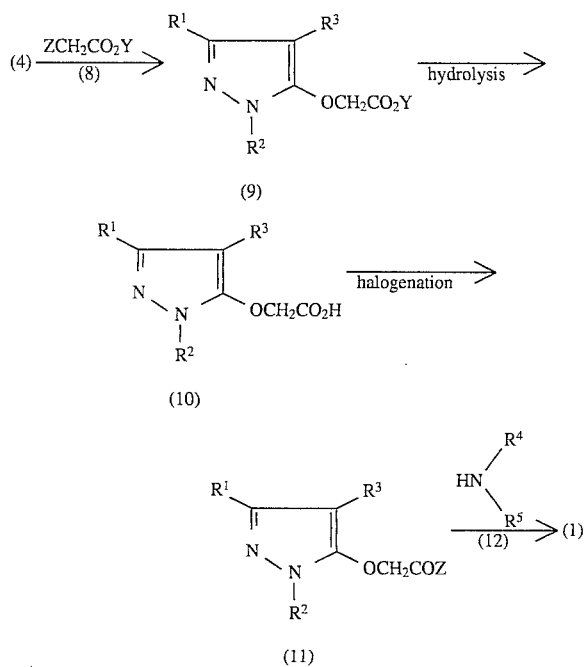

wherein $R^1$, $R^2$, $R^3$, $R^4$, $R^5$ and Z have the same definitions as those mentioned above, and Y represents a $C_{1-6}$ alkyl group or a phenyl group.

Precisely, a 5-hydroxypyrazole (4) is reacted with a halogenoacetate (8) in the presence of a base to give a pyrazole-glycolate (9). As the base, the solvent and the reaction temperature, those mentioned for the reaction scheme 1 shall be referred to. The ester (9) is then hydrolyzed and halogenated to give an acid chloride (11), which is reacted with an amine (12) to produce the compound (1) of the present invention.

Regarding the staring materials to be used in the above-mentioned reactions, 5-chloro-4-nitropyrazoles (2, Z=Cl) may be produced with reference to U.S. Pat. No. 3,282,954 (1966), etc.; 5-bromo-4-nitropyrazoles (2, Z=Br) may b produced with reference to Journal of Organic Chemistry Vol. 51, page 4656 (1986), etc.; and 5-hydroxy-4-nitropyrazoles (4) may be produced with reference to Chemiche Berichte, Vol. 74, page 1420 (1941), etc.

Examples of producing the compounds of the present invention are mentioned hereunder, which, however, are not intended to restrict the scope of the present invention.

Example 1:

(1) Production of 3,5-dichloro-1-methylpyrazole:

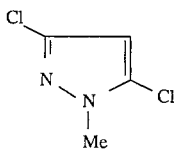

113 g (0.58 mol) of 3,5-dichloro-1-methylpyrazole- 4-carboxylic acid were heated at 300° C. and distilled to give 51 g of a crude oil, which were dissolved in 200 ml of chloroform and washed with water. After removal of the solvent, 44 g of the intended product were obtained by distillation. This had a boiling point of 172° to 173° C.

(2) Production of 3,5-dichloro-1-methyl-4-nitropyrazole:

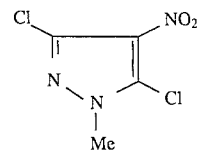

A solution of 8.5 g (56 mmol) of 3,5-dichloro-1-methylpyrazole in acetic anhydride (15 ml) was added dropwise to a mixed acid comprising 20 ml of concentrated sulfuric acid and 6 g of fuming nitric acid, at 20° C. or lower. After stirred for 48 hours at room temperature, this was poured into 300 ml of water with ice, whereupon the crystals thus precipitated were taken out by filtration, washed with water and dried to obtain 5.68 g of the intended product. This .had a melting point of 84° to 88° C.

(3) Production of N-methyl-N-phenyl-2-(3-chloro-1-methyl- 4-nitropyrazol-5-yloxy)acetamide:

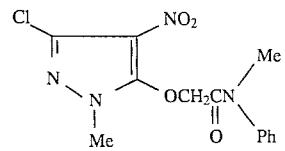

No. 1

0.63 g (3.2 mmol) of 3,5-dichloro-1-methyl-4-nitropyrazole and 0.53 g (3.2 mmol) of N-methyl-N-phenylglycolic acid amide were dissolved in 5 ml of DMF, and 0.18 g (3.2 mmol) of powdery potassium hydroxide were added thereto. After this was stirred for 0.5 hours at room temperature, 20 ml of water were added thereto. This was extracted two times each with 20 ml of benzene, the resulting extract was washed with water and dried with anhydrous sodium sulfate. Then, the solvent was removed by distillation. A small amount of diisopropyl ether was added to the resulting residue, and the crystals thus precipitated were taken out by filtration and dried to obtain 0.7 g of the intended product. This had a melting point of 104° to 105° C.

Example 2:

(1) Production of 3-trifluoromethyl-1-methyl-5-hydroxy-4-nitropyrazole:

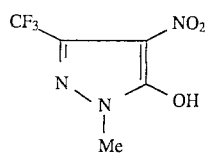

10 g (60 mmol) of 3-trifluoromethyl-1-methyl-5-hydroxypyrazole were dissolved in 30 ml of concentrated sulfuric acid, and 7 ml of 60% nitric acid were dropwise added thereto at 10° C. or lower. After stirred for 2 hours at room temperature, this was poured into 300 ml of water with ice, whereupon the crystals thus precipitated were taken out by filtration, washed with water and dried. The thus-obtained crystals were washed with a mixture of diisopropyl ether and diethyl ether and dried to obtain 5.5 g of the intended pure product. This had a melting point of 93° to 94° C.

(2) Production of N-methyl-N-phenyl-2-(3-trifluoromethyl-1-methyl-4-nitropyrazol-5-yloxy)acetamide:

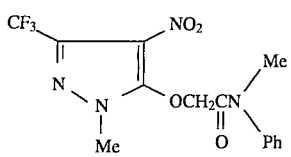

1.0 g (4.7 mmol) of 3-trifluoromethyl-1-methyl- 5-hydroxy-4-nitropyrazole and 0.95 g (5.2 mmol) of N-methyl-N-phenylchloroacetamide were dissolved in 10 ml of DMF, and 0.29 g (5.2 mmol) of powdery potassium hydroxide were added thereto and stirred for 5 hours at 80° C. After this was cooled, 30 ml of water were added thereto. Then, this was extracted two times each with 30 ml of benzene. The resulting extract was washed with water and de-watered with anhydrous sodium sulfate. The solvent was removed by distillation, and an oily residue was obtained. The residue was purified by preparative high performance liquid chromatography to obtain 0.04 g of the intended product. This was oily.

Example 3:
Production of 2-[4-chloro-1-(2,5-dichlorophenyl)- 3-trifluoromethylpyrazol-5-yloxy)acetopiperidide:

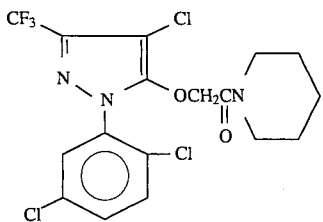

No. 122

0.8 g (2.4 mmol) of 4-chloro-1-( 2,5-dichlorophenyl)-3-trifluoromethyl-5-hydroxypyrazole and 0.56 g (2.2 mmol) of chloroacetopiperidide were dissolved in 4 ml of DMF, and 0.5 g (3.6 mmol) of potassium carbonate were added thereto and stirred for 4 hours at 80° C. After cooled, 50 ml of water were added thereto. Then, this was extracted two times each with 50 ml of diethyl ether. The resulting extract was washed with water and a saturated saline solution in order and then de-watered with anhydrous magnesium sulfate. The solvent was then removed by distillation. The residue was purified by silica gel column chromatography (using chloroform as the eluent) to obtain 0.42 g of the intended product. This had a melting point of 61° to 62° C.

Example 4:
(1) Production of 2-(3-trifluoromethylpyrazol-5-yloxy)acetopiperidide:

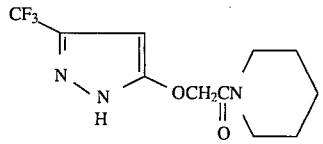

No. 163

6.0 g (40 mmol) of 3-trifluoromethyl-5-hydroxypyrazole and 6.4 g (39 mmol) of chloroaceto-piperidide were dissolved in 40 ml of DMF, and 8.2 g (59 mmol) of potassium carbonate were added thereto and stirred for 4 hours at room temperature. After stirred for further 2 hours at 50° C., this was cooled. 200 ml of water were added thereto, and this was extracted two times each with 200 ml of ethyl acetate. The resulting extract was washed with a saturated saline solution and de-watered with anhydrous magnesium sulfate. Then, the solvent was removed by distillation. Diethyl ether was added to the residue, whereupon the crystals thus precipitated were taken out by filtration and dried to obtain 3.6 g of the intended product. This had a melting point of 154° to 156° C.

(2) Production of 2-(3-trifluoromethyl- 1-propargylpyrazol-5-yloxy)acetopiperidide:

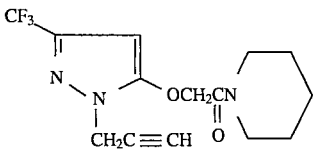

0.8 g (2.9 mmol) of 2-(3-trifluoromethylpyrazol-5-yloxy-)acetopiperidide and 0.34 g (2.9 mmol) of propargyl bromide were dissolved in 4 ml of DMF, and 0.6 g (4.3 mmol) of potassium carbonate were added thereto and stirred for 18 hours at room temperature. 50 ml of water were added thereto, and this was extracted two times each with 50 ml of diethyl ether.

The resulting extract was washed with water and a saturated saline solution in order and de-watered with anhydrous magnesium sulfate. Then, the solvent was removed by distillation. The residue was purified by silica gel column chromatography (using chloroform as the eluent) to obtain 0.75 g of a mixture comprising the intended product and its isomer of 2-(5-trifluoromethyl- 1-propargylpyrazol-3-yloxy) acetopiperidide.

In the next step, the mixture was used directly as it was.
(3) Production of 2-(4-chloro-3-trifluoromethyl- 1-propargylpyrazol-5-yloxy)acetopiperidide:

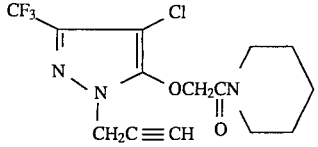

No. 148

0.75 g (2.4 mmol) of the mixture of isomers, that had been obtained in (2), were dissolved in 4 ml of chloroform, and 0.19 g (1.4 mmol) of sulfuryl chloride were added dropwise thereto at 0° C. After this was stirred for 2 hours at 0° C., 20 ml of water with ice were added thereto. This was then extracted two times each with 20 ml of chloroform. The resulting extract was washed with an aqueous 10% sodium hydrogencarbonate solution and a saturated saline solution in order and de-watered with anhydrous magnesium sulfate. Then, the solvent was removed by distillation. The residue was purified by thin layer silica gel chromatography (using ethyl acetate/n-hexane=1/1 as the developer) to obtain 0.35 g of the intended product. This had a melting point of 78° to 79° C. The 2-(5-trifluoromethyl- 1-propargylpyrazol-3-yloxy)acetopiperidide contained in the starting material was unreacted and recovered as an oily substance of 0.35 g.

Example 5:
(1) Production of ethyl 2-(4-chloro-3-trifluoromethyl-1-phenylpyrazol-5-yloxy)acetate:

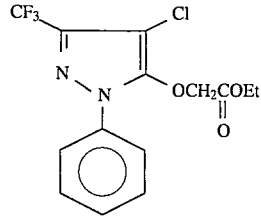

28 g (107 mmol) of 4-chloro-3-trifluoromethyl- 5-hydroxy-1-phenylpyrazole and 19.5 g (117 mmol) of ethyl bromoacetate were dissolved in 150 ml of acetonitrile, and 28 g (203 mmol) of potassium carbonate were added thereto and refluxed for one hour.

After cooled, the solid was filtrated out and the solvent was removed by distillation. 150 ml of chloroform were added to the residue, which was washed with water and de-watered with anhydrous sodium sulfate. Then, the solvent was removed by distillation, and 37 g of the intended product were obtained. This was oily.

(2) Production of 2-(4-chloro-3-trifluoromethyl- 1-phenylpyrazol-5-yloxy)acetic acid:

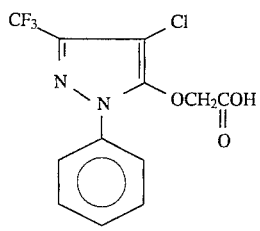

37 g (106 mmol) of ethyl 2-(4-chloro- 3-trifluoromethyl-1-phenylpyrazol-5-yloxy)acetate were dissolved in 100 ml of ethanol, and 40 ml of an aqueous solution of 8.5 g (213 mmol) of sodium hydroxide were added thereto. After this was stirred for one hour at room temperature, the solvent was removed by distillation and the residue was dissolved in 300 ml of water. The resulting aqueous solution was washed with 100 ml of benzene and then made acidic (pH 1) with concentrated hydrochloric acid. This was extracted three times each with 100 ml of chloroform, and the resulting extract was washed with water and de-watered with anhydrous sodium sulfate. Then, the solvent was removed by distillation and 33 g of the intended product were obtained. This had a melting point: of 93° to 96° C.

(3) Production of 2-(4-chloro-3-trifluoromethyl- 1-phenylpyrazol-5-yloxy)acetyl chloride:

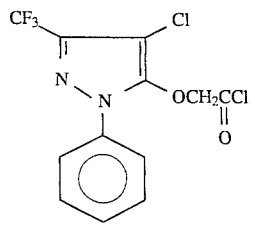

80 ml of thionyl chloride were added to 23 g (72 mmol) of 2-(4-chloro-3-trifluoromethyl-1-phenylpyrazol-5-yloxy)-acetic acid and heated under reflux for 1.5 hours. The thionyl chloride was removed by distillation under reduced pressure, and 24 g of the intended product were obtained. This was oily.

(4) Production of N,N-diallyl-2-(4-chloro- 3-trifluoromethyl-1-phenylpyrazol-5-yloxy) acetamide:

No. 92

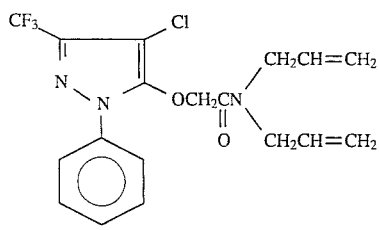

0.8 g (8.2 mmol) of diallylamine were dissolved in 10 ml of THF and 1.3 g (3.8 mmol) of 2-(4-chloro- 3-trifluoromethyl-1-phenylpyrazol-5-yloxy)acetyl chloride were added thereto and stirred for one hour at room temperature. The reaction mixture was extracted by adding 50 ml of water, 100 ml of chloroform and several drops of concentrated hydrochloric acid thereto. The chloroform layer was washed with water and de-watered with anhydrous sodium sulfate. Then, the solvent was removed by distillation. The residue was purified by silica gel column chromatography (using chloroform as the eluent) to obtain 1.3 g of the intended product. This was oily.

By the same methods as those of the above-mentioned examples, the compounds mentioned in Table 1 below were produced, where the structural formulae and the physical data of the compounds produced are shown along with those of the compounds produced in the above-mentioned examples. The definitions of the symbols used in Table 1 are mentioned below.

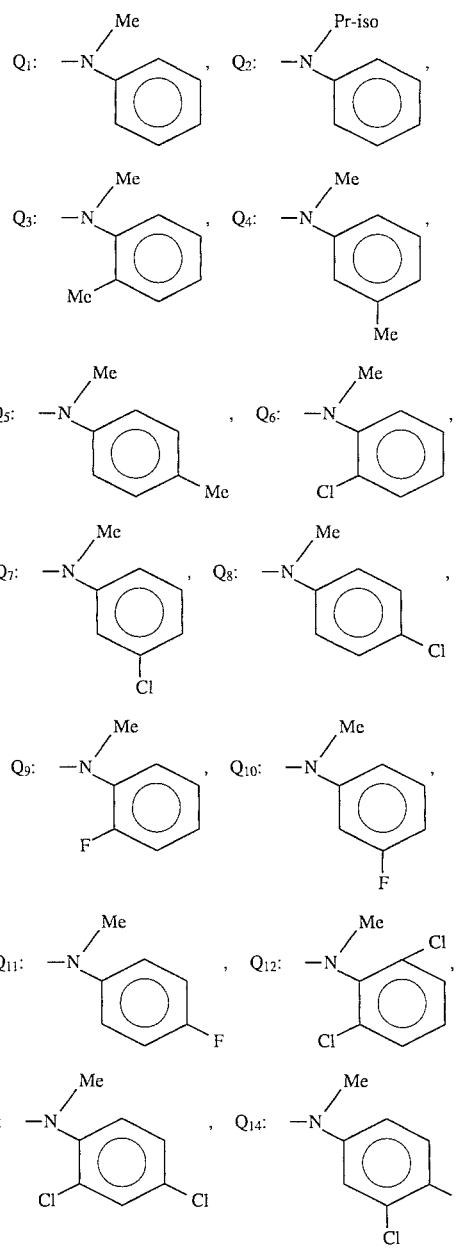

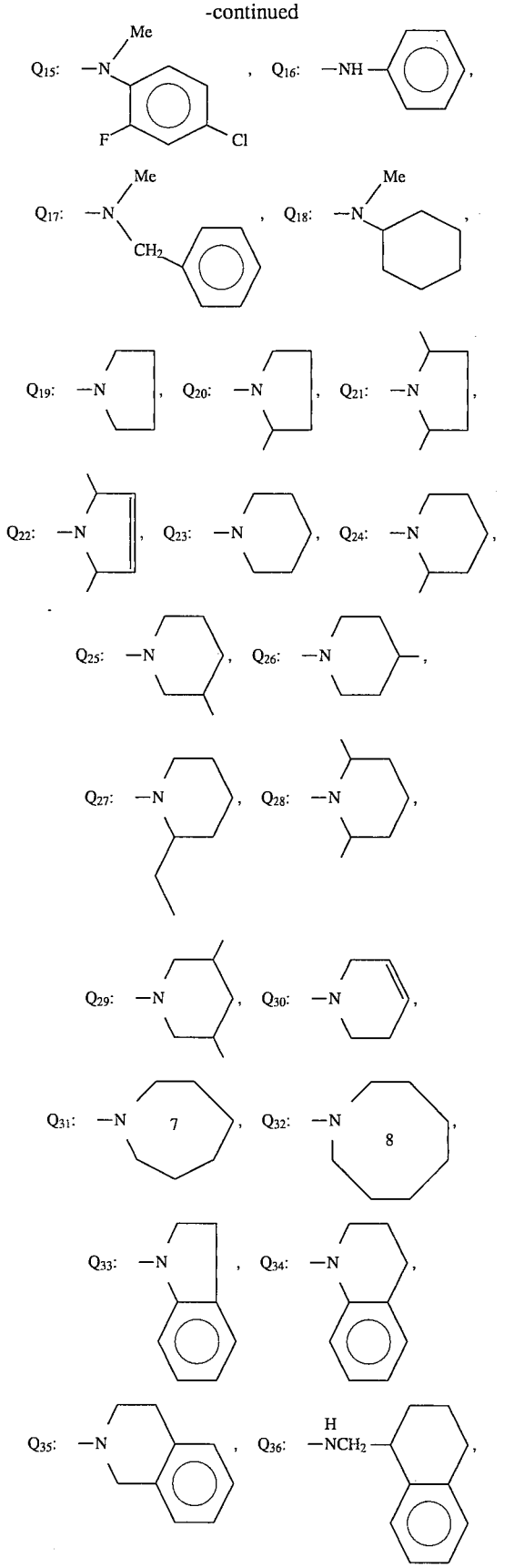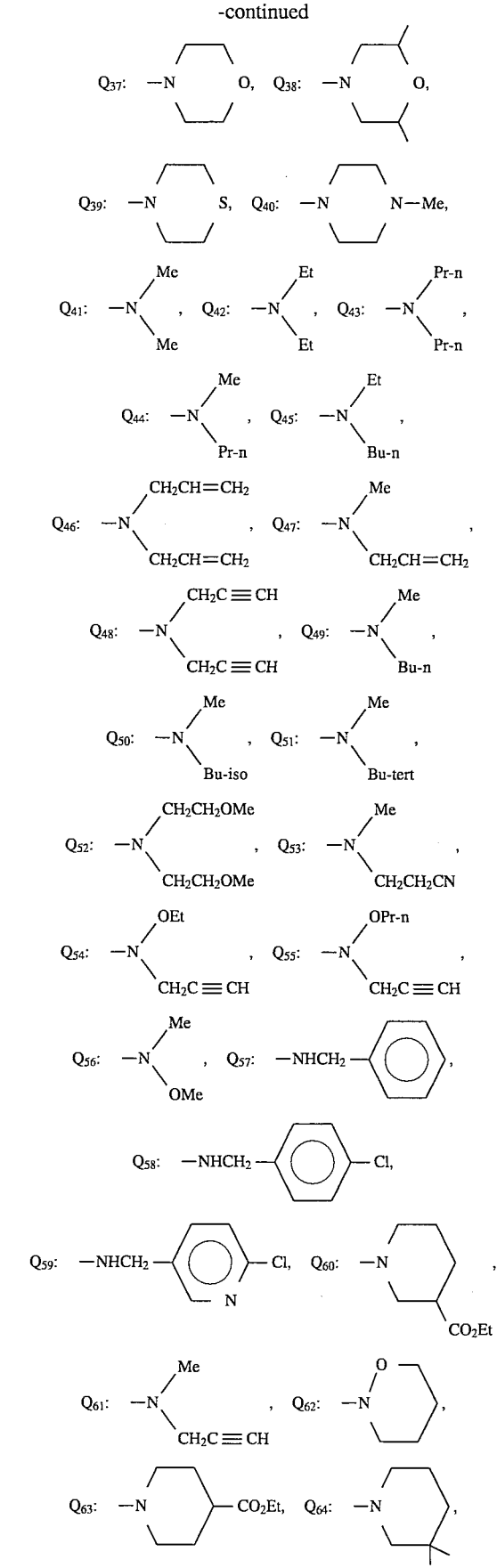

$Q_{65}$: 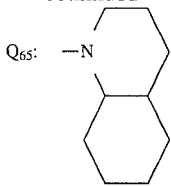

TABLE 1

$$\begin{array}{c} R^1 \quad R^3 \\ \diagdown \diagup \\ N^{\diagdown} N^{-OCH_2C(=O)NR^4R^5} \\ | \\ R^2 \end{array}$$

| No. | $R^1$ | $R^2$ | $R^3$ | $-NR^4R^5$ | Physical Properties (melting point, °C.) |
|---|---|---|---|---|---|
| 1 | Cl | Me | $NO_2$ | $Q_1$ | 104~105 |
| 2 | $CF_3$ | Me | $NO_2$ | $Q_1$ | Oily |
| 3 | Cl | Me | $NO_2$ | $Q_3$ | 129–130 |
| 4 | Cl | Me | $NO_2$ | $Q_6$ | 152~153 |
| 5 | Cl | Me | $NO_2$ | $Q_{31}$ | Oily |
| 6 | Me | Me | $NO_2$ | $Q_1$ | 108–110 |
| 7 | Me | Me | $NO_2$ | $Q_3$ | 137~139 |
| 8 | Me | Me | $NO_2$ | $Q_6$ | 126~127 |
| 9 | Me | Me | $NO_2$ | $Q_{31}$ | 97~98 |
| 10 | H | Me | $NO_2$ | $Q_1$ | 92~93 |
| 11 | $NO_2$ | Me | $NO_2$ | $Q_1$ | 86~89 |
| 12 | $NO_2$ | Me | $NO_2$ | $Q_8$ | 134~135 |
| 13 | $NO_2$ | Me | $NO_2$ | $Q_6$ | 128~130 |
| 14 | $NO_2$ | Me | $NO_2$ | $Q_{31}$ | Oily |
| 15 | Br | Me | $NO_2$ | $Q_1$ | 117~122 |
| 16 | $CF_3$ | Me | Cl | $Q_1$ | 65~66 |
| 17 | Cl | Me | CN | $Q_1$ | Oily |
| 18 | Cl | Me | $NO_2$ | $Q_8$ | 149–151 |
| 19 | Cl | Me | $NO_2$ | $Q_{15}$ | 163~165 |
| 20 | Cl | Me | $NO_2$ | $Q_{17}$ | Oily |
| 21 | Cl | Me | $NO_2$ | $Q_{42}$ | Oily |
| 22 | Cl | Me | $NO_2$ | $Q_7$ | 131~132 |
| 23 | Cl | Me | $NO_2$ | $Q_{12}$ | 206~207 |
| 24 | Cl | Me | $NO_2$ | $Q_{14}$ | 124~125 |
| 25 | Cl | Me | $NO_2$ | $Q_9$ | 104~105 |
| 26 | Cl | Me | $NO_2$ | $Q_{10}$ | 105~106 |
| 27 | Cl | Me | $NO_2$ | $Q_{11}$ | 112–113 |
| 28 | Cl | Me | $NO_2$ | $Q_4$ | 99~101 |
| 29 | Cl | Me | $NO_2$ | $Q_5$ | 107~108 |
| 30 | Cl | Me | $NO_2$ | $Q_{13}$ | 177~178 |
| 31 | Cl | Me | $NO_2$ | $Q_{27}$ | Oily |
| 32 | Cl | Me | $NO_2$ | $Q_{24}$ | Oily |
| 33 | $CF_3$ | Me | Cl | $Q_9$ | 88~89 |
| 34 | $CF_3$ | Me | Cl | $Q_{10}$ | 62~63 |
| 35 | $CF_3$ | Me | Cl | $Q_{11}$ | 91~92 |
| 36 | $CF_3$ | Me | Cl | $Q_{12}$ | 148~149 |
| 37 | $CF_3$ | Me | Cl | $Q_{14}$ | 105~106 |
| 38 | $CF_3$ | Me | Cl | $Q_6$ | 105~107 |
| 39 | $CF_3$ | Me | $NO_2$ | $Q_6$ | 136~137 |
| 40 | $CF_3$ | Me | Br | $Q_1$ | Oily |
| 41 | $CF_3$ | Me | Br | $Q_{24}$ | Oily |
| 42 | $CF_3$ | Me | Br | $Q_6$ | 104~106 |
| 43 | Br | Me | $NO_2$ | $Q_6$ | 82~86 |
| 44 | Br | Et | $NO_2$ | $Q_6$ | Oily |
| 45 | Br | Pr-iso | $NO_2$ | $Q_6$ | Oily |
| 46 | Me | Me | Cl | $Q_1$ | 59–60 |
| 47 | Et | Me | Cl | $Q_1$ | 65~66 |
| 48 | Pr-n | Me | Cl | $Q_1$ | Oily |
| 49 | Pr-cyc | Me | Cl | $Q_1$ | Oily |
| 50 | $CF_2Cl$ | Me | Cl | $Q_1$ | 75~76 |
| 51 | H | Me | Cl | $Q_1$ | Oily |
| 52 | H | Et | Cl | $Q_1$ | 68~70 |
| 53 | Cl | Me | CN | $Q_6$ | 114~115 |
| 54 | Pr-n | Me | $NO_2$ | $Q_1$ | 91~95 |
| 55 | Pr-n | Me | $NO_2$ | $Q_6$ | 75~78 |
| 56 | Pr-n | Me | $NO_2$ | $Q_3$ | 66~70 |
| 57 | Ph | Me | Cl | $Q_1$ | Oily |
| 58 | $CF_3$ | Me | $NO_2$ | $Q_{10}$ | 100~101 |
| 59 | $CF_3$ | Me | $NO_2$ | $Q_{24}$ | Oily |
| 60 | $CF_3$ | Me | $NO_2$ | $Q_{31}$ | Oily |
| 61 | $CF_3CF_2$ | Me | Cl | $Q_6$ | 78~80 |
| 62 | $CF_3$ | Ph | Cl | $Q_6$ | Oily |
| 63 | $CF_3$ | Ph | Cl | $Q_{31}$ | 67~68 |
| 64 | $CF_3$ | Ph | Cl | $Q_{10}$ | 85~86 |
| 65 | $CF_3$ | Ph | Cl | $Q_{24}$ | 106~108 |
| 66 | $CF_3$ | Ph | Cl | $Q_{23}$ | Oily |
| 67 | $CF_3$ | 2-Py | Cl | $Q_{31}$ | 108~109 |
| 68 | $CF_3CF_2$ | Me | Cl | $Q_{27}$ | Oily |
| 69 | $CF_3$ | Me | Cl | $Q_{27}$ | Oily |
| 70 | $CF_3$ | Me | Cl | $Q_{13}$ | 131~132 |
| 71 | 3-Cl—Ph | Me | Cl | $Q_6$ | Oily |
| 72 | $CF_3$ | Ph | Cl | $Q_{32}$ | 74~75 |
| 73 | $CF_3$ | Ph | Cl | $Q_2$ | 129~130 |
| 74 | $CF_3$ | 2-Me—Ph | Cl | $Q_{31}$ | 82~83 |
| 75 | $CF_3$ | 3-Me—Ph | Cl | $Q_{31}$ | Oily |
| 76 | $CF_3$ | 4-Me—Ph | Cl | $Q_{31}$ | 86~87 |
| 77 | $CF_3$ | Ph | Cl | $Q_1$ | 79~80 |
| 78 | $CF_3$ | 2-Cl—Ph | Cl | $Q_{31}$ | 53~54 |
| 79 | $CF_3$ | 3-Cl—Ph | Cl | $Q_{31}$ | 64~65 |
| 80 | $CF_3$ | 4-Cl—Ph | Cl | $Q_{31}$ | Oily |
| 81 | $CF_3$ | Ph | Cl | $Q_{19}$ | Oily |
| 82 | $CF_3$ | 2-Cl—Ph | Cl | $Q_{23}$ | Oily |
| 83 | $CF_3$ | 3-Cl—Ph | Cl | $Q_{23}$ | Oily |
| 84 | $CF_3$ | 4-Cl—Ph | Cl | $Q_{23}$ | Oily |
| 85 | $CF_3$ | 2-Br—Ph | Cl | $Q_{23}$ | 93~94 |
| 86 | $CF_3$ | 2-$NO_2$—Ph | Cl | $Q_{23}$ | Oily |
| 87 | $CF_3$ | 2-F—Ph | Cl | $Q_{23}$ | 72~73 |
| 88 | $CF_3$ | 4-F—Ph | Cl | $Q_{23}$ | 74~75 |
| 89 | $CF_3$ | Ph | Cl | $Q_{42}$ | 69~71 |
| 90 | $CF_3$ | Ph | Cl | $Q_{43}$ | Oily |
| 91 | $CF_3$ | Ph | Cl | $Q_{37}$ | 93~94 |
| 92 | $CF_3$ | Ph | Cl | $Q_{46}$ | Oily |
| 93 | $CF_3$ | 4-$CF_3$—Ph | Cl | $Q_{23}$ | 61~62 |
| 94 | $CF_3$ | 4-$NO_2$—Ph | Cl | $Q_{23}$ | 83~84 |
| 95 | $CF_3$ | 4-MeO—Ph | Cl | $Q_{23}$ | 102~104 |
| 96 | $CF_3$ | 2,4-$Cl_2$—Ph | Cl | $Q_{23}$ | 107~108 |
| 97 | $CF_3$ | Ph | Cl | $Q_{29}$ | Oily |
| 98 | $CF_3$ | Me | $NO_2$ | $Q_{23}$ | 73~74 |
| 99 | Cl | Me | $NO_2$ | $Q_{23}$ | 93~94 |
| 100 | $CF_3$ | Ph | Cl | $Q_{25}$ | Oily |
| 101 | $CF_3$ | Ph | Cl | $Q_{26}$ | Oily |
| 102 | $CF_3$ | Ph | Cl | $Q_{28}$ | 105~106 |
| 103 | $CF_3$ | Me | Cl | $Q_{23}$ | Oily |
| 104 | $CF_3$ | Ph | Cl | $Q_{18}$ | Oily |
| 105 | $CF_3$ | Ph | Cl | $Q_{49}$ | Oily |
| 106 | $CF_3$ | Ph | Cl | $Q_{50}$ | Oily |
| 107 | $CF_3$ | 3-$CF_3$—Ph | Cl | $Q_{23}$ | 68~69 |
| 108 | $CF_3$ | 2-Py | Cl | $Q_{23}$ | 105~106 |
| 109 | $CF_3$ | Ph | Cl | $Q_{21}$ | 120~121 |
| 110 | $CF_3$ | Ph | Cl | $Q_{38}$ | 133~134 |
| 111 | $CF_3$ | Ph | Cl | $Q_{52}$ | Oily |
| 112 | $CF_3$ | Ph | Cl | $Q_{53}$ | Oily |
| 113 | $CF_3$ | Ph | Cl | $Q_{17}$ | Oily |
| 114 | $CF_3$ | Ph | Cl | $Q_{36}$ | 130~131 |
| 115 | Me | Ph | Cl | $Q_{23}$ | 65~66 |
| 116 | $CF_3$ | 3-F—Ph | Cl | $Q_{23}$ | Oily |
| 117 | $CF_3$ | 3,4-$Cl_2$—Ph | Cl | $Q_{23}$ | 75~76 |
| 118 | $CF_3$ | 3-$CF_3$—Ph | Cl | $Q_{23}$ | Oily |
| 119 | $CF_3$ | Ph | Cl | $Q_{33}$ | 137~138 |
| 120 | $CF_3$ | Ph | Cl | $Q_{34}$ | 62~63 |
| 121 | $CF_3$ | Ph | Cl | $Q_{35}$ | 118~119 |
| 122 | $CF_3$ | 2,5-$Cl_2$—Ph | Cl | $Q_{23}$ | 61~62 |

TABLE 1-continued

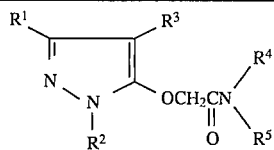

| No. | R¹ | R² | R³ | —NR⁴R⁵ | Physical Properties (melting point, °C.) |
|---|---|---|---|---|---|
| 123 | CF₃ | CH₂Ph | Cl | Q₂₃ | 72~73 |
| 124 | CF₃ | Ph | Br | Q₂₃ | 59~60 |
| 125 | CF₃ | Ph | Cl | Q₄₈ | 86~87 |
| 126 | CF₃ | Ph | Cl | Q₅₁ | 84~85 |
| 127 | CF₃ | Ph | Cl | Q₄₄ | Oily |
| 128 | CF₃ | Ph | Cl | Q₃₉ | 89~90 |
| 129 | CF₃ | Ph | Cl | Q₄₀ | 85~86 |
| 130 | CF₃ | Et | Cl | Q₂₃ | Oily |
| 131 | CF₃ | Et | Cl | Q₃₁ | Oily |
| 132 | CF₃ | Pr-n | Cl | Q₂₃ | Oily |
| 133 | CF₃ | 3-Me—Ph | Cl | Q₁₉ | Oily |
| 134 | CF₃ | Ph | Cl | Q₃₀ | 62~63 |
| 135 | CF₃ | Ph | Cl | Q₂₂ | Oily |
| 136 | CF₃ | Pr-n | Cl | Q₁ | Oily |
| 137 | CF₃ | Bu-tert | Cl | Q₂₃ | 72~73 |
| 138 | CF₃ | Ph | Cl | Q₂₀ | Oily |
| 139 | CF₃ | Pr-n | Cl | Q₃₁ | Oily |
| 140 | CF₃ | 3-Cl-5-CF₃-2-Py | Cl | Q₂₃ | Oily |
| 141 | CF₃ | Ph | Cl | Q₅₄ | Oily |
| 142 | CF₃ | Ph | Cl | Q₄₁ | 57~58 |
| 143 | CF₃ | Pr-iso | Cl | Q₂₃ | Oily |
| 144 | CF₃ | Ph | Cl | Q₄₅ | Oily |
| 145 | CF₃ | Ph | Cl | Q₁₆ | 95~96 |
| 146 | Cl | Ph | Cl | Q₂₃ | Oily |
| 147 | CF₃ | 1-NaPh | Cl | Q₂₃ | Oily |
| 148 | CF₃ | CH₂C≡CH | Cl | Q₂₃ | 78~79 |
| 149 | CF₃ | Ph | Cl | Q₄₇ | Oily |
| 150 | H | Me | H | Q₁ | 77~78 |
| 151 | CF₃ | Me | H | Q₂₄ | Oily |
| 152 | CF₃ | Me | H | Q₁ | 100~102 |
| 153 | Pr-cyc | Me | H | Q₁ | 97~99 |
| 154 | Me | Me | H | Q₁ | 84~85 |
| 155 | H | Et | H | Q₁ | Oily |
| 156 | ClF₂C | Me | H | Q₁ | 82~83 |
| 157 | Pr-iso | Me | H | Q₁ | 50~51 |
| 158 | Et | Me | H | Q₁ | 78~79 |
| 159 | 3-Cl—Ph | Me | H | Q₆ | 112~113 |
| 160 | CF₃ | 2-Py | H | Q₃₁ | 109~110 |
| 161 | CF₃ | 2-Py | H | Q₂₃ | 125~126 |
| 162 | Me | Ph | H | Q₂₃ | 76~77 |
| 163 | CF₃ | H | H | Q₂₃ | 154~156 |
| 164 | CF₃ | Ph | Cl | Q₅₅ | Oily |
| 165 | CF₃ | Ph | Cl | Q₅₆ | Oily |
| 166 | CF₃ | Ph | Cl | Q₅₇ | 94~95 |
| 167 | CF₃ | Ph | Cl | Q₅₈ | 111~112 |

TABLE 1-continued

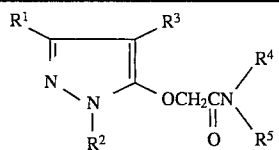

| No. | R¹ | R² | R³ | —NR⁴R⁵ | Physical Properties (melting point, °C.) |
|---|---|---|---|---|---|
| 168 | CF₃ | Ph | Cl | Q₅₉ | Oily |
| 169 | CF₃ | CH₂CH₂CN | H | Q₁ | 79~81 |
| 170 | CF₃ | Ph | Cl | Q₆₀ | Oily |
| 171 | CF₃ | 3,5-Cl₂—Ph | Cl | Q₂₃ | 68~69 |
| 172 | CF₃ | 3,5-Cl₂—Ph | H | Q₂₃ | 108~110 |
| 173 | CF₃ | Ph | Cl | Q₆₁ | Oily |
| 174 | CF₃ | CH₂CH₂CN | Cl | Q₁ | 68~69 |
| 175 | CF₃ | Hex-cyc | H | Q₆ | Oily |
| 176 | CF₃ | Ph | Cl | Q₆₂ | 67~69 |
| 177 | Cl | Ph | H | Q₂₃ | 96~98 |
| 178 | CF₃ | Hex-cyc | Cl | Q₆ | Oily |
| 179 | Ph | Ph | H | Q₂₃ | 139~140 |
| 180 | Ph | Ph | Cl | Q₂₃ | 105~106 |
| 181 | CF₃ | Ph | Cl | Q₆₃ | Oily |
| 182 | CF₃ | Ph | Cl | Q₆₄ | 88~90 |
| 183 | CF₃ | Hex-cyc | H | Q₂₃ | 81~82 |
| 184 | CF₃ | CH₂CH=CH₂ | Cl | Q₂₃ | Oily |
| 185 | CF₃ | Ph | Cl | Q₆₅ | Oily |

Examples of the compounds of the present invention are shown in the following Table 2, Table 3 and Table 4 along with the compounds produced in the above-mentioned examples, which, however, are not intended to restrict the scope of the present invention. The definitions of the abbreviated expressions used therein are mentioned below.

Me: methyl group
Et: ethyl group
Pr-n: normal propyl group
Pr-iso: isopropyl group
Bu-n: normal butyl group
Bu-iso: isobutyl group
Bu-sec: secondary butyl group
Bu-tert: tertiary butyl group
Pen-n: normal pentyl group
Hex-n: normal hexyl group
Pr-cyc: cyclopropyl group
Bu-cyc: cyclobutyl group
Pen-cyc: cylopentyl group
Hex-cyc: cyclohexyl group
Ph: phenyl group

TABLE 2

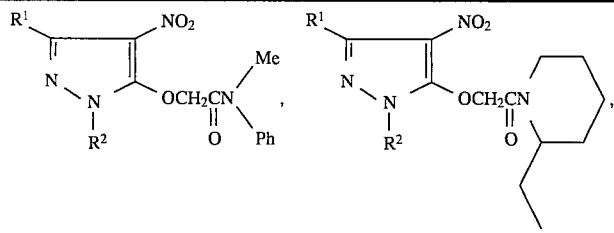

TABLE 2-continued
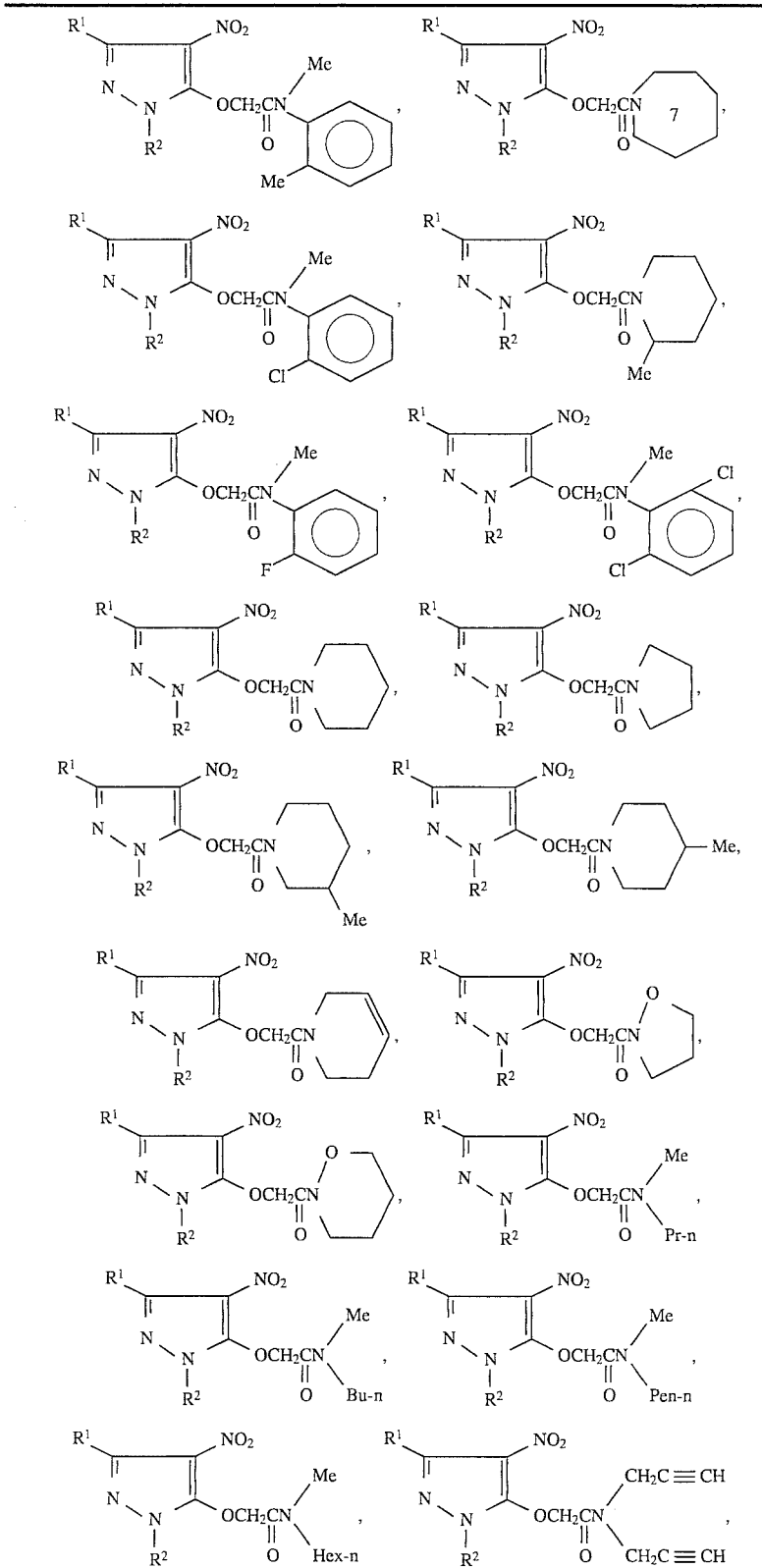

TABLE 2-continued
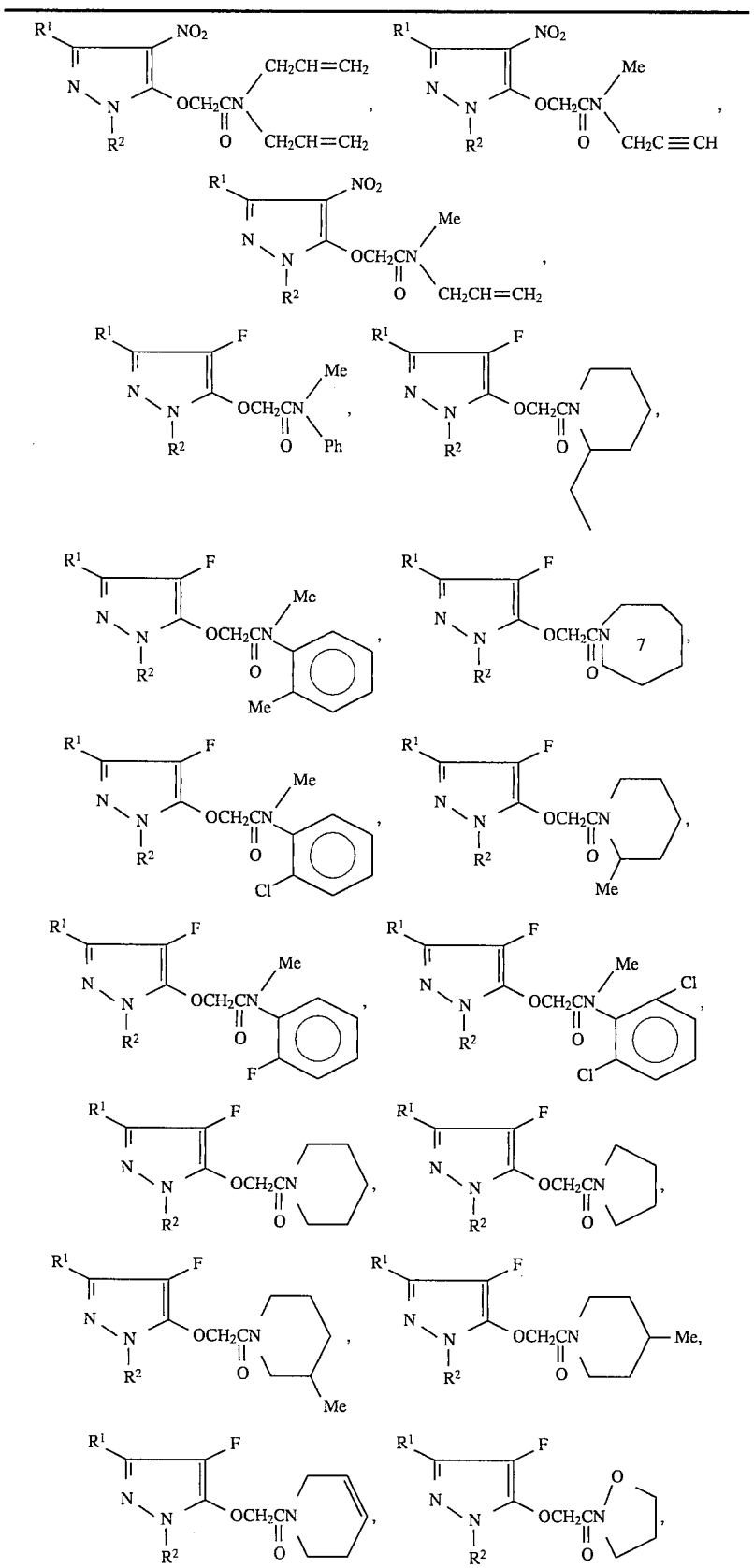

TABLE 2-continued
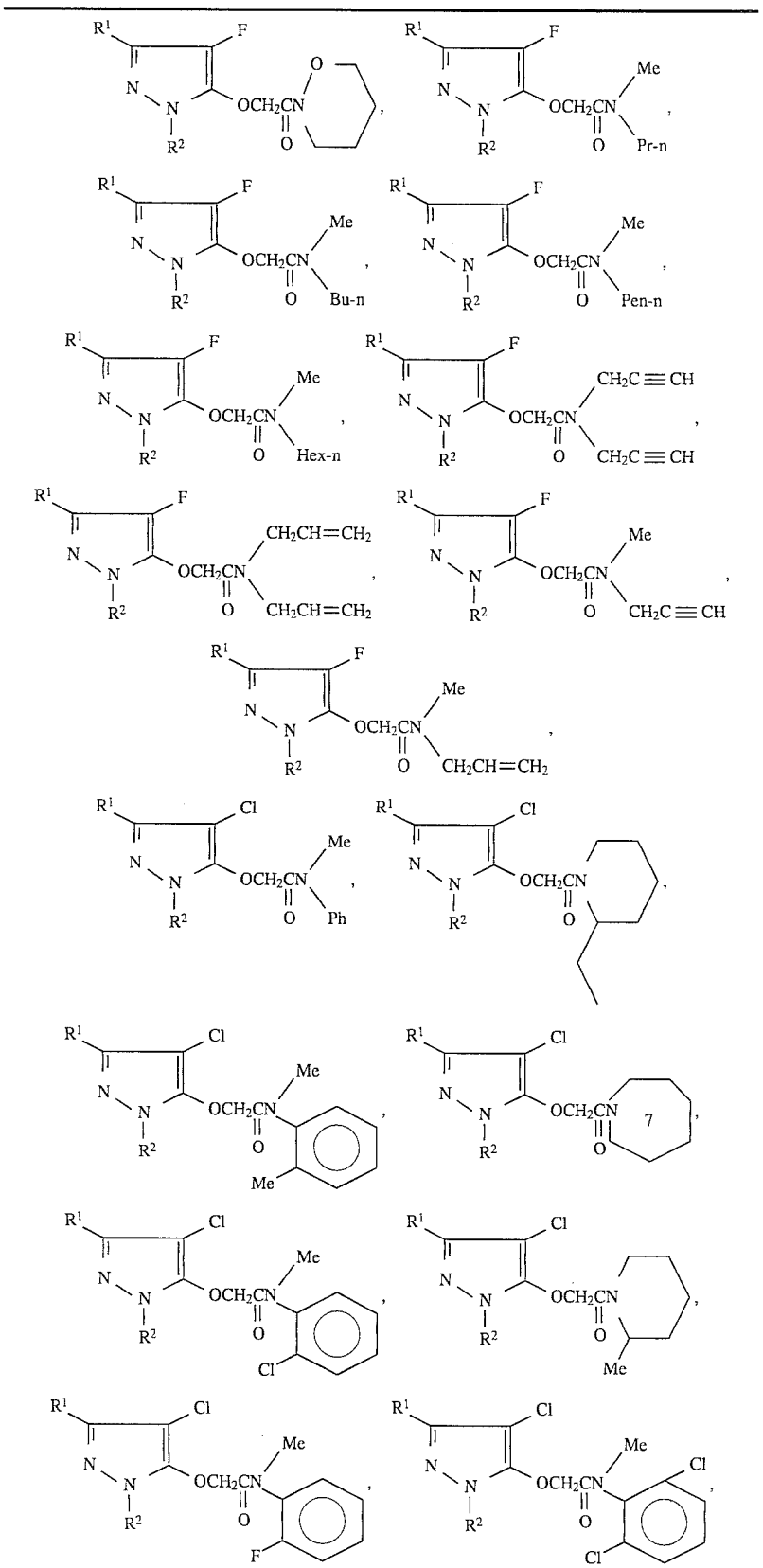

TABLE 2-continued
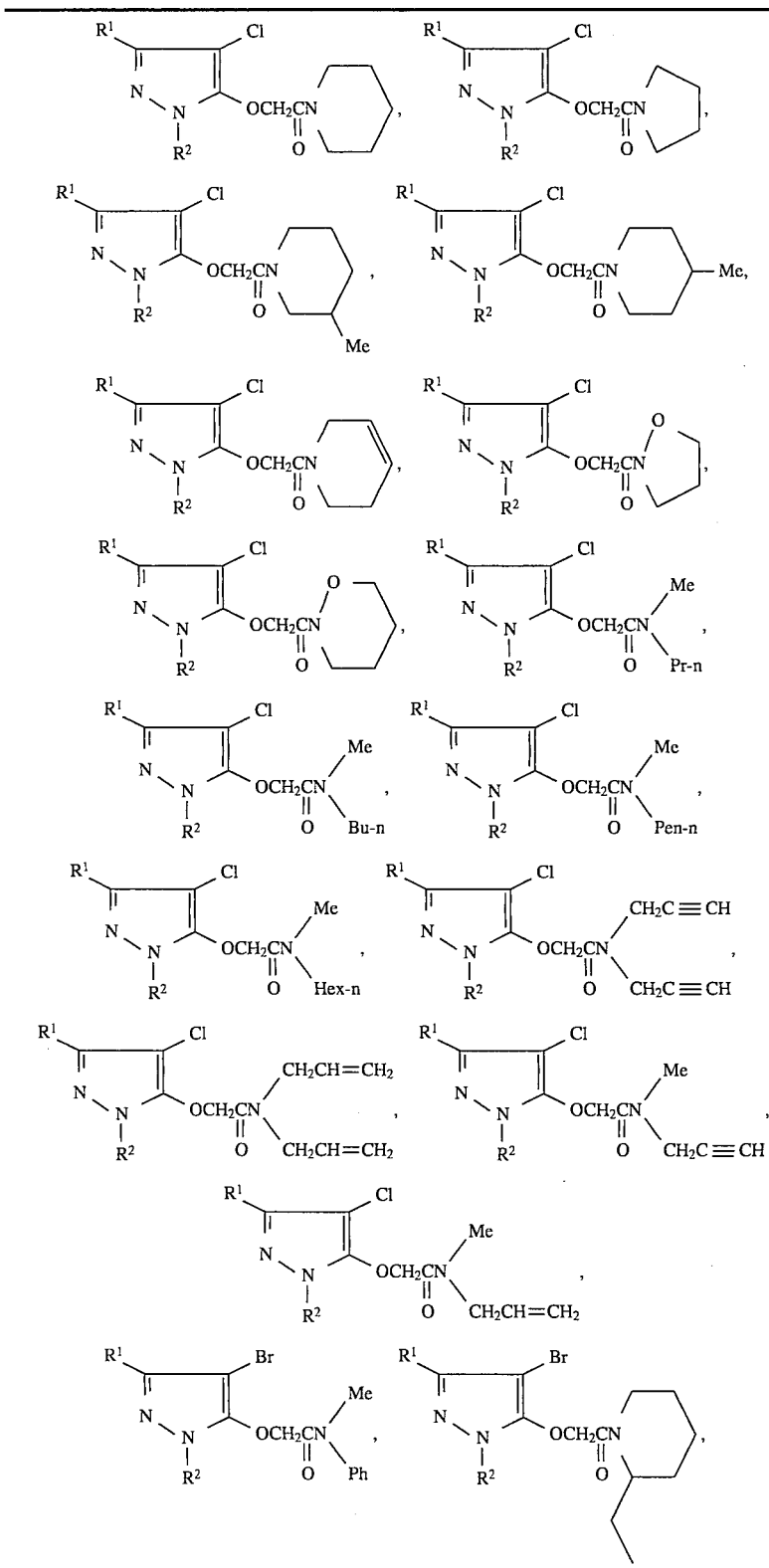

TABLE 2-continued
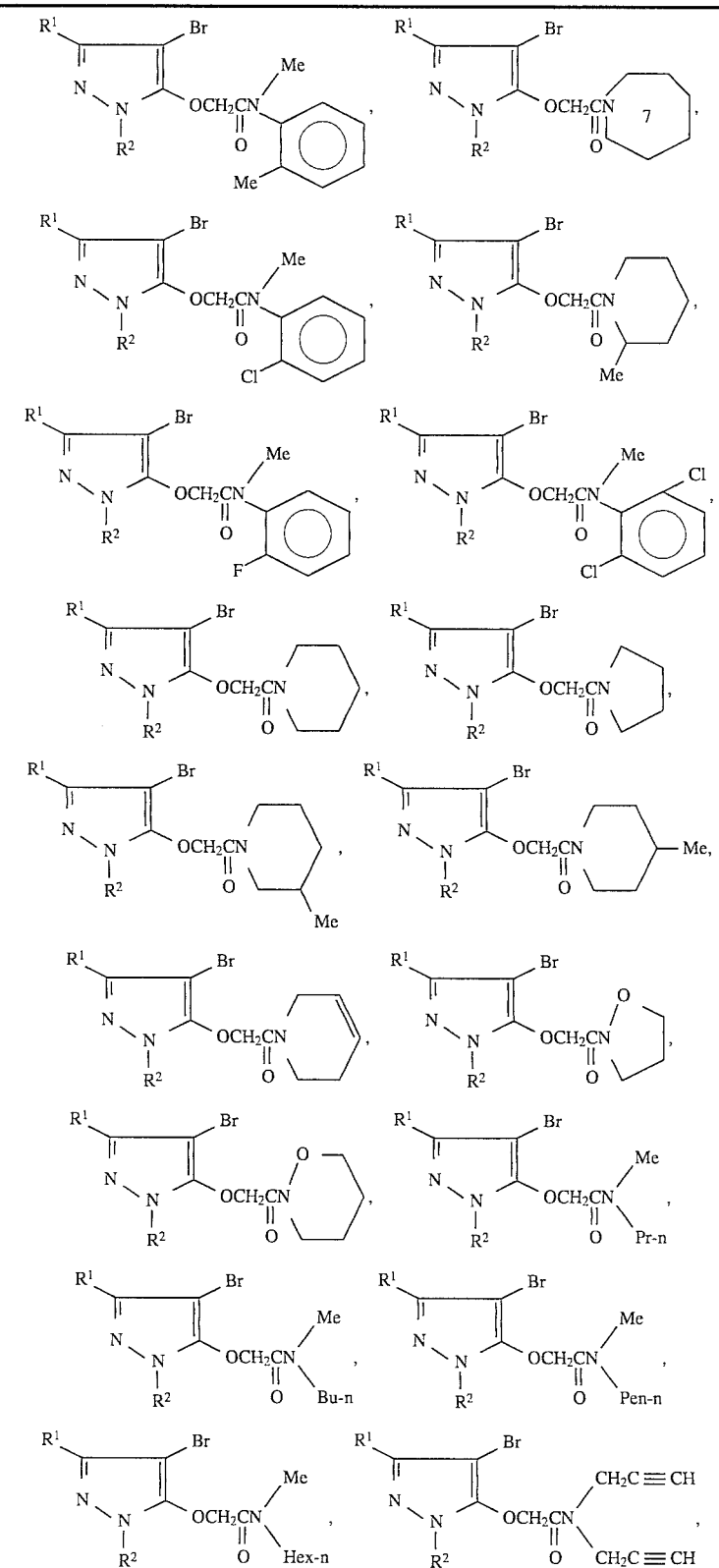

TABLE 2-continued
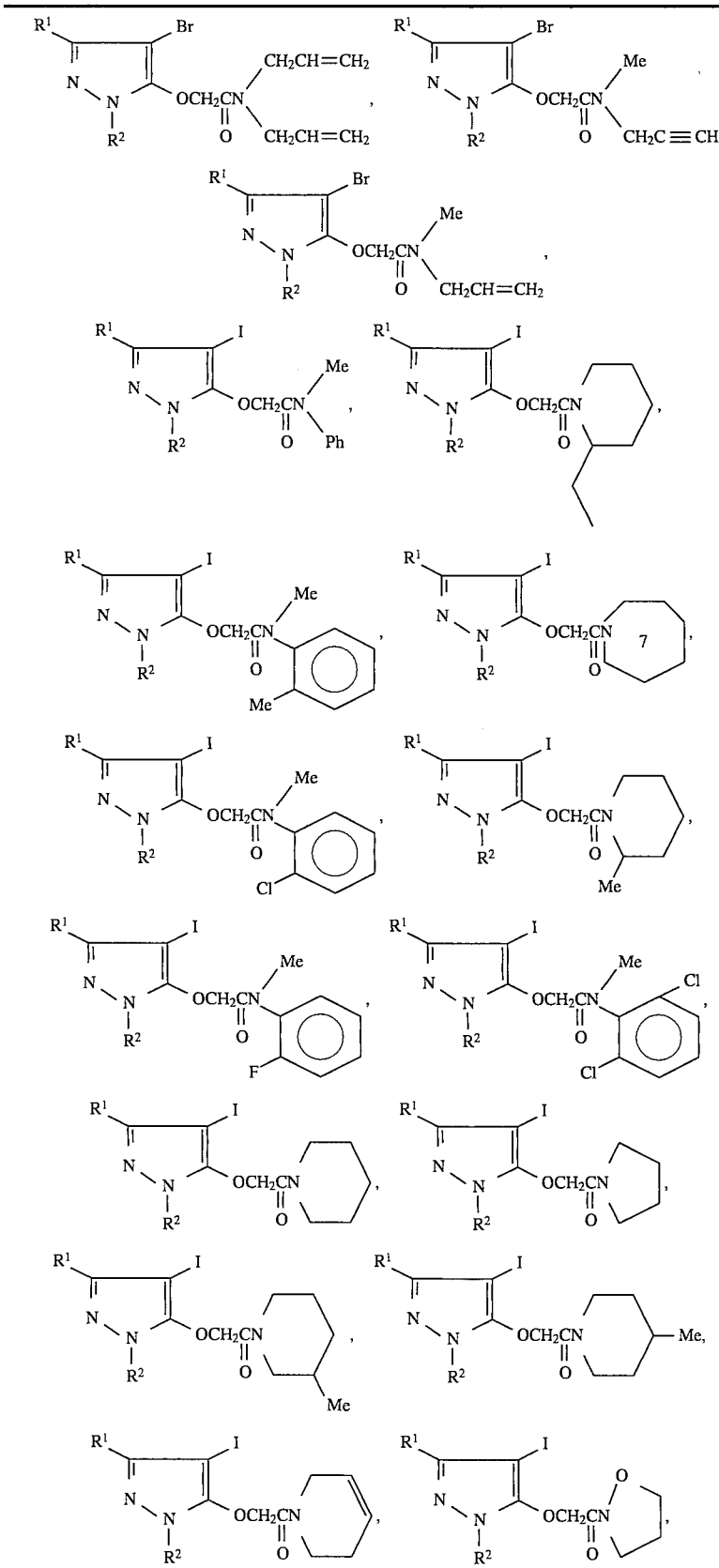

TABLE 2-continued
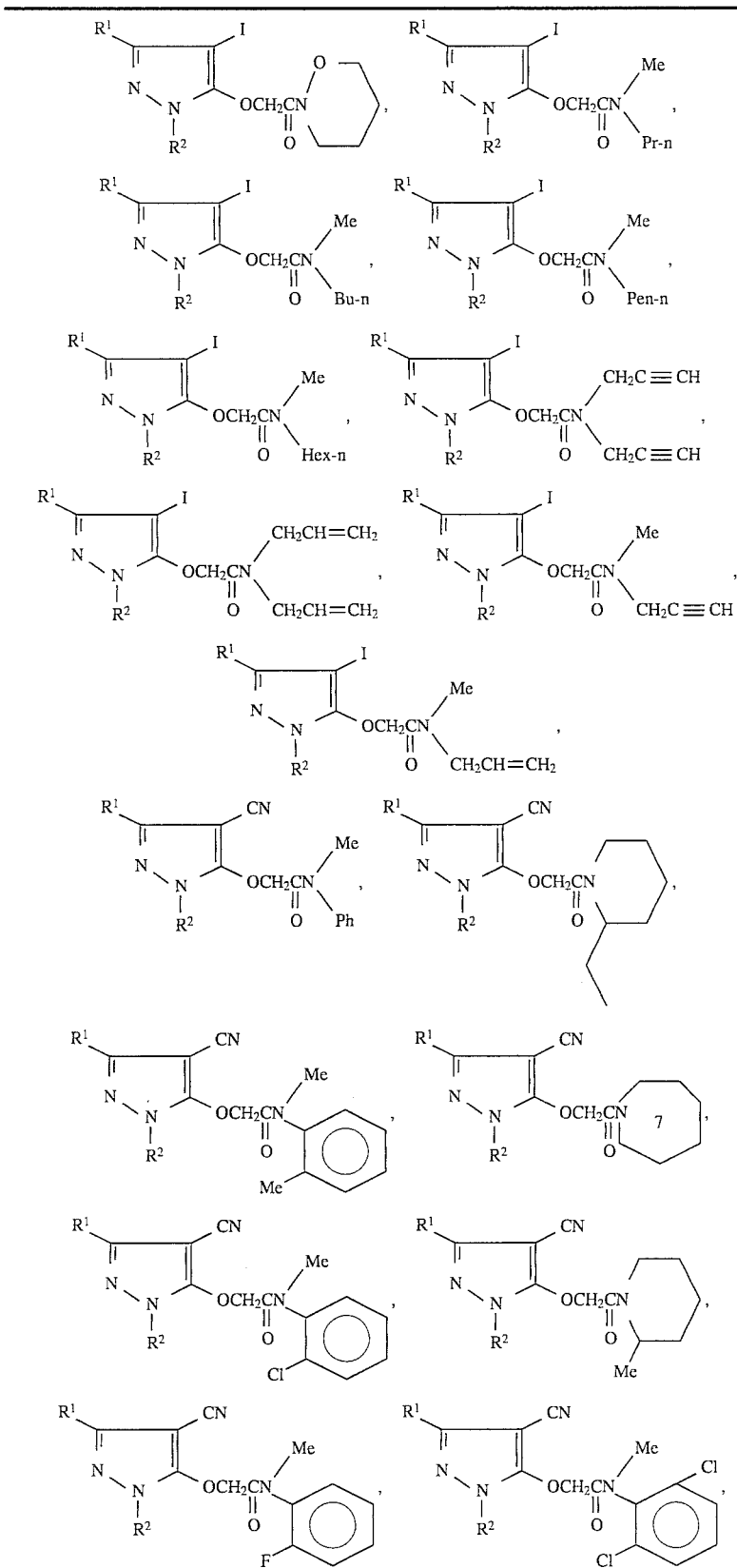

TABLE 2-continued
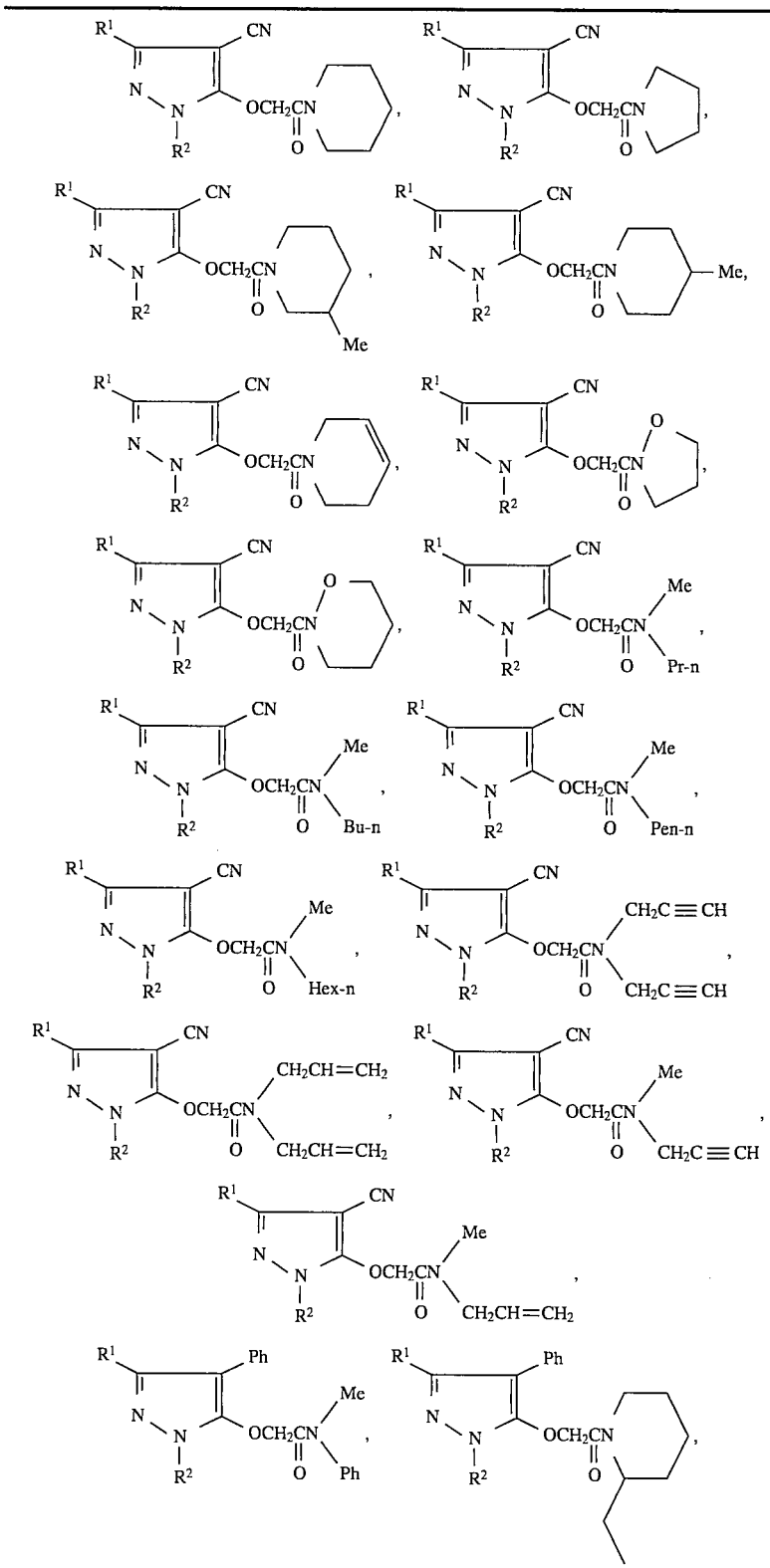

TABLE 2-continued
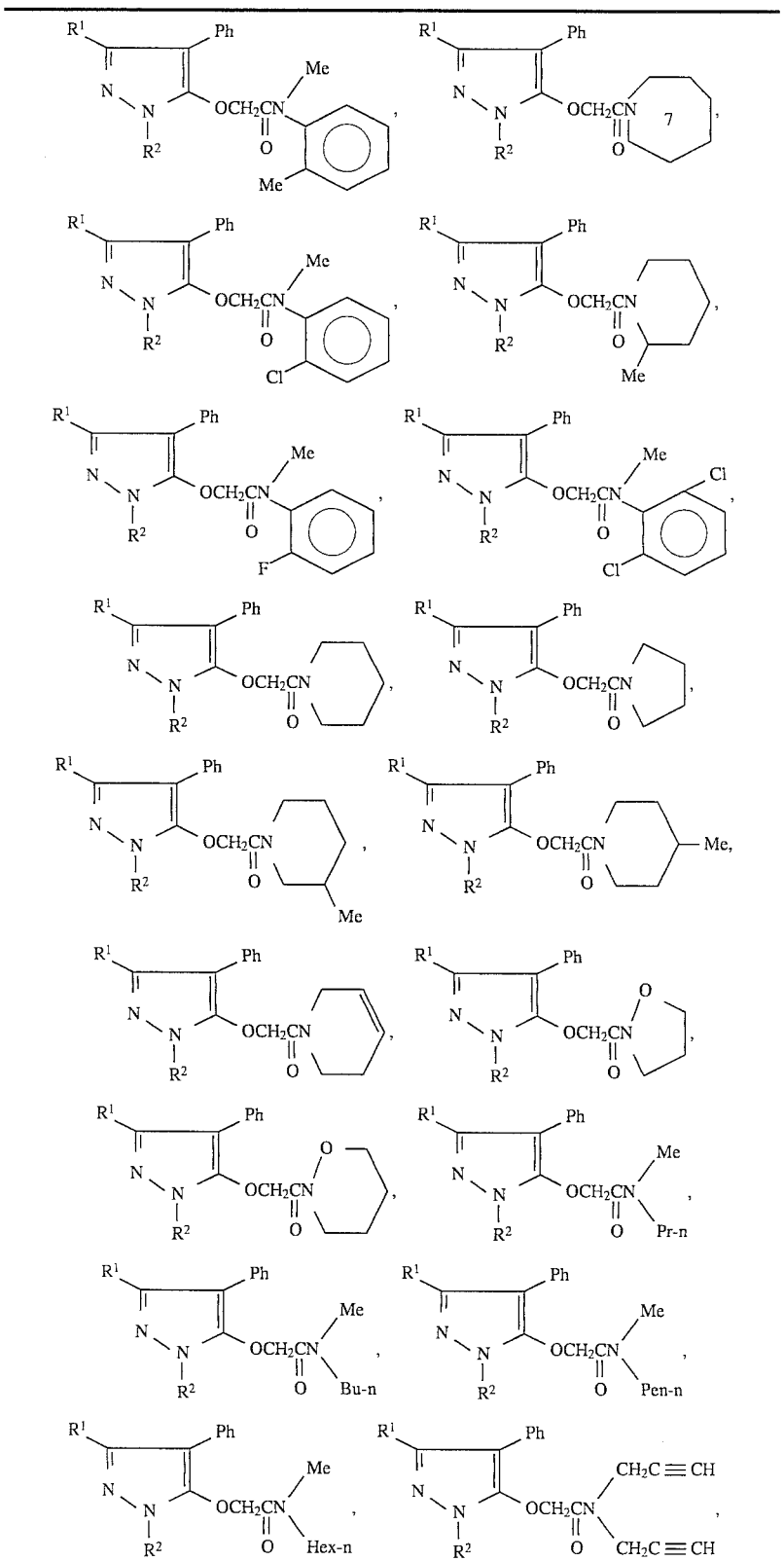

TABLE 2-continued
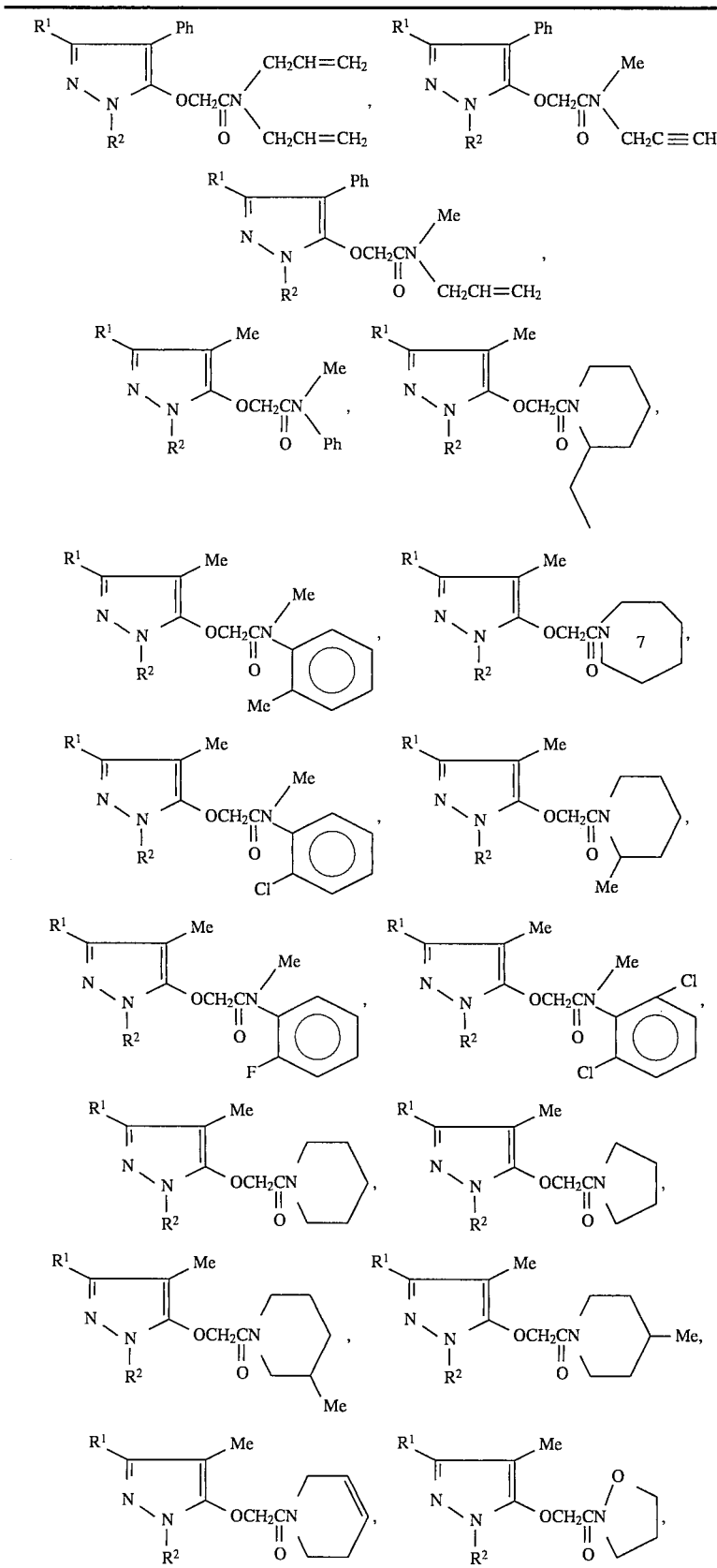

TABLE 2-continued
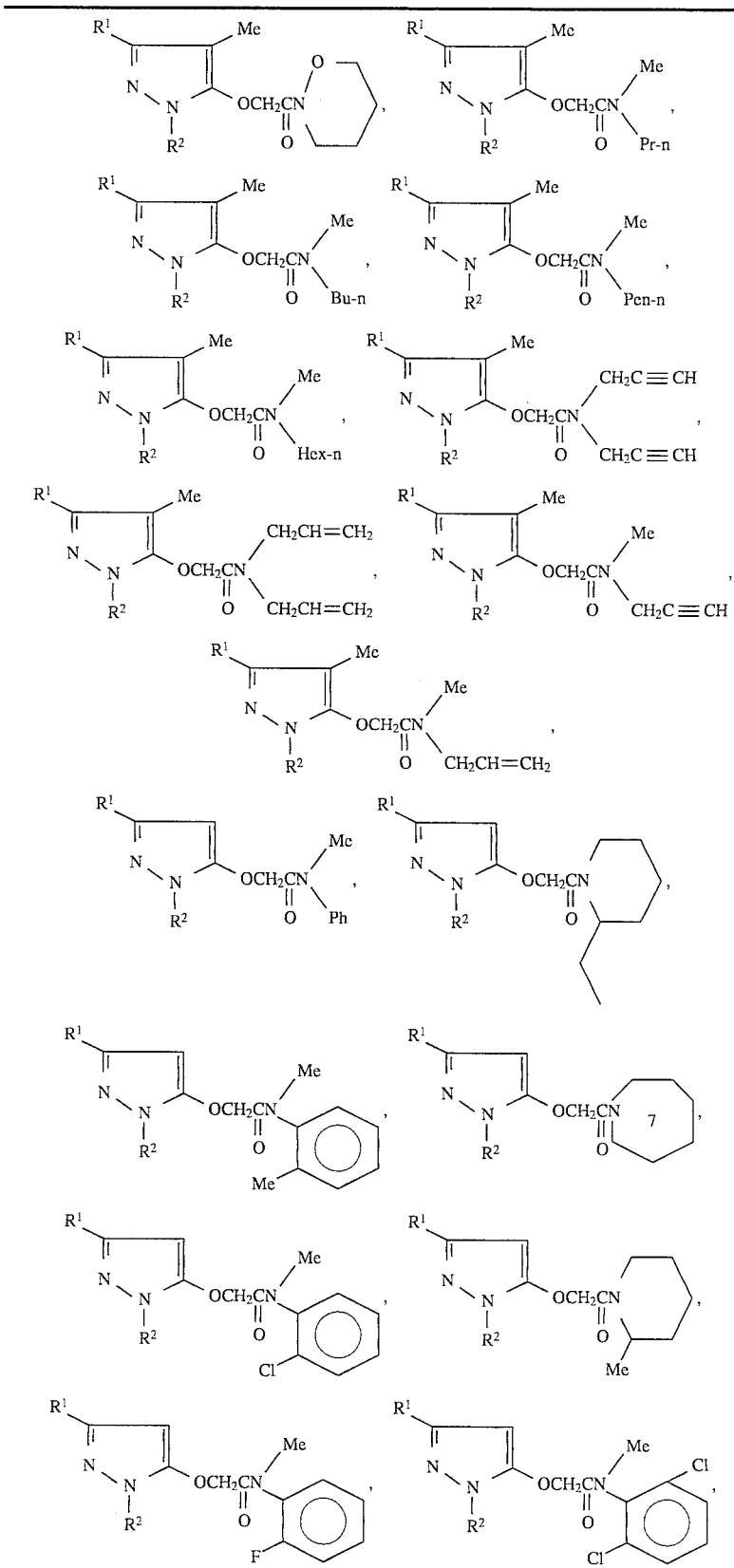

TABLE 2-continued

| R¹ | R² |
|---|---|
| H | Me |
| H | Et |
| H | Pr-n |
| H | Pr-iso |
| H | CH$_2$Pr-cyc |
| H | CH$_2$CH=CH$_2$ |
| H | CH$_2$C≡CH |
| H | CH$_2$F |
| H | CHF$_2$ |
| H | CF$_3$ |
| H | CH$_2$OMe |
| H | SO$_2$Me |
| H | SO$_2$NMe$_2$ |
| H | Ph |

TABLE 2-continued

| | |
|---|---|
| H | CH₂Ph |
| H | CO₂Me |
| H | COMe |
| H | CONMe₂ |
| H | CH₂CO₂Me |
| H | CHMeCO₂Et |
| H | CH₂COMe |
| Me | Me |
| Me | Et |
| Me | Pr-n |
| Me | Pr-iso |
| Me | CH₂Pr-cyc |
| Me | CH₂CH=CH₂ |
| Me | CH₂C≡CH |
| Me | CH₂F |
| Me | CHF₂ |
| Me | CF₃ |
| Me | CH₂OMe |
| Me | SO₂Me |
| Me | SO₂NMe₂ |
| Me | Ph |
| Me | CH₂Ph |
| Me | CO₂Me |
| Me | COMe |
| Me | CONMe₂ |
| Me | CH₂CO₂Me |
| Me | CHMeCO₂Et |
| Me | CH₂COMe |
| Cl | Me |
| Cl | Et |
| Cl | Pr-n |
| Cl | Pr-iso |
| Cl | Bu-n |
| Cl | Pen-n |
| Cl | Hex-n |
| Cl | CH₂Pr-cyc |
| Cl | CH₂CH=CH₂ |
| Cl | CH₂C≡CH |
| Cl | CH₂F |
| Cl | CHF₂ |
| Cl | CF₃ |
| Cl | CH₂OMe |
| Cl | SO₂Me |
| Cl | SO₂NMe₂ |
| Cl | Ph |
| Cl | CH₂Ph |
| Cl | CO₂Me |
| Cl | COMe |
| Cl | CONMe₂ |
| Cl | CH₂CO₂Me |
| Cl | CHMeCO₂Et |
| Cl | CH₂COMe |
| Br | Me |
| Br | Et |
| Br | Pr-n |
| Br | Pr-iso |
| Br | CH₂Pr-cyc |
| Br | CH₂CH=CH₂ |
| Br | CH₂C≡CH |
| Br | CH₂F |
| Br | CHF₂ |
| Br | CF₃ |
| Br | CH₂OMe |
| Br | SO₂Me |
| Br | SO₂NMe₂ |
| Br | Ph |
| Br | CH₂Ph |
| Br | CO₂Me |
| Br | COMe |
| Br | CONMe₂ |
| Br | CH₂CO₂Me |
| Br | CHMeCO₂Et |
| Br | CH₂COMe |
| NO₂ | Me |
| NO₂ | Et |
| NO₂ | Pr-n |

TABLE 2-continued

| | |
|---|---|
| NO$_2$ | Pr-iso |
| NO$_2$ | CH$_2$Pr-cyc |
| NO$_2$ | CH$_2$CH=CH$_2$ |
| NO$_2$ | CH$_2$C≡CH |
| NO$_2$ | CH$_2$F |
| NO$_2$ | CHF$_2$ |
| NO$_2$ | CF$_3$ |
| NO$_2$ | CH$_2$OMe |
| NO$_2$ | SO$_2$Me |
| NO$_2$ | SO$_2$NMe$_2$ |
| NO$_2$ | Ph |
| NO$_2$ | CH$_2$Ph |
| NO$_2$ | CO$_2$Me |
| NO$_2$ | COMe |
| NO$_2$ | CONMe$_2$ |
| NO$_2$ | CH$_2$CO$_2$Me |
| NO$_2$ | CHMeCO$_2$Et |
| NO$_2$ | CH$_2$COMe |
| CF$_3$ | Me |
| CF$_3$ | Et |
| CF$_3$ | Pr-n |
| CF$_3$ | Pr-iso |
| CF$_3$ | Bu-n |
| CF$_3$ | Pen-n |
| CF$_3$ | Hex-n |
| CF$_3$ | Bu-tert |
| CF$_3$ | CH$_2$Pr-cyc |
| CF$_3$ | CH$_2$CH=CH$_2$ |
| CF$_3$ | CH$_2$C≡CH |
| CF$_3$ | CH$_2$F |
| CF$_3$ | CHF$_2$ |
| CF$_3$ | CF$_3$ |
| CF$_3$ | CH$_2$OMe |
| CF$_3$ | SO$_2$Me |
| CF$_3$ | SO$_2$NMe$_2$ |
| CF$_3$ | Ph |
| CF$_3$ | CH$_2$Ph |
| CF$_3$ | CO$_2$Me |
| CF$_3$ | COMe |
| CF$_3$ | CONMe$_2$ |
| CF$_3$ | CH$_2$CO$_2$Me |
| CF$_3$ | CHMeCO$_2$Et |
| CF$_3$ | CH$_2$COMe |
| Et | Me |
| Et | Pr-iso |
| Et | Et |
| Et | CHF$_2$ |
| Et | CF$_3$ |
| Et | CH$_2$OMe |
| Et | Ph |
| Et | CH$_2$Ph |
| Et | CO$_2$Me |
| Et | COMe |
| Et | CH$_2$CO$_2$Me |
| MeO | Me |
| MeO | Et |
| MeO | Pr-iso |
| MeO | CH$_2$OMe |
| MeO | Ph |
| MeS | Me |
| MeS | Et |
| MeS | Pr-iso |
| MeS | CH$_2$OMe |
| MeS | Ph |
| F | Me |
| F | Et |
| F | Pr-iso |
| F | CH$_2$OMe |
| F | Ph |
| Pr-n | Me |
| Pr-n | Et |
| Pr-n | Pr-iso |
| Pr-n | CH$_2$OMe |
| Pr-n | Ph |
| Pr-iso | Me |
| Pr-iso | Et |
| Pr-iso | Pr-iso |

TABLE 2-continued

| | |
|---|---|
| Pr-iso | $CH_2OMe$ |
| Pr-iso | Ph |
| Pr-cyc | Me |
| Pr-cyc | Et |
| Pr-cyc | Pr-iso |
| Pr-cyc | $CH_2OMe$ |
| Pr-cyc | Ph |
| $CH_2F$ | Me |
| $CH_2F$ | Et |
| $CH_2F$ | Pr-iso |
| $CH_2F$ | $CH_2OMe$ |
| $CH_2F$ | Ph |
| $CH_2Cl$ | Me |
| $CH_2Cl$ | Et |
| $CH_2Cl$ | Pr-iso |
| $CH_2Cl$ | $CH_2OMe$ |
| $CH_2Cl$ | Ph |
| $CHF_2$ | Me |
| $CHF_2$ | Et |
| $CHF_2$ | Pr-iso |
| $CHF_2$ | $CH_2OMe$ |
| $CHF_2$ | Ph |
| $CClF_2$ | Me |
| $CClF_2$ | Et |
| $CClF_2$ | Pr-iso |
| $CClF_2$ | $CH_2OMe$ |
| $CClF_2$ | Ph |
| $CF_3CF_2$ | Me |
| $CF_3CF_2$ | Et |
| $CF_3CF_2$ | Pr-iso |
| $CF_3CF_2$ | $CH_2OMe$ |
| $CF_3CF_2$ | Ph |
| $CF_3CF_2CF_2$ | Me |
| $CF_3CF_2CF_2$ | Et |
| $CF_3CF_2CF_2$ | Pr-iso |
| $CF_3CF_2CF_2$ | $CH_2OMe$ |
| $CF_3CF_2CF_2$ | Ph |
| $CH_2OMe$ | Me |
| $CH_2OMe$ | Et |
| $CH_2OMe$ | Pr-iso |
| $CH_2OMe$ | $CH_2OMe$ |
| $CH_2OMe$ | Ph |
| $CH_2SMe$ | Me |
| $CH_2SMe$ | Et |
| $CH_2SMe$ | Pr-iso |
| $CH_2SMe$ | $CH_2OMe$ |
| $CH_2SMe$ | Ph |
| Ph | Me |
| Ph | Et |
| Ph | Pr-iso |
| Ph | $CH_2OMe$ |
| Ph | Ph |
| $OCHF_2$ | Me |
| $OCHF_2$ | Et |
| $OCHF_2$ | Pr-iso |
| $OCHF_2$ | $CH_2OMe$ |
| $OCHF_2$ | Ph |
| Bu-n | Me |
| Bu-iso | Me |
| Bu-sec | Me |
| Bu-tert | Me |
| Pen-n | Me |
| Hex-n | Me |
| Hex-iso | Me |
| Bu-cyc | Me |
| Pen-cyc | Me |
| Hex-cyc | Me |
| $CH_2$Pr-cyc | Me |
| $CH_2$Bu-cyc | Me |
| $CH_2$Pen-cyc | Me |
| $CH_2$Hex-cyc | Me |
| $CH_2CH_2$Pr-cyc | Me |
| $CH_2CH=CH_2$ | Me |
| $CH_2CH=CHMe$ | Me |
| $CH_2CH_2CH=CH_2$ | Me |
| $CH_2C\equiv CH$ | Me |
| $CH_2C\equiv CMe$ | Me |

TABLE 2-continued

| | |
|---|---|
| OEt | Me |
| OPr-n | Me |
| OPr-iso | Me |
| OBu-n | Me |
| OBu-iso | Me |
| OBu-tert | Me |
| OCH$_2$F | Me |
| OCBrF$_2$ | Me |
| OCF$_3$ | Me |
| OCH$_2$CH$_2$Cl | Me |
| OCH$_2$CH$_2$CH$_2$CH$_2$Cl | Me |
| SEt | Me |
| SPr-n | Me |
| SPr-iso | Me |
| SBu-n | Me |
| SBu-iso | Me |
| SBu-tert | Me |
| S(O)Me | Me |
| S(O)Et | Me |
| S(O)Pr-n | Me |
| S(O)Pr-iso | Me |
| S(O)Bu-n | Me |
| SO$_2$Me | Me |
| SO$_2$Et | Me |
| SO$_2$Pr-n | Me |
| SO$_2$Pr-iso | Me |
| SO$_2$Bu-n | Me |
| SO$_2$NMe$_2$ | Me |
| SO$_2$NEt$_2$ | Me |
| SO$_2$N(Pr-n)$_2$ | Me |
| SO$_2$N(Pr-iso)$_2$ | Me |
| SO$_2$N(Bu-n)$_2$ | Me |
| I | Me |
| CN | Me |
| NMe$_2$ | Me |
| NEt$_2$ | Me |
| N(Pr-n)$_2$ | Me |
| N(Pr-iso)$_2$ | Me |
| N(Bu-n)$_2$ | Me |
| CH$_2$Br | Me |
| CH$_2$I | Me |
| CHCl$_2$ | Me |
| CHBr$_2$ | Me |
| CCl$_3$ | Me |
| CBr$_3$ | Me |
| CF$_3$CH$_2$ | Me |
| ClCH$_2$CH$_2$CH$_2$ | Me |
| ClCH$_2$CH$_2$CH$_2$CH$_2$ | Me |
| CH$_2$OEt | Me |
| CH$_2$OPr-n | Me |
| CH$_2$OBu-n | Me |
| CH$_2$OBu-iso | Me |
| CH$_2$OBu-sec | Me |
| CH$_2$OBu-tert | Me |
| CH$_2$CH$_2$OEt | Me |
| CH$_2$CH$_2$OMe | Me |
| CH$_2$CH$_2$OEt | Me |
| CH$_2$CH$_2$OPr-n | Me |
| CH$_2$CH$_2$CH$_2$OMe | Me |
| CH$_2$CH$_2$CH$_2$OEt | Me |
| CH$_2$CH$_2$CH$_2$CH$_2$OMe | Me |
| CH$_2$SEt | Me |
| CH$_2$SPr-n | Me |
| CH$_2$SBu-n | Me |
| CH$_2$CH$_2$CH$_2$CH$_2$SMe | Me |
| CH$_2$S(O)Me | Me |
| CH$_2$S(O)Et | Me |
| CH$_2$S(O)Pr-n | Me |
| CH$_2$S(O)Bu-n | Me |
| CH$_2$CH$_2$CH$_2$CH$_2$S(O)Me | Me |
| CH$_2$SO$_2$Me | Me |
| CH$_2$SO$_2$Et | Me |
| CH$_2$SO$_2$Pr-n | Me |
| CH$_2$SO$_2$Bu-n | Me |
| CH$_2$CH$_2$CH$_2$CH$_2$SO$_2$Me | Me |
| CH$_2$NMe$_2$ | Me |
| CH$_2$NEt$_2$ | Me |
| CH$_2$N(Pr-n)$_2$ | Me |
| CH$_2$N(Pr-iso)$_2$ | Me |

TABLE 2-continued

| | |
|---|---|
| $CH_2N(Bu-n)_2$ | Me |
| $CH_2CH_2CH_2CH_2NMe_2$ | Me |
| 2-Cl—Ph | Me |
| 3-Cl—Ph | Me |
| 4-Cl—Ph | Me |
| 2,4-$Cl_2$—Ph | Me |
| 2-F—Ph | Me |
| 3-F—Ph | Me |
| 4-F—Ph | Me |
| 2-F-4-Cl—Ph | Me |
| 2-Br—Ph | Me |
| 3-Br—Ph | Me |
| 4-Br—Ph | Me |
| 2-Me—Ph | Me |
| 3-Me—Ph | Me |
| 4-Me—Ph | Me |
| 2,4-$Me_2$—Ph | Me |
| 2,6-$Me_2$—Ph | Me |
| 2-MeO—Ph | Me |
| 3-MeO—Ph | Me |
| 4-MeO—Ph | Me |
| 2-$CF_3$—Ph | Me |
| 3-$CF_3$—Ph | Me |
| 4-$CF_3$—Ph | Me |
| $CH_2Ph$ | Me |
| $OCH_2Ph$ | Me |
| $SCH_2Ph$ | Me |
| Cl | Bu-iso |
| Cl | Bu-sec |
| Cl | Bu-tert |
| Cl | $CH_2Bu$-cyc |
| Cl | $CH_2Pen$-cyc |
| Cl | $CH_2Hex$-cyc |
| Cl | $CH_2CH_2Pr$-cyc |
| Cl | $CH_2CH=CHMe$ |
| Cl | $CH_2CH_2CH=CH_2$ |
| Cl | $CH_2C\equiv CMe$ |
| Cl | $CH_2Cl$ |
| Cl | $CH_2Br$ |
| Cl | $CH_2I$ |
| Cl | $CHCl_2$ |
| Cl | $CHBr_2$ |
| Cl | $CCl_3$ |
| Cl | $CBr_3$ |
| Cl | $CClF_2$ |
| Cl | $CF_3CH_2$ |
| Cl | $CF_3CF_2$ |
| Cl | $CF_3CF_2CF_2$ |
| Cl | $ClCH_2CH_2CH_2$ |
| Cl | $ClCH_2CH_2CH_2CH_2$ |
| Cl | $SO_2Et$ |
| Cl | $SO_2Pr$-n |
| Cl | $SO_2Pr$-iso |
| Cl | $SO_2Bu$-n |
| Cl | $SO_2NEt_2$ |
| Cl | $SO_2N(Pr$-n$)_2$ |
| Cl | $SO_2N(Pr$-iso$)_2$ |
| Cl | $SO_2N(Bu$-n$)_2$ |
| Cl | $CH_2OEt$ |
| Cl | $CH_2OPr$-n |
| Cl | $CH_2OBu$-n |
| Cl | $CH_2OBu$-iso |
| Cl | $CH_2OBu$-sec |
| Cl | $CH_2OBu$-tert |
| Cl | $CH_2CH_2OMe$ |
| Cl | $CH_2CH_2OEt$ |
| Cl | $CH_2CH_2OPr$-n |
| Cl | $CH_2CH_2CH_2OMe$ |
| Cl | $CH_2CH_2CH_2OEt$ |
| Cl | $CH_2CH_2CH_2CH_2OMe$ |
| Cl | $CH_2OCH_2CH_2OMe$ |
| Cl | $CH_2OCH_2CH_2OEt$ |
| Cl | $CH_2SEt$ |
| Cl | $CH_2SPr$-n |
| Cl | $CH_2SBu$-n |
| Cl | $CH_2CH_2CH_2CH_2SMe$ |
| Cl | $CH_2S(O)Et$ |
| Cl | $CH_2S(O)Pr$-n |

TABLE 2-continued

| | |
|---|---|
| Cl | $CH_2S(O)Bu-n$ |
| Cl | $CH_2CH_2CH_2CH_2S(O)Me$ |
| Cl | $CH_2SO_2Et$ |
| Cl | $CH_2SO_2Pr-n$ |
| Cl | $CH_2SO_2Bu-n$ |
| Cl | $CH_2CH_2CH_2CH_2SO_2Me$ |
| Cl | $CH_2NEt_2$ |
| Cl | $CH_2N(Pr-n)_2$ |
| Cl | $CH_2N(Pr-iso)_2$ |
| Cl | $CH_2N(Bu-n)_2$ |
| Cl | $CH_2CH_2CH_2CH_2NMe_2$ |
| Cl | 2-Cl—Ph |
| Cl | 3-Cl—Ph |
| Cl | 4-Cl—Ph |
| Cl | $2,4-Cl_2$—Ph |
| Cl | 2-F—Ph |
| Cl | 3-F—Ph |
| Cl | 4-F—Ph |
| Cl | 2-F-4-Cl—Ph |
| Cl | 2-Br—Ph |
| Cl | 3-Br—Ph |
| Cl | 4-Br—Ph |
| Cl | 2-Me—Ph |
| Cl | 3-Me—Ph |
| Cl | 4-Me—Ph |
| Cl | $2,4-Me_2$—Ph |
| Cl | $2,6-Me_2$—Ph |
| Cl | 2-MeO—Ph |
| Cl | 3-MeO—Ph |
| Cl | 4-MeO—Ph |
| Cl | $2-CF_3$—Ph |
| Cl | $3-CF_3$—Ph |
| Cl | $4-CF_3$—Ph |
| Cl | $CH_2Ph$ |
| Br | Bu-n |
| Br | Bu-iso |
| Br | Bu-sec |
| Br | Bu-tert |
| Br | Pen-n |
| Br | Hex-n |
| Br | $CH_2Bu$-cyc |
| Br | $CH_2Pen$-cyc |
| Br | $CH_2Hex$-cyc |
| Br | $CH_2CH_2Pr$-cyc |
| Br | $CH_2CH=CHMe$ |
| Br | $CH_2CH_2CH=CH_2$ |
| Br | $CH_2C\equiv CMe$ |
| Br | $CH_2Cl$ |
| Br | $CH_2Br$ |
| Br | $CH_2I$ |
| Br | $CHCl_2$ |
| Br | $CHBr_2$ |
| Br | $CCl_3$ |
| Br | $CBr_3$ |
| Br | $CClF_2$ |
| Br | $CF_3CH_2$ |
| Br | $CF_3CF_2$ |
| Br | $CF_3CF_2CF_2$ |
| Br | $ClCH_2CH_2CH_2$ |
| Br | $ClCH_2CH_2CH_2CH_2$ |
| Br | $SO_2Et$ |
| Br | $SO_2Pr-n$ |
| Br | $SO_2Pr$-iso |
| Br | $SO_2Bu-n$ |
| Br | $SO_2NEt_2$ |
| Br | $SO_2N(Pr-n)_2$ |
| Br | $SO_2N(Pr-iso)_2$ |
| Br | $SO_2N(Bu-n)_2$ |
| Br | $CH_2OEt$ |
| Br | $CH_2OPr-n$ |
| Br | $CH_2OBu-n$ |
| Br | $CH_2OBu$-iso |
| Br | $CH_2OBu$-sec |
| Br | $CH_2OBu$-tert |
| Br | $CH_2CH_2OMe$ |
| Br | $CH_2CH_2OEt$ |
| Br | $CH_2CH_2OPr-n$ |
| Br | $CH_2CH_2CH_2OMe$ |

TABLE 2-continued

| | |
|---|---|
| Br | $CH_2CH_2CH_2OEt$ |
| Br | $CH_2CH_2CH_2CH_2OMe$ |
| Br | $CH_2SEt$ |
| Br | $CH_2SPr\text{-}n$ |
| Br | $CH_2SBu\text{-}n$ |
| Br | $CH_2CH_2CH_2CH_2SMe$ |
| Br | $CH_2S(O)Et$ |
| Br | $CH_2S(O)Pr\text{-}n$ |
| Br | $CH_2S(O)Bu\text{-}n$ |
| Br | $CH_2CH_2CH_2CH_2S(O)Me$ |
| Br | $CH_2SO_2Et$ |
| Br | $CH_2SO_2Pr\text{-}n$ |
| Br | $CH_2SO_2Bu\text{-}n$ |
| Br | $CH_2CH_2CH_2CH_2SO_2Me$ |
| Br | $CH_2NEt_2$ |
| Br | $CH_2N(Pr\text{-}n)_2$ |
| Br | $CH_2N(Pr\text{-}iso)_2$ |
| Br | $CH_2N(Bu\text{-}n)_2$ |
| Br | $CH_2CH_2CH_2CH_2NMe_2$ |
| Br | 2-Cl—Ph |
| Br | 3-Cl—Ph |
| Br | 4-Cl—Ph |
| Br | 2,4-$Cl_2$—Ph |
| Br | 2-F—Ph |
| Br | 3-F—Ph |
| Br | 4-F—Ph |
| Br | 2-F-4-Cl—Ph |
| Br | 2-Br—Ph |
| Br | 3-Br—Ph |
| Br | 4-Br—Ph |
| Br | 2-Me—Ph |
| Br | 3-Me—Ph |
| Br | 4-Me—Ph |
| Br | 2,4-$Me_2$—Ph |
| Br | 2,6-$Me_2$—Ph |
| Br | 2-MeO—Ph |
| Br | 3-MeO—Ph |
| Br | 4-MeO—Ph |
| Br | 2-$CF_3$—Ph |
| Br | 3-$CF_3$—Ph |
| Br | 4-$CF_3$—Ph |
| Br | $CH_2Ph$ |
| Cl | $CO_2Et$ |
| Cl | $CO_2Pr\text{-}n$ |
| Cl | $CO_2Pr\text{-}iso$ |
| Cl | $CO_2Bu\text{-}n$ |
| Cl | COEt |
| Cl | $COPr\text{-}n$ |
| Cl | $COPr\text{-}iso$ |
| Cl | $COBu\text{-}n$ |
| Cl | CONHEt |
| Cl | $CONHPr\text{-}n$ |
| Cl | $CONHPr\text{-}iso$ |
| Cl | $CONHBu\text{-}n$ |
| Cl | $CONEt_2$ |
| Cl | $CON(Pr\text{-}n)_2$ |
| Cl | $CON(Pr\text{-}iso)_2$ |
| Cl | $CON(Bu\text{-}n)_2$ |
| Cl | $CH_2CO_2Et$ |
| Cl | $CH_2CO_2Pr\text{-}n$ |
| Cl | $CH_2CO_2Pr\text{-}iso$ |
| Cl | $CH_2CO_2Bu\text{-}n$ |
| Cl | $CHMeCO_2Pr\text{-}n$ |
| Cl | $CH_2CH_2CH_2CO_2Me$ |
| Cl | $CH_2COEt$ |
| Cl | $CH_2COPr\text{-}n$ |
| Cl | $CH_2COPr\text{-}iso$ |
| Cl | $CH_2COBu\text{-}n$ |
| Cl | CHMeCOMe |
| Cl | CHMeCOEt |
| Cl | $CHMeCOPr\text{-}n$ |
| Cl | $CH_2CH_2CH_2COMe$ |
| Br | $CO_2Et$ |
| Br | $CO_2Pr\text{-}n$ |
| Br | $CO_2Pr\text{-}iso$ |
| Br | $CO_2Bu\text{-}n$ |
| Br | COEt |
| Br | $COPr\text{-}n$ |
| Br | $COPr\text{-}iso$ |

TABLE 2-continued

| | |
|---|---|
| Br | COBu-n |
| Br | CONHEt |
| Br | CONHPr-n |
| Br | CONHPr-iso |
| Br | CONHBu-n |
| Br | CONEt$_2$ |
| Br | CON(Pr-n)$_2$ |
| Br | CON(Pr-iso)$_2$ |
| Br | CON(Bu-n)$_2$ |
| Br | CH$_2$CO$_2$Et |
| Br | CH$_2$CO$_2$Pr-n |
| Br | CH$_2$CO$_2$Pr-iso |
| Br | CH$_2$CO$_2$Bu-n |
| Br | CHMeCO$_2$Pr-n |
| Br | CH$_2$CH$_2$CH$_2$CO$_2$Me |
| Br | CH$_2$COEt |
| Br | CH$_2$COPr-n |
| Br | CH$_2$COPr-iso |
| Br | CH$_2$COBu-n |
| Br | CHMeCOMe |
| Br | CHMeCOEt |
| Br | CHMeCOPr-n |
| Br | CH$_2$CH$_2$CH$_2$COMe |
| H | 2-Cl—Ph |
| H | 3-Cl—Ph |
| H | 4-Cl—Ph |
| H | 2,4-Cl$_2$—Ph |
| H | 2-F—Ph |
| H | 3-F—Ph |
| H | 4-F—Ph |
| H | 2-F-4-Cl—Ph |
| H | 2-Br—Ph |
| H | 3-Br—Ph |
| H | 4-Br—Ph |
| H | 2-Me—Ph |
| H | 3-Me—Ph |
| H | 4-Me—Ph |
| H | 2,4-Me$_2$—Ph |
| H | 2,6-Me$_2$—Ph |
| H | 2-MeO—Ph |
| H | 3-MeO—Ph |
| H | 4-MeO—Ph |
| H | 2-CF$_3$—Ph |
| H | 3-CF$_3$—Ph |
| H | 4-CF$_3$—Ph |
| H | CH$_2$Ph |
| Me | 2-Cl—Ph |
| Me | 3-Cl—Ph |
| Me | 4-Cl—Ph |
| Me | 2,4-Cl$_2$—Ph |
| Me | 2-F—Ph |
| Me | 3-F—Ph |
| Me | 4-F—Ph |
| Me | 2-F-4-Cl—Ph |
| Me | 2-Br—Ph |
| Me | 3-Br—Ph |
| Me | 4-Br—Ph |
| Me | 2-Me—Ph |
| Me | 3-Me—Ph |
| Me | 4-Me—Ph |
| Me | 2,4-Me$_2$—Ph |
| Me | 2,6-Me$_2$—Ph |
| Me | 2-MeO—Ph |
| Me | 3-MeO—Ph |
| Me | 4-MeO—Ph |
| Me | 2-CF$_3$—Ph |
| Me | 3-CF$_3$—Ph |
| Me | 4-CF$_3$—Ph |
| Me | CH$_2$Ph |
| CF$_3$ | 2-Cl—Ph |
| CF$_3$ | 3-Cl—Ph |
| CF$_3$ | 4-Cl—Ph |
| CF$_3$ | 2,4-Cl$_2$—Ph |
| CF$_3$ | 2-F—Ph |
| CF$_3$ | 3-F—Ph |
| CF$_3$ | 4-F—Ph |
| CF$_3$ | 2-F-4-Cl—Ph |
| CF$_3$ | 2-Br—Ph |
| CF$_3$ | 3-Br—Ph |

TABLE 2-continued

| | |
|---|---|
| $CF_3$ | 4-Br—Ph |
| $CF_3$ | 2-Me—Ph |
| $CF_3$ | 3-Me—Ph |
| $CF_3$ | 4-Me—Ph |
| $CF_3$ | 2,4-Me$_2$—Ph |
| $CF_3$ | 2,6-Me$_2$—Ph |
| $CF_3$ | 2-MeO—Ph |
| $CF_3$ | 3-MeO—Ph |
| $CF_3$ | 4-MeO—Ph |
| $CF_3$ | 2-CF$_3$—Ph |
| $CF_3$ | 3-CF$_3$—Ph |
| $CF_3$ | 4-CF$_3$—Ph |
| $CF_3$ | CH$_2$Ph |
| 3,5-Cl$_2$—Ph | Me |
| 2,6-Cl$_2$—Ph | Me |
| 2,3-Cl$_2$—Ph | Me |
| 2,4,6-Cl$_3$—Ph | Me |
| 2,3,5-Cl$_3$—Ph | Me |
| 2,3,4-Cl$_3$—Ph | Me |
| 2-NO$_2$—Ph | Me |
| 2-CN—Ph | Me |
| H | Pr-cyc |
| H | Bu-cyc |
| H | Pen-cyc |
| H | Hex-cyc |
| H | 3,5-Cl$_2$—Ph |
| H | 2,6-Cl$_2$—Ph |
| H | 2,3-Cl$_2$—Ph |
| H | 2,4,6-Cl$_3$—Ph |
| H | 2,3,5-Cl$_3$—Ph |
| H | 2,3,4-Cl$_3$—Ph |
| H | 2-NO$_2$—Ph |
| H | 2-CN—Ph |
| H | 2-Cl-4-CF$_3$—Ph |
| H | 2,6-Cl$_2$-4-CF$_3$—Ph |
| H | 2,5-Cl$_2$—Ph |
| H | 3,4-Cl$_2$—Ph |
| H | 2,4-(NO$_2$)$_2$—Ph |
| H | 3-NO$_2$—Ph |
| H | 4-NO$_2$—Ph |
| H | 2-Py |
| H | 3-Py |
| H | 4-Py |
| H | 3-Cl-2-Py |
| H | 4-Cl-2-Py |
| H | 5-Cl-2-Py |
| H | 6-Cl-2-Py |
| H | 3-F-2-Py |
| H | 4-F-2-Py |
| H | 5-F-2-Py |
| H | 6-F-2-Py |
| H | 3-Br-2-Py |
| H | 4-Br-2-Py |
| H | 5-Br-2-Py |
| H | 6-Br-2-Py |
| H | 3-CF$_3$-2-Py |
| H | 4-CF$_3$-2-Py |
| H | 5-CF$_3$-2-Py |
| H | 6-CF$_3$-2-Py |
| H | 3-Cl-5-CF$_3$-2-Py |
| H | 3-Me-2-Py |
| H | 4-Me-2-Py |
| H | 5-Me-2-Py |
| H | 6-Me-2-Py |
| H | 3-NO$_2$-2-Py |
| H | 4-NO$_2$-2-Py |
| H | 5-NO$_2$-2-Py |
| H | 6-NO$_2$-2-Py |
| Me | Pr-cyc |
| Me | Bu-cyc |
| Me | Pen-cyc |
| Me | Hex-cyc |
| Me | 3,5-Cl$_2$—Ph |
| Me | 2,6-Cl$_2$—Ph |
| Me | 2,3-Cl$_2$—Ph |
| Me | 2,4,6-Cl$_3$—Ph |
| Me | 2,3,5-Cl$_3$—Ph |
| Me | 2,3,4-Cl$_3$—Ph |
| Me | 2-NO$_2$—Ph |

TABLE 2-continued

| | |
|---|---|
| Me | 2-CN—Ph |
| Me | 2-Cl-4-CF$_3$—Ph |
| Me | 2,6-Cl$_2$-4-CF$_3$—Ph |
| Me | 2,5-Cl$_2$—Ph |
| Me | 3,4-Cl$_2$—Ph |
| Me | 2,4-(NO$_2$)$_2$—Ph |
| Me | 3-NO$_2$—Ph |
| Me | 4-NO$_2$—Ph |
| Me | 2-Py |
| Me | 3-Py |
| Me | 4-Py |
| Me | 3-Cl-2-Py |
| Me | 4-Cl-2-Py |
| Me | 5-Cl-2-Py |
| Me | 6-Cl-2-Py |
| Me | 3-F-2-Py |
| Me | 4-F-2-Py |
| Me | 5-F-2-Py |
| Me | 6-F-2-Py |
| Me | 3-Br-2-Py |
| Me | 4-Br-2-Py |
| Me | 5-Br-2-Py |
| Me | 6-Br-2-Py |
| Me | 3-CF$_3$-2-Py |
| Me | 4-CF$_3$-2-Py |
| Me | 5-CF$_3$-2-Py |
| Me | 6-CF$_3$-2-Py |
| Me | 3-Cl-5-CF$_3$-2-Py |
| Me | 3-Me-2-Py |
| Me | 4-Me-2-Py |
| Me | 5-Me-2-Py |
| Me | 6-Me-2-Py |
| Me | 3-NO$_2$-2-Py |
| Me | 4-NO$_2$-2-Py |
| Me | 5-NO$_2$-2-Py |
| Me | 6-NO$_2$-2-Py |
| Cl | Pr-cyc |
| Cl | Bu-cyc |
| Cl | Pen-cyc |
| Cl | Hex-cyc |
| Cl | 3,5-Cl$_2$—Ph |
| Cl | 2,6-Cl$_2$—Ph |
| Cl | 2,3-Cl$_2$—Ph |
| Cl | 2,4,6-Cl$_3$—Ph |
| Cl | 2,3,5-Cl$_3$—Ph |
| Cl | 2,3,4-Cl$_3$—Ph |
| Cl | 2-NO$_2$—Ph |
| Cl | 2-CN—Ph |
| Cl | 2-Cl-4-CF$_3$—Ph |
| Cl | 2,6-Cl$_2$-4-CF$_3$—Ph |
| Cl | 2,5-Cl$_2$—Ph |
| Cl | 3,4-Cl$_2$—Ph |
| Cl | 2,4-(NO$_2$)$_2$—Ph |
| Cl | 3-NO$_2$—Ph |
| Cl | 4-NO$_2$—Ph |
| Cl | 2-Py |
| Cl | 3-Py |
| Cl | 4-Py |
| Cl | 3-Cl-2-Py |
| Cl | 4-Cl-2-Py |
| Cl | 5-Cl-2-Py |
| Cl | 6-Cl-2-Py |
| Cl | 3-F-2-Py |
| Cl | 4-F-2-Py |
| Cl | 5-F-2-Py |
| Cl | 6-F-2-Py |
| Cl | 3-Br-2-Py |
| Cl | 4-Br-2-Py |
| Cl | 5-Br-2-Py |
| Cl | 6-Br-2-Py |
| Cl | 3-CF$_3$-2-Py |
| Cl | 4-CF$_3$-2-Py |
| Cl | 5-CF$_3$-2-Py |
| Cl | 6-CF$_3$-2-Py |
| Cl | 3-Cl-5-CF$_3$-2-Py |
| Cl | 3-Me-2-Py |
| Cl | 4-Me-2-Py |
| Cl | 5-Me-2-Py |
| Cl | 6-Me-2-Py |

TABLE 2-continued

| | |
|---|---|
| Cl | 3-NO$_2$-2-Py |
| Cl | 4-NO$_2$-2-Py |
| Cl | 5-NO$_2$-2-Py |
| Cl | 6-NO$_2$-2-Py |
| Br | Pr-cyc |
| Br | Bu-cyc |
| Br | Pen-cyc |
| Br | Hex-cyc |
| Br | 3,5-Cl$_2$—Ph |
| Br | 2,6-Cl$_2$—Ph |
| Br | 2,3-Cl$_2$—Ph |
| Br | 2,4,6-Cl$_3$—Ph |
| Br | 2,3,5-Cl$_3$—Ph |
| Br | 2,3,4-Cl$_3$—Ph |
| Br | 2-NO$_2$—Ph |
| Br | 2-CN—Ph |
| Br | 2-Cl-4-CF$_3$—Ph |
| Br | 2,6-Cl$_2$-4-CF$_3$—Ph |
| Br | 2,5-Cl$_2$—Ph |
| Br | 3,4-Cl$_2$—Ph |
| Br | 2,4-(NO$_2$)$_2$—Ph |
| Br | 3-NO$_2$—Ph |
| Br | 4-NO$_2$—Ph |
| Br | 2-Py |
| Br | 3-Py |
| Br | 4-Py |
| Br | 3-Cl-2-Py |
| Br | 4-Cl-2-Py |
| Br | 5-Cl-2-Py |
| Br | 6-Cl-2-Py |
| Br | 3-F-2-Py |
| Br | 4-F-2-Py |
| Br | 5-F-2-Py |
| Br | 6-F-2-Py |
| Br | 3-Br-2-Py |
| Br | 4-Br-2-Py |
| Br | 5-Br-2-Py |
| Br | 6-Br-2-Py |
| Br | 3-CF$_3$-2-Py |
| Br | 4-CF$_3$-2-Py |
| Br | 5-CF$_3$-2-Py |
| Br | 6-CF$_3$-2-Py |
| Br | 3-Cl-5-CF$_3$-2-Py |
| Br | 3-Me-2-Py |
| Br | 4-Me-2-Py |
| Br | 5-Me-2-Py |
| Br | 6-Me-2-Py |
| Br | 3-NO$_2$-2-Py |
| Br | 4-NO$_2$-2-Py |
| Br | 5-NO$_2$-2-Py |
| Br | 6-NO$_2$-2-Py |
| CF$_3$ | Pr-cyc |
| CF$_3$ | Bu-cyc |
| CF$_3$ | Pen-cyc |
| CF$_3$ | Hex-cyc |
| CF$_3$ | 3,5-Cl$_2$—Ph |
| CF$_3$ | 2,6-Cl$_2$—Ph |
| CF$_3$ | 2,3-Cl$_2$—Ph |
| CF$_3$ | 2,4,6-Cl$_3$—Ph |
| CF$_3$ | 2,3,5-Cl$_3$—Ph |
| CF$_3$ | 2,3,4-Cl$_3$—Ph |
| CF$_3$ | 2-NO$_2$—Ph |
| CF$_3$ | 2-CN—Ph |
| CF$_3$ | 3-CN—Ph |
| CF$_3$ | 4-CN—Ph |
| CF$_3$ | CHMePh |
| CF$_3$ | CMe$_2$Ph |
| CF$_3$ | 2-Cl-4-CF$_3$—Ph |
| CF$_3$ | 2,6-Cl$_2$-4-CF$_3$—Ph |
| CF$_3$ | 2,5-Cl$_2$—Ph |
| CF$_3$ | 3,4-Cl$_2$—Ph |
| CF$_3$ | 2,4-(NO$_2$)$_2$—Ph |
| CF$_3$ | 3-NO$_2$—Ph |
| CF$_3$ | 4-NO$_2$—Ph |
| CF$_3$ | 2-Py |
| CF$_3$ | 3-Py |
| CF$_3$ | 4-Py |
| CF$_3$ | 3-Cl-2-Py |
| CF$_3$ | 4-Cl-2-Py |

TABLE 2-continued

| | |
|---|---|
| $CF_3$ | 5-Cl-2-Py |
| $CF_3$ | 6-Cl-2-Py |
| $CF_3$ | 3-F-2-Py |
| $CF_3$ | 4-F-2-Py |
| $CF_3$ | 5-F-2-Py |
| $CF_3$ | 6-F-2-Py |
| $CF_3$ | 3-Br-2-Py |
| $CF_3$ | 4-Br-2-Py |
| $CF_3$ | 5-Br-2-Py |
| $CF_3$ | 6-Br-2-Py |
| $CF_3$ | 3-$CF_3$-2-Py |
| $CF_3$ | 4-$CF_3$-2-Py |
| $CF_3$ | 5-$CF_3$-2-Py |
| $CF_3$ | 6-$CF_3$-2-Py |
| $CF_3$ | 3-Cl-5-$CF_3$-2-Py |
| $CF_3$ | 3-Me-2-Py |
| $CF_3$ | 4-Me-2-Py |
| $CF_3$ | 5-Me-2-Py |
| $CF_3$ | 6-Me-2-Py |
| $CF_3$ | 3-$NO_2$-2-Py |
| $CF_3$ | 4-$NO_2$-2-Py |
| $CF_3$ | 5-$NO_2$-2-Py |
| $CF_3$ | 6-$NO_2$-2-Py |
| Bu-n | Ph |
| Bu-iso | Ph |
| Bu-sec | Ph |
| Bu-tert | Ph |
| Pen-n | Ph |
| Hex-n | Ph |
| Hex-iso | Ph |
| Bu-cyc | Ph |
| Pen-cyc | Ph |
| Hex-cyc | Ph |
| $CH_2$Pr-cyc | Ph |
| $CH_2$Bu-cyc | Ph |
| $CH_2$Pen-cyc | Ph |
| $CH_2$Hex-cyc | Ph |
| $CH_2CH_2$Pr-cyc | Ph |
| $CH_2CH=CH_2$ | Ph |
| $CH_2CH=CHPh$ | Ph |
| $CH_2CH_2CH=CH_2$ | Ph |
| $CH_2C\equiv CH$ | Ph |
| $CH_2C\equiv CMe$ | Ph |
| OEt | Ph |
| OPr-n | Ph |
| OPr-iso | Ph |
| OBu-n | Ph |
| OBu-iso | Ph |
| OBu-tert | Ph |
| $OCH_2F$ | Ph |
| $OCBrF_2$ | Ph |
| $OCF_3$ | Ph |
| $OCH_2CH_2Cl$ | Ph |
| $OCH_2CH_2CH_2CH_2Cl$ | Ph |
| SEt | Ph |
| SPr-n | Ph |
| SPr-iso | Ph |
| SBu-n | Ph |
| SBu-iso | Ph |
| SBu-tert | Ph |
| S(O)Me | Ph |
| S(O)Et | Ph |
| S(O)Pr-n | Ph |
| S(O)Pr-iso | Ph |
| S(O)Bu-n | Ph |
| $SO_2$Me | Ph |
| $SO_2$Et | Ph |
| $SO_2$Pr-n | Ph |
| $SO_2$Pr-iso | Ph |
| $SO_2$Bu-n | Ph |
| $SO_2NMe_2$ | Ph |
| $SO_2NEt_2$ | Ph |
| $SO_2N(Pr-n)_2$ | Ph |
| $SO_2N(Pr-iso)_2$ | Ph |
| $SO_2N(Bu-n)_2$ | Ph |
| I | Ph |
| CN | Ph |

TABLE 2-continued

| | |
|---|---|
| NMe₂ | Ph |
| NEt₂ | Ph |
| N(Pr-n)₂ | Ph |
| N(Pr-iso)₂ | Ph |
| N(Bu-n)₂ | Ph |
| CH₂Br | Ph |
| CH₂I | Ph |
| CHCl₂ | Ph |
| CHBr₂ | Ph |
| CCl₃ | Ph |
| CBr₃ | Ph |
| CF₃CH₂ | Ph |
| ClCH₂CH₂CH₂ | Ph |
| ClCH₂CH₂CH₂CH₂ | Ph |
| CH₂OEt | Ph |
| CH₂OPr-n | Ph |
| CH₂OBu-n | Ph |
| CH₂OBu-iso | Ph |
| CH₂OBu-sec | Ph |
| CH₂OBu-tert | Ph |
| CH₂CH₂OEt | Ph |
| CH₂CH₂OMe | Ph |
| CH₂CH₂OEt | Ph |
| CH₂CH₂OPr-n | Ph |
| CH₂CH₂CH₂OMe | Ph |
| CH₂CH₂CH₂OEt | Ph |
| CH₂CH₂CH₂CH₂OMe | Ph |
| CH₂SEt | Ph |
| CH₂SPr-n | Ph |
| CH₂SBu-n | Ph |
| CH₂CH₂CH₂CH₂SMe | Ph |
| CH₂S(O)Me | Ph |
| CH₂S(O)Et | Ph |
| CH₂S(O)Pr-n | Ph |
| CH₂S(O)Bu-n | Ph |
| CH₂CH₂CH₂CH₂S(O)Me | Ph |
| CH₂SO₂Me | Ph |
| CH₂SO₂Et | Ph |
| CH₂SO₂Pr-n | Ph |
| CH₂SO₂Bu-n | Ph |
| CH₂CH₂CH₂CH₂SO₂Me | Ph |
| CH₂NMe₂ | Ph |
| CH₂NEt₂ | Ph |
| CH₂N(Pr-n)₂ | Ph |
| CH₂N(Pr-iso)₂ | Ph |
| CH₂N(Bu-n)₂ | Ph |
| CH₂CH₂CH₂CH₂NMe₂ | Ph |
| 2-Cl—Ph | Ph |
| 3-Cl—Ph | Ph |
| 4-Cl—Ph | Ph |
| 2,4-Cl₂—Ph | Ph |
| 2-F—Ph | Ph |
| 3-F—Ph | Ph |
| 4-F—Ph | Ph |
| 2-F-4-Cl—Ph | Ph |
| 2-Br—Ph | Ph |
| 3-Br—Ph | Ph |
| 4-Br—Ph | Ph |
| 2-Me—Ph | Ph |
| 3-Me—Ph | Ph |
| 4-Me—Ph | Ph |
| 2,4-Me₂—Ph | Ph |
| 2,6-Me₂—Ph | Ph |
| 2-MeO—Ph | Ph |
| 3-MeO—Ph | Ph |
| 4-MeO—Ph | Ph |
| 2-CF₃—Ph | Ph |
| 3-CF₃—Ph | Ph |
| 4-CF₃—Ph | Ph |
| CH₂Ph | Ph |
| OCH₂Ph | Ph |
| SCH₂Ph | Ph |
| Bu-n | 2-Py |
| Bu-iso | 2-Py |
| Bu-sec | 2-Py |
| Bu-tert | 2-Py |
| Pen-n | 2-Py |
| Hex-n | 2-Py |
| Hex-iso | 2-Py |

TABLE 2-continued

| | |
|---|---|
| Bu-cyc | 2-Py |
| Pen-cyc | 2-Py |
| Hex-cyc | 2-Py |
| $CH_2Pr$-cyc | 2-Py |
| $CH_2Bu$-cyc | 2-Py |
| $CH_2Pen$-cyc | 2-Py |
| $CH_2Hex$-cyc | 2-Py |
| $CH_2CH_2Pr$-cyc | 2-Py |
| $CH_2CH=CH_2$ | 2-Py |
| $CH_2CH=CHMe$ | 2-Py |
| $CH_2CH_2CH=CH_2$ | 2-Py |
| $CH_2C\equiv CH$ | 2-Py |
| $CH_2C\equiv CMe$ | 2-Py |
| OEt | 2-Py |
| OPr-n | 2-Py |
| OPr-iso | 2-Py |
| OBu-n | 2-Py |
| OBu-iso | 2-Py |
| OBu-tert | 2-Py |
| $OCH_2F$ | 2-Py |
| $OCBrF_2$ | 2-Py |
| $OCF_3$ | 2-Py |
| $OCH_2CH_2Cl$ | 2-Py |
| $OCH_2CH_2CH_2CH_2Cl$ | 2-Py |
| SEt | 2-Py |
| SPr-n | 2-Py |
| SPr-iso | 2-Py |
| SBu-n | 2-Py |
| SBu-iso | 2-Py |
| SBu-tert | 2-Py |
| S(O)Me | 2-Py |
| S(O)Et | 2-Py |
| S(O)Pr-n | 2-Py |
| S(O)Pr-iso | 2-Py |
| S(O)Bu-n | 2-Py |
| $SO_2Me$ | 2-Py |
| $SO_2Et$ | 2-Py |
| $SO_2Pr$-n | 2-Py |
| $SO_2Pr$-iso | 2-Py |
| $SO_2Bu$-n | 2-Py |
| $SO_2NMe_2$ | 2-Py |
| $SO_2NEt_2$ | 2-Py |
| $SO_2N(Pr$-n$)_2$ | 2-Py |
| $SO_2N(Pr$-iso$)_2$ | 2-Py |
| $SO_2N(Bu$-n$)_2$ | 2-Py |
| I | 2-Py |
| CN | 2-Py |
| $NMe_2$ | 2-Py |
| $NEt_2$ | 2-Py |
| $N(Pr$-n$)_2$ | 2-Py |
| $N(Pr$-iso$)_2$ | 2-Py |
| $N(Bu$-n$)_2$ | 2-Py |
| $CH_2Br$ | 2-Py |
| $CH_2I$ | 2-Py |
| $CHCl_2$ | 2-Py |
| $CHBr_2$ | 2-Py |
| $CCl_3$ | 2-Py |
| $CBr_3$ | 2-Py |
| $CF_3CH_2$ | 2-Py |
| $ClCH_2CH_2CH_2$ | 2-Py |
| $ClCH_2CH_2CH_2CH_2$ | 2-Py |
| $CH_2OEt$ | 2-Py |
| $CH_2OPr$-n | 2-Py |
| $CH_2OBu$-n | 2-Py |
| $CH_2OBu$-iso | 2-Py |
| $CH_2OBu$-sec | 2-Py |
| $CH_2OBu$-tert | 2-Py |
| $CH_2CH_2OEt$ | 2-Py |
| $CH_2CH_2OMe$ | 2-Py |
| $CH_2CH_2OEt$ | 2-Py |
| $CH_2CH_2OPr$-n | 2-Py |
| $CH_2CH_2CH_2OMe$ | 2-Py |
| $CH_2CH_2CH_2OEt$ | 2-Py |
| $CH_2CH_2CH_2CH_2OMe$ | 2-Py |
| $CH_2SEt$ | 2-Py |
| $CH_2SPr$-n | 2-Py |
| $CH_2SBu$-n | 2-Py |

TABLE 2-continued

| | |
|---|---|
| CH$_2$CH$_2$CH$_2$CH$_2$SMe | 2-Py |
| CH$_2$S(O)Me | 2-Py |
| CH$_2$S(O)Et | 2-Py |
| CH$_2$S(O)Pr-n | 2-Py |
| CH$_2$S(O)Bu-n | 2-Py |
| CH$_2$CH$_2$CH$_2$CH$_2$S(O)Me | 2-Py |
| CH$_2$SO$_2$Me | 2-Py |
| CH$_2$SO$_2$Et | 2-Py |
| CH$_2$SO$_2$Pr-n | 2-Py |
| CH$_2$SO$_2$Bu-n | 2-Py |
| CH$_2$CH$_2$CH$_2$CH$_2$SO$_2$Me | 2-Py |
| CH$_2$NMe$_2$ | 2-Py |
| CH$_2$NEt$_2$ | 2-Py |
| CH$_2$N(Pr-n)$_2$ | 2-Py |
| CH$_2$N(Pr-iso)$_2$ | 2-Py |
| CH$_2$N(Bu-n)$_2$ | 2-Py |
| CH$_2$CH$_2$CH$_2$CH$_2$NMe$_2$ | 2-Py |
| 2-Cl—Ph | 2-Py |
| 3-Cl—Ph | 2-Py |
| 4-Cl—Ph | 2-Py |
| 2,4-Cl$_2$—Ph | 2-Py |
| 2-F—Ph | 2-Py |
| 3-F—Ph | 2-Py |
| 4-F—Ph | 2-Py |
| 2-F-4-Cl—Ph | 2-Py |
| 2-Br—Ph | 2-Py |
| 3-Br—Ph | 2-Py |
| 4-Br—Ph | 2-Py |
| 2-Me—Ph | 2-Py |
| 3-Me—Ph | 2-Py |
| 4-Me—Ph | 2-Py |
| 2,4-Me$_2$—Ph | 2-Py |
| 2,6-Me$_2$—Ph | 2-Py |
| 2-MeO—Ph | 2-Py |
| 3-MeO—Ph | 2-Py |
| 4-MeO—Ph | 2-Py |
| 2-CF$_3$—Ph | 2-Py |
| 3-CF$_3$—Ph | 2-Py |
| 4-CF$_3$—Ph | 2-Py |
| CH$_2$Ph | 2-Py |
| OCH$_2$Ph | 2-Py |
| SCH$_2$Ph | 2-Py |
| Cl | Bu-tert |
| Cl | Bu-iso |
| Cl | Bu-sec |
| Cl | 3-CN—Ph |
| Cl | 4-CN—Ph |
| Cl | CHMePh |
| Cl | CMe$_2$Ph |
| Br | 3-CN—Ph |
| Br | 4-CN—Ph |
| Br | CHMePh |
| Br | CMe$_2$Ph |
| CF$_3$ | Bu-iso |
| CF$_3$ | Bu-sec |
| CF$_3$ | CH$_2$Bu-cyc |
| CF$_3$ | CH$_2$Pen-cyc |
| CF$_3$ | CH$_2$Hex-cyc |
| CF$_3$ | CH$_2$CH$_2$Pr-cyc |
| CF$_3$ | CH$_2$CH=CHMe |
| CF$_3$ | CH$_2$CH$_2$CH=CH$_2$ |
| CF$_3$ | CH$_2$C≡CMe |
| CF$_3$ | CH$_2$Cl |
| CF$_3$ | CH$_2$Br |
| CF$_3$ | CH$_2$I |
| CF$_3$ | CHCl$_2$ |
| CF$_3$ | CHBr$_2$ |
| CF$_3$ | CCl$_3$ |
| CF$_3$ | CBr$_3$ |
| CF$_3$ | CClF$_2$ |
| CF$_3$ | CF$_3$CH$_2$ |
| CF$_3$ | CF$_3$CF$_2$ |
| CF$_3$ | CF$_3$CF$_2$CF$_2$ |
| CF$_3$ | ClCH$_2$CH$_2$CH$_2$ |
| CF$_3$ | ClCH$_2$CH$_2$CH$_2$CH$_2$ |
| CF$_3$ | SO$_2$Et |
| CF$_3$ | SO$_2$Pr-n |
| CF$_3$ | SO$_2$Pr-iso |

TABLE 2-continued

| | |
|---|---|
| $CF_3$ | $SO_2Bu$-n |
| $CF_3$ | $SO_2NEt_2$ |
| $CF_3$ | $SO_2N(Pr$-n$)_2$ |
| $CF_3$ | $SO_2N(Pr$-iso$)_2$ |
| $CF_3$ | $SO_2N(Bu$-n$)_2$ |
| $CF_3$ | $CH_2OEt$ |
| $CF_3$ | $CH_2OPr$-n |
| $CF_3$ | $CH_2OBu$-n |
| $CF_3$ | $CH_2OBu$-iso |
| $CF_3$ | $CH_2OBu$-sec |
| $CF_3$ | $CH_2OBu$-tert |
| $CF_3$ | $CH_2CH_2OMe$ |
| $CF_3$ | $CH_2CH_2OEt$ |
| $CF_3$ | $CH_2CH_2OPr$-n |
| $CF_3$ | $CH_2CH_2CH_2OMe$ |
| $CF_3$ | $CH_2CH_2CH_2OEt$ |
| $CF_3$ | $CH_2CH_2CH_2CH_2OMe$ |
| $CF_3$ | $CH_2OCH_2CH_2OMe$ |
| $CF_3$ | $CH_2OCH_2CH_2OEt$ |
| $CF_3$ | $CH_2SEt$ |
| $CF_3$ | $CH_2SPr$-n |
| $CF_3$ | $CH_2SBu$-n |
| $CF_3$ | $CH_2CH_2CH_2CH_2SMe$ |
| $CF_3$ | $CH_2S(O)Et$ |
| $CF_3$ | $CH_2S(O)Pr$-n |
| $CF_3$ | $CH_2S(O)Bu$-n |
| $CF_3$ | $CH_2CH_2CH_2CH_2S(O)Me$ |
| $CF_3$ | $CH_2SO_2Et$ |
| $CF_3$ | $CH_2SO_2Pr$-n |
| $CF_3$ | $CH_2SO_2Bu$-n |
| $CF_3$ | $CH_2CH_2CH_2CH_2SO_2Me$ |
| $CF_3$ | $CH_2NEt_2$ |
| $CF_3$ | $CH_2N(Pr$-n$)_2$ |
| $CF_3$ | $CH_2N(Pr$-iso$)_2$ |
| $CF_3$ | $CH_2N(Bu$-n$)_2$ |
| $CF_3$ | $CH_2CH_2CH_2CH_2NMe_2$ |
| $CF_3$ | $CO_2Et$ |
| $CF_3$ | $CO_2Pr$-n |
| $CF_3$ | $CO_2Pr$-iso |
| $CF_3$ | $CO_2Bu$-n |
| $CF_3$ | $COEt$ |
| $CF_3$ | $COPr$-n |
| $CF_3$ | $COPr$-iso |
| $CF_3$ | $COBu$-n |
| $CF_3$ | $CONHEt$ |
| $CF_3$ | $CONHPr$-n |
| $CF_3$ | $CONHPr$-iso |
| $CF_3$ | $CONHBu$-n |
| $CF_3$ | $CONEt_2$ |
| $CF_3$ | $CON(Pr$-n$)_2$ |
| $CF_3$ | $CON(Pr$-iso$)_2$ |
| $CF_3$ | $CON(Bu$-n$)_2$ |
| $CF_3$ | $CH_2CO_2Et$ |
| $CF_3$ | $CH_2CO_2Pr$-n |
| $CF_3$ | $CH_2CO_2Pr$-iso |
| $CF_3$ | $CH_2CO_2Bu$-n |
| $CF_3$ | $CHMeCO_2Pr$-n |
| $CF_3$ | $CH_2CH_2CH_2CO_2Me$ |
| $CF_3$ | $CH_2COEt$ |
| $CF_3$ | $CH_2COPr$-n |
| $CF_3$ | $CH_2COPr$-iso |
| $CF_3$ | $CH_2COBu$-n |
| $CF_3$ | $CHMeCOMe$ |
| $CF_3$ | $CHMeCOEt$ |
| $CF_3$ | $CHMeCOPr$-n |
| $CF_3$ | $CH_2CH_2CH_2COMe$ |

TABLE 3

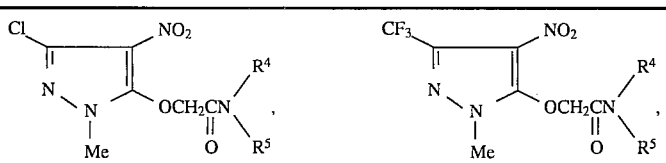

TABLE 3-continued
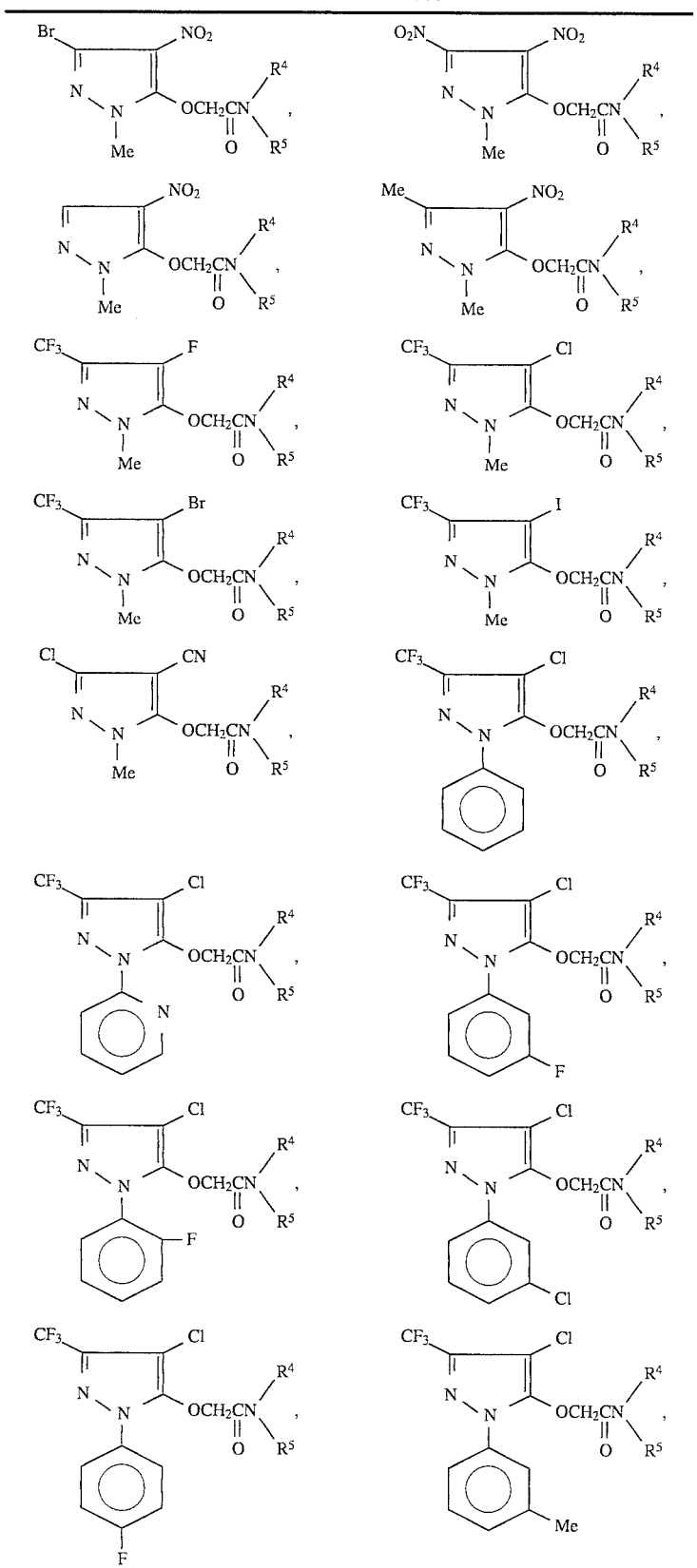

TABLE 3-continued

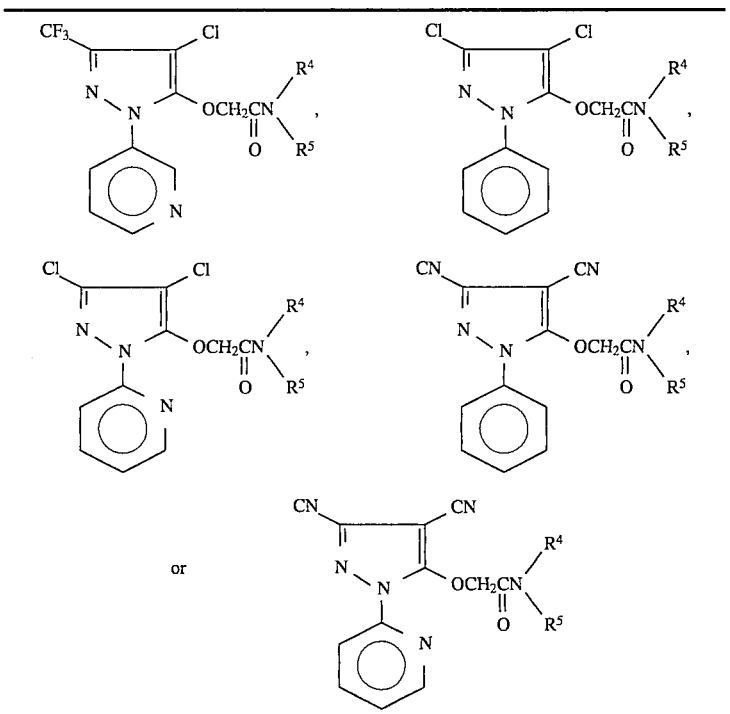

| R⁴ | R⁵ |
|---|---|
| Et | Ph |
| Pr-n | Ph |
| Pr-iso | Ph |
| Bu-n | Ph |
| Bu-iso | Ph |
| Bu-sec | Ph |
| Bu-tert | Ph |
| Pen-n | Ph |
| Hex-n | Ph |
| Hex-iso | Ph |
| Pr-cyc | Ph |
| Bu-cyc | Ph |
| Pen-cyc | Ph |
| Hex-cyc | Ph |
| CH₂Pr-cyc | Ph |
| CH₂Bu-cyc | Ph |
| CH₂Pen-cyc | Ph |
| CH₂Hex-cyc | Ph |
| CH₂CH₂Pr-cyc | Ph |
| CH₂CH=CH₂ | Ph |
| CH₂CH=CHMe | Ph |
| CH₂CH₂CH=CH₂ | Ph |
| CH₂C≡CH | Ph |
| CH₂C≡CMe | Ph |
| OMe | Ph |
| OEt | Ph |
| OPr-n | Ph |
| OPr-iso | Ph |
| OBu-n | Ph |
| OBu-iso | Ph |
| OBu-tert | Ph |
| SO₂Me | Ph |
| SO₂Et | Ph |
| SO₂Pr-n | Ph |
| SO₂Pr-iso | Ph |
| SO₂Bu-n | Ph |
| CH₂OMe | Ph |
| CH₂OEt | Ph |
| CH₂OPr-n | Ph |
| CH₂OBu-n | Ph |
| CH₂OBu-iso | Ph |
| CH₂OBu-sec | Ph |

TABLE 3-continued

| | |
|---|---|
| CH$_2$OBu-tert | Ph |
| CH$_2$CH$_2$OMe | Ph |
| CH$_2$CH$_2$OEt | Ph |
| CH$_2$CH$_2$OPr-n | Ph |
| CH$_2$CH$_2$CH$_2$OMe | Ph |
| CH$_2$CH$_2$CH$_2$OEt | Ph |
| CH$_2$CH$_2$CH$_2$CH$_2$OMe | Ph |
| CH$_2$CH$_2$OMe | CH$_2$CH$_2$OMe |
| Me | 3-Cl—Ph |
| Me | 4-Cl—Ph |
| Me | 2,4-Cl$_2$—Ph |
| Me | 3,5-Cl$_2$—Ph |
| Me | 2,3-Cl$_2$—Ph |
| Me | 2,5-Cl$_2$—Ph |
| Me | 3-F—Ph |
| Me | 4-F—Ph |
| Me | 2-F-4-Cl |
| Me | 2-Br—Ph |
| Me | 3-Br—Ph |
| Me | 4-Br—Ph |
| Me | 3-Me—Ph |
| Me | 4-Me—Ph |
| Me | 2,4-Me$_2$—Ph |
| Me | 3,5-Me$_2$—Ph |
| Me | 2,6-Me$_2$—Ph |
| Me | 2,3-Me$_2$—Ph |
| Me | 2,5-Me$_2$—Ph |
| Me | 2-MeO—Ph |
| Me | 3-MeO—Ph |
| Me | 4-MeO—Ph |
| Me | 2-CF$_3$—Ph |
| Me | 3-CF$_3$—Ph |
| Me | 4-CF$_3$—Ph |
| Me | CH$_2$Ph |
| Et | Et |
| Pr-n | Pr-n |
| Pr-iso | Pr-iso |
| Bu-n | Bu-n |
| H | Ph |
| Me | OMe |
| Me | OEt |
| Me | OBu-n |
| Me | 2,4,6-Cl$_3$—Ph |
| Me | 2,3,5-Cl$_3$—Ph |
| Me | 2,3,4-Cl$_3$—Ph |
| Me | 2-NO$_2$—Ph |
| Me | 2-CN—Ph |
| Me | Me |
| Me | Et |
| Me | Pr-iso |
| Me | Bu-iso |
| Me | Bu-sec |
| Et | Pr-n |
| Et | Pr-iso |
| Et | Bu-n |
| Et | Bu-iso |
| Et | Bu-sec |
| Pr-n | Pr-iso |
| Pr-n | Bu-n |
| Pr-n | Bu-iso |
| Pr-n | Bu-sec |
| Bu-n | Bu-iso |
| Bu-n | Bu-sec |
| Bu-iso | Bu-iso |
| Bu-iso | Bu-sec |
| Bu-sec | Bu-sec |
| OMe | CH$_2$CH=CH$_2$ |
| OMe | CH$_2$CH≡CH |
| OEt | CH$_2$CH=CH$_2$ |
| OEt | CH$_2$CH≡CH |
| Me | H |
| Me | Bu-tert |
| Me | Hex-iso |
| Me | Pr-cyc |
| Me | Bu-cyc |
| Me | CHMeCHMe$_2$ |
| Me | Pen-cyc |

TABLE 3-continued

| | |
|---|---|
| Me | Hex-cyc |
| Me | CH$_2$Pr-cyc |
| Me | CH$_2$Bu-cyc |
| Me | CH$_2$Pen-cyc |
| Me | CH$_2$Hex-cyc |
| Me | CH$_2$CH$_2$Pr-cyc |
| Me | CH$_2$CH=CHMe |
| Me | CH$_2$CH$_2$CH=CH$_2$ |
| Me | CH$_2$C≡CMe |
| Me | CH$_2$OMe |
| Me | CH$_2$OEt |
| Me | CH$_2$OPr-n |
| Me | CH$_2$OBu-n |
| Me | CH$_2$OBu-iso |
| Me | CH$_2$OBu-sec |
| Me | CH$_2$OBu-tert |
| Me | CH$_2$CH$_2$OMe |
| Me | CH$_2$CH$_2$OEt |
| Me | CH$_2$CH$_2$OPr-n |
| Me | CH$_2$CH$_2$CH$_2$OMe |
| Me | CH$_2$CH$_2$CH$_2$OEt |
| Me | CH$_2$CH$_2$CH$_2$CH$_2$OMe |
| Me | OPr-n |
| Me | OPr-iso |
| Me | OBu-iso |
| Me | OBu-tert |
| Me | SO$_2$Me |
| Me | SO$_2$Et |
| Me | SO$_2$Pr-n |
| Me | SO$_2$Pr-iso |
| Me | SO$_2$Bu-n |
| Me | COMe |
| Me | COEt |
| Me | COPr-n |
| Me | COPr-iso |
| Me | COBu-n |
| Me | CO$_2$Me |
| Me | CO$_2$Et |
| Me | CO$_2$Pr-n |
| Me | CO$_2$Pr-iso |
| Me | CO$_2$Bu-n |
| Me | CH$_2$CO$_2$Me |
| Me | CH$_2$CO$_2$Et |
| Me | CH$_2$CO$_2$Pr-n |
| Me | CH$_2$CO$_2$Bu-n |
| Me | CHMeCO$_2$Me |
| Me | CHMeCO$_2$Et |
| Me | CH$_2$CH$_2$CO$_2$Me |
| Me | CH$_2$CH$_2$CH$_2$CO$_2$Me |
| Me | CH$_2$CH$_2$CH$_2$CH$_2$CO$_2$Me |
| Me | CH(Pr-iso)CO$_2$Me |
| Me | CH(Bu-sec)CO$_2$Me |
| Me | CH(Bu-iso)CO$_2$Me |
| Me | CH(CH$_2$Ph)CO$_2$Me |
| Me | CH$_2$CH$_2$CN |
| Me | 1-Naph |
| Me | 2-Naph |
| Me | CH$_2$-1-Naph |
| Me | CH$_2$-2-Naph |
| Me | CH$_2$Ph |
| Me | CHMePh |
| Me | CMe$_2$Ph |
| Me | CH$_2$-2-Cl—Ph |
| Me | CH$_2$-3-Cl—Ph |
| Me | CH$_2$-4-Cl—Ph |
| Me | 2-Py |
| Me | 6-MeO-2-Py |
| Me | 3-MeO-2-Py |
| Me | 6-Cl-2-Py |
| Me | 6-F-2-Py |
| Me | 5-CF$_3$-2-Py |
| Me | 3-Cl-5-CF$_3$-2-Py |
| Me | 3-Py |
| Me | 4-Py |
| Me | CH$_2$-5-Cl-2-Py |
| Me | CH$_2$-6-Cl-3-Py |
| H | H |
| H | Et |

TABLE 3-continued

| | |
|---|---|
| H | Pr-n |
| H | Pr-iso |
| H | Bu-n |
| H | Bu-iso |
| H | Bu-sec |
| H | Bu-tert |
| H | CHMeCHMe$_2$ |
| H | Pen-n |
| H | Hex-n |
| H | Hex-iso |
| H | Pr-cyc |
| H | Bu-cyc |
| H | Pen-cyc |
| H | Hex-cyc |
| H | CH$_2$Pr-cyc |
| H | CH$_2$Bu-cyc |
| H | CH$_2$Pen-cyc |
| H | CH$_2$Hex-cyc |
| H | CH$_2$CH$_2$Pr-cyc |
| H | CH$_2$CH=CH$_2$ |
| H | CH$_2$CH=CHMe |
| H | CH$_2$CH$_2$CH=CH$_2$ |
| H | CH$_2$C≡CH |
| H | CH$_2$C≡CMe |
| H | CH$_2$OMe |
| H | CH$_2$OEt |
| H | CH$_2$OPr-n |
| H | CH$_2$OBu-n |
| H | CH$_2$OBu-iso |
| H | CH$_2$OBu-sec |
| H | CH$_2$OBu-tert |
| H | CH$_2$CH$_2$OMe |
| H | CH$_2$CH$_2$OEt |
| H | CH$_2$CH$_2$OPr-n |
| H | CH$_2$CH$_2$CH$_2$OMe |
| H | CH$_2$CH$_2$CH$_2$OEt |
| H | CH$_2$CH$_2$CH$_2$CH$_2$OMe |
| H | 2-Cl—Ph |
| H | 3-Cl—Ph |
| H | 4-Cl—Ph |
| H | 2,4-Cl$_2$—Ph |
| H | 3,5-Cl$_2$—Ph |
| H | 2,6-Cl$_2$—Ph |
| H | 2,3-Cl$_2$—Ph |
| H | 2,5-Cl$_2$—Ph |
| H | 2-F—Ph |
| H | 3-F—Ph |
| H | 4-F—Ph |
| H | 2-F-4-Cl—Ph |
| H | 2-Br—Ph |
| H | 3-Br—Ph |
| H | 4-Br—Ph |
| H | 2-Me—Ph |
| H | 3-Me—Ph |
| H | 4-Me—Ph |
| H | 2,4-Me$_2$—Ph |
| H | 3,5-Me$_2$—Ph |
| H | 2,6-Me$_2$—Ph |
| H | 2,3-Me$_2$—Ph |
| H | 2,5-Me$_2$—Ph |
| H | 2-MeO—Ph |
| H | 3-MeO—Ph |
| H | 4-MeO—Ph |
| H | 2-CF$_3$—Ph |
| H | 3-CF$_3$—Ph |
| H | 4-CF$_3$—Ph |
| H | 2,4,6-Cl$_3$—Ph |
| H | 2,3,5-Cl$_3$—Ph |
| H | 2,3,4-Cl$_3$—Ph |
| H | 2-NO$_2$—Ph |
| H | 2-CN—Ph |
| H | CH$_2$Ph |
| H | OMe |
| H | OEt |
| H | OPr-n |
| H | OPr-iso |
| H | OBu-n |

TABLE 3-continued

| | |
|---|---|
| H | OBu-iso |
| H | OBu-tert |
| H | SO$_2$Me |
| H | SO$_2$Et |
| H | SO$_2$Pr-n |
| H | SO$_2$Pr-iso |
| H | SO$_2$Bu-n |
| H | COMe |
| H | COEt |
| H | COPr-n |
| H | COPr-iso |
| H | COBu-n |
| H | CO$_2$Me |
| H | CO$_2$Et |
| H | CO$_2$Pr-n |
| H | CO$_2$Pr-iso |
| H | CO$_2$Bu-n |
| H | CH$_2$CO$_2$Me |
| H | CH$_2$CO$_2$Et |
| H | CH$_2$CO$_2$Pr-n |
| H | CH$_2$CO$_2$Bu-n |
| H | CHMeCO$_2$Me |
| H | CHMeCO$_2$Et |
| H | CH$_2$CH$_2$CO$_2$Me |
| H | CH$_2$CH$_2$CH$_2$CO$_2$Me |
| H | CH$_2$CH$_2$CH$_2$CH$_2$CO$_2$Me |
| H | CH(Pr-iso)CO$_2$Me |
| H | CH(Bu-sec)CO$_2$Me |
| H | CH(Bu-iso)CO$_2$Me |
| H | CH(CH$_2$Ph)CO$_2$Me |
| H | CH$_2$CH$_2$CN |
| H | 1-Naph |
| H | 2-Naph |
| H | CH$_2$-1-Naph |
| H | CH$_2$-2-Naph |
| H | CH$_2$Ph |
| H | CHMePh |
| H | CMe$_2$Ph |
| H | CH$_2$-2-Cl—Ph |
| H | CH$_2$-3-Cl—Ph |
| H | CH$_2$-4-Cl—Ph |
| H | 2-Py |
| H | 6-MeO-2-Py |
| H | 3-MeO-2-Py |
| H | 6-Cl-2-Py |
| H | 6-F-2-Py |
| H | 5-CF$_3$-2-Py |
| H | 3-Cl-5-CF$_3$-2-Py |
| H | 3-Py |
| H | 4-Py |
| H | CH$_2$-5-Cl-2-Py |
| H | CH$_2$-6-Cl-3-Py |

TABLE 4

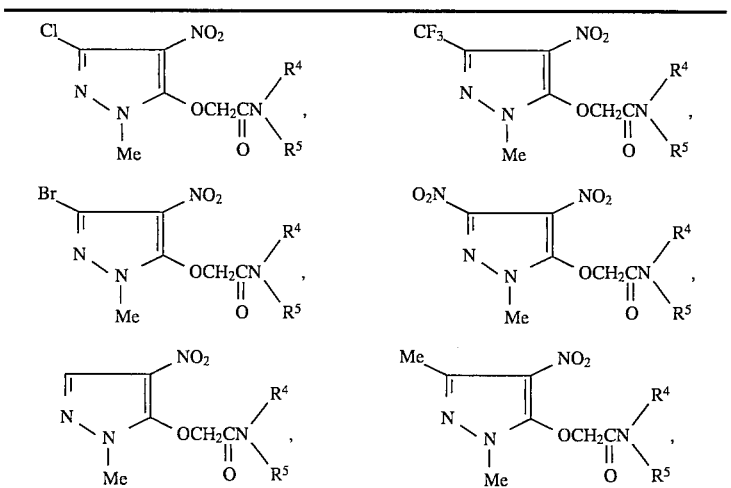

TABLE 4-continued
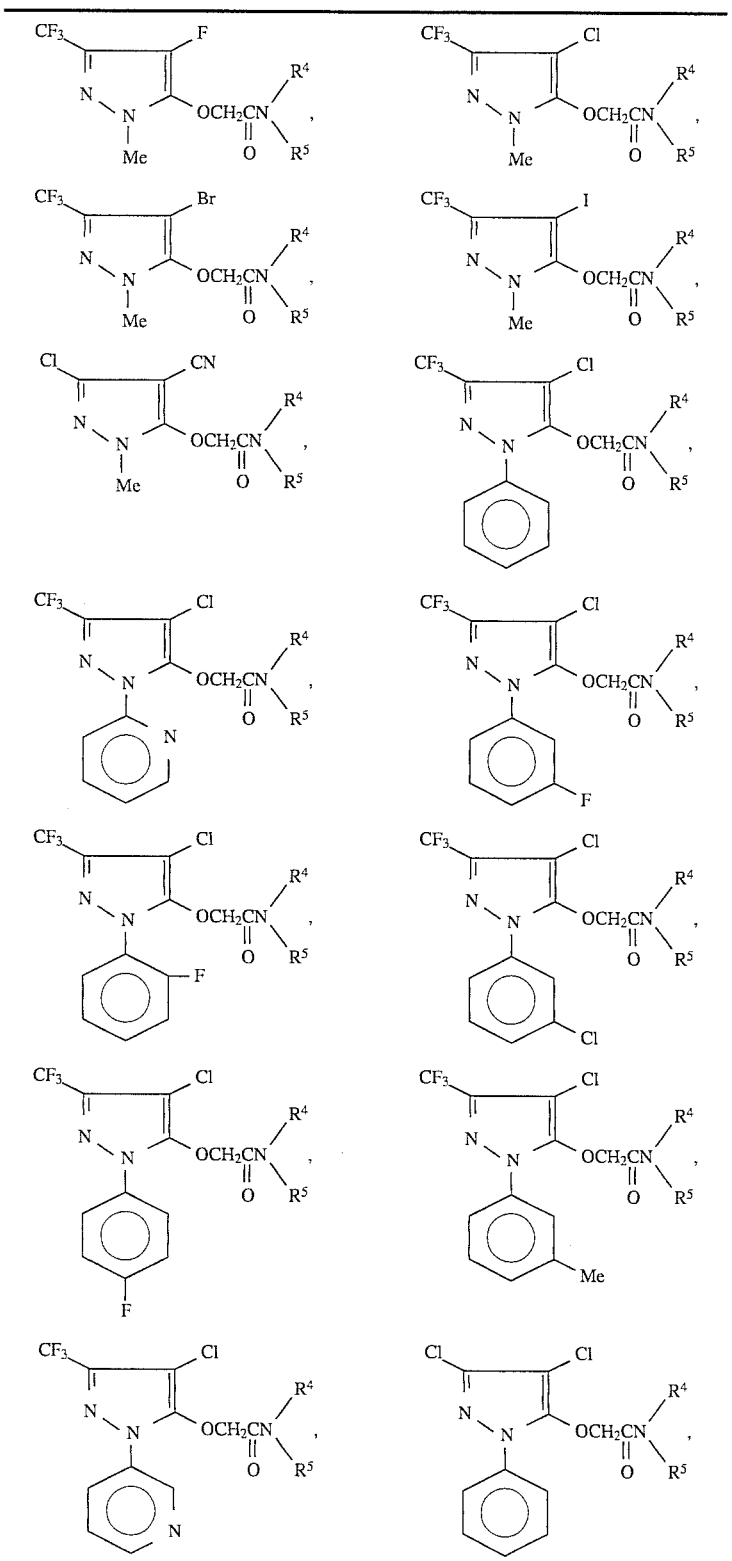

TABLE 4-continued

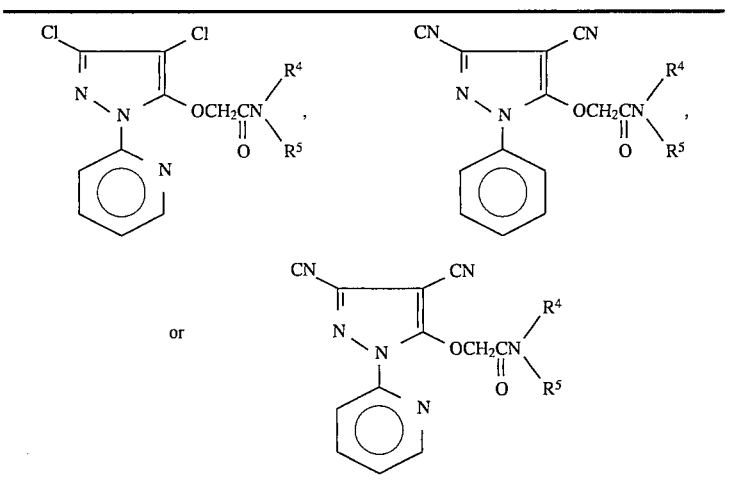

In Table 4, $NR^4R^5$ represents:

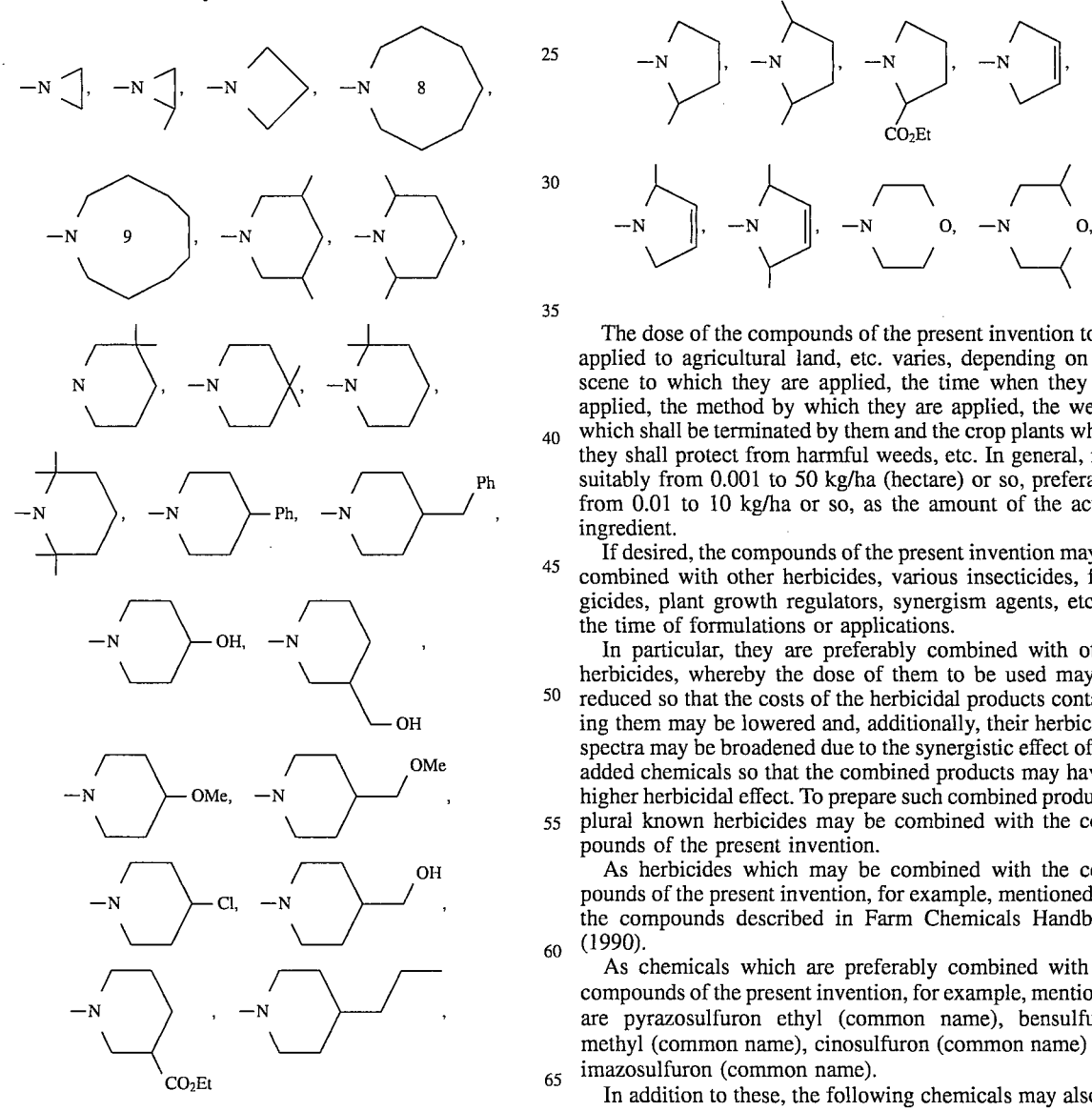

The dose of the compounds of the present invention to be applied to agricultural land, etc. varies, depending on the scene to which they are applied, the time when they are applied, the method by which they are applied, the weeds which shall be terminated by them and the crop plants which they shall protect from harmful weeds, etc. In general, it is suitably from 0.001 to 50 kg/ha (hectare) or so, preferably from 0.01 to 10 kg/ha or so, as the amount of the active ingredient.

If desired, the compounds of the present invention may be combined with other herbicides, various insecticides, fungicides, plant growth regulators, synergism agents, etc. at the time of formulations or applications.

In particular, they are preferably combined with other herbicides, whereby the dose of them to be used may be reduced so that the costs of the herbicidal products containing them may be lowered and, additionally, their herbicidal spectra may be broadened due to the synergistic effect of the added chemicals so that the combined products may have a higher herbicidal effect. To prepare such combined products, plural known herbicides may be combined with the compounds of the present invention.

As herbicides which may be combined with the compounds of the present invention, for example, mentioned are the compounds described in Farm Chemicals Handbook (1990).

As chemicals which are preferably combined with the compounds of the present invention, for example, mentioned are pyrazosulfuron ethyl (common name), bensulfuron methyl (common name), cinosulfuron (common name) and imazosulfuron (common name).

In addition to these, the following chemicals may also be combined with the compounds of the present invention:

Pretilachlor (common name), esprocarb (common name), pyrazolate (common name), pyrazoxyfen (common name), benzofenap (common name), dymron (common name), bromobutide (common name), naproanilide (common name), clomeprop (common name), CNP (common name), chlomethoxynil (common name), bifenox (common name), oxadiazon (common name), mefenacet (common name), butachlor (common name), butenachlor (common name), dithiopyr (common name), benfuresate (common name), pyributicarb (common name), benthiocarb (common name), dimepiperate (common name), molinate (common name), butamifos (common name), quinclorac (common name), cinmethylin (common name), simetryn (common name), SAP (bensulide - common name), dimethametryn (common name), MCPA, MCPB, 2',3'-dichloro- 4-ethoxymethoxybenzanilide (HW-52 as test name), 1-( 2-chlorobenzyl)-3-($\alpha,\alpha$-dimethylbenzyl)urea (JC-940 as test name), N-[2'-(3'-methoxy)-thienylmethyl]-N-chloroacetyl- 2,6-dimethylanilide (NSK-850 as test name), etc.

Where the compounds of the present invention are used as herbicide, in general, they may be mixed with pertinent carriers, for example, solid carriers such as clay, talc, bentonite, diatomaceous earth, white carbon, etc. or liquid carriers such as water, alcohols (e.g., isopropanol, butanol, benzyl alcohol, furfuryl-alcohol, etc.), aromatic hydrocarbons (e.g., toluene, xylene, etc.), ethers (e.g., anisole, etc.), ketones (e.g., cyclohexanone, isophorone, etc.), esters (e.g., butyl acetate, etc.), acid amides (e.g., N-methylpyrrolidone, etc.) or halogenated hydrocarbons (e.g., chlorobenzene, etc.). If desired, they may be prepared into various practical formulations, including liquid formulation, emulsifiable concentrate, wettable powder, dry flowable powder, flowable liquid, dust, granule, etc., optionally along with surfactant, emulsifier, dispersing agent, penetration promoter, adhesion promoter, tackifier, anti-freezing agent, anti-caking agent, stabilizer, etc.

Where the compounds of the present invention are formulated into herbicidal granules to be applied to paddy fields, for example, usable are kaolinite, montmorillonite, diatomaceous earth, bentonite, talc, clay, calcium carbonate, calcium sulfate, ammonium sulfate, etc., as the solid carriers, and alkylbenzenesulfonates, polyoxyethylene alkylaryl ethers, ligninesulfonates, alkylsulfosuccinates, polyoxyethylene fatty acid esters, naphthalenesulfonates, polyoxyethylene alkylaryl ether sulfates, alkylamine salts, tripolyphosphates, etc., as the surfactants. The content of these surfactants in the herbicidal granules is not specifically defined but is, in general, desirably within the range of from 0.05 to 20 parts by weight relative to 100 parts by weight of the granules. If desired, the granules may contain a decomposition inhibitor such as epoxidated soybean oil, etc.

Next, examples of formulations of herbicidal products containing the compounds of the present invention are mentioned below, which, however, are not limitative. In the following examples, all "parts" are by weight.

| Wettable Powder: | |
| --- | --- |
| Compound of this invention | 5 to 80 pts. |
| Solid carrier | 10 to 85 pts. |
| Surfactant | 1 to 10 pts. |
| Others | 1 to 5 pts. |

As others, for example, mentioned are anti-caking agent, etc.

| Emulsifiable concentrate: | |
| --- | --- |
| Compound of this invention | 1 to 30 pts. |
| Liquid carrier | 30 to 95 pts. |
| Surfactant | 5 to 15 pts. |
| Flowable Liquid: | |
| Compound of this invention | 5 to 70 pts. |
| Liquid Carrier | 15 to 65 pts. |
| Surfactant | 5 to 12 pts. |
| Others | 5 to 30 pts. |

As others, for example, mentioned are anti-freezing agent, tackifier, etc.

| Granular Wettable Powder (dry flowable powder): | |
| --- | --- |
| Compound of this invention | 20 to 90 pts. |
| Solid Carrier | 10 to 60 pts. |
| Surfactant | 1 to 20 pts. |
| Granules: | |
| Compound of this invention | 0.1 to 10 pts. |
| Solid carrier | 90 to 99.9 pts. |
| Others | 1 to 5 pts. |

| Formulation Example 1: Wettable Powder | |
| --- | --- |
| Compound No. 1 of this invention | 20 pts. |
| Zeeklite A | 76 pts. |
| (kaolin clay, trade name by Zeeklite Co.) | |
| Sorpol 5039 | 2 pts. |
| (mixture of nonionic surfactant and anionic surfactant, trade name by Toho Chemical Co.) | |
| Carplex (anti-caking agent) | 2 pts. |
| (white carbon, trade name by Shionogi Pharmaceutical Co.) | |

The above-mentioned components were homogeneously blended and powdered to give a wettable powder.

| Formulation Example 2: Wettable Powder | |
| --- | --- |
| Compound No. 1 of this invention | 40 pts. |
| Zeeklite A | 54 pts. |
| (kaolin clay, trade name by Zeeklite Co.) | |
| Sorpol 5039 | 2 pts. |
| (mixture of nonionic surfactant and anionic surfactant, trade name by Toho Chemical Co.) | |
| Carplex (anti-caking agent) | 4 pts. |
| (white carbon, trade name by Shionogi Pharmaceutical Co.) | |

The above-mentioned components were homogeneously blended and powdered to give a wettable powder.

| Formulation Example 3: Emulsifiable concentrate | |
| --- | --- |
| Compound No. 1 of this invention | 5 pts. |
| Xylene | 75 pts. |
| Dimethylformamide | 15 pts. |
| Sorpol 2680 | 5 pts. |
| (mixture of nonionic surfactant and anionic surfactant, trade name by Toho Chemical Co.) | |

The above-mentioned components were homogeneously blended to give an emulsion.

| Formulation Example 4: Flowable Liquid | |
|---|---|
| Compound No. 1 of this invention | 25 pts. |
| Agrisole S-710 | 10 pts. |
| (nonionic surfactant, trade name by Kaoh Co.) | |
| Runox 1000C | 0.5 pts. |
| (anionic surfactant, trade name by Toho Chemical Co.) | |
| Aqueous 1% Rodopol water | 20 pts. |
| (tackifier, trade name by Rhone-Poulenc Co.) | |
| Water | 44.5 pts. |

The above-mentioned components were homogeneously blended to give a flowable liquid.

| Formulation Example 5: Flowable Liquid | |
|---|---|
| Compound No. 1 of this invention | 40 pts. |
| Agrisole S-710 | 10 pts. |
| (nonionic surfactant, trade name by Kaoh Co.) | |
| Runox 1000C | 0.5 pts. |
| (anionic surfactant, trade name by Toho Chemical Co.) | |
| Aqueous 1% Rodopol water | 20 pts. |
| (tackifier, trade name by Rhone-Poulenc Co.) | |
| Water | 29.5 pts. |

The above-mentioned components were homogeneously blended to give a flowable liquid.

| Formulation Example 6: Granular Wettable Powder (dry flowable powder) | |
|---|---|
| Compound No. 1 of this invention | 75 pts. |
| Isobam No. 1 | 10 pts. |
| (anionic surfactant, trade name by Kuraray Isoprene Chemical Co.) | |
| Vanilex N | 5 pts. |
| (anionic surfactant, trade name by Sanyo Kokusaku Pulp Co.) | |
| Carplex #80 | 10 pts. |
| (white carbon, trade name by Shionogi Pharmaceutical Co.) | |

The above-mentioned components were homogeneously blended and finely powdered to give a dry flowable powder.

| Formulation Example 7: Granule | |
|---|---|
| Compound No. 1 of this invention | 1 pts. |
| Bentonite | 55 pts. |
| Talc | 44 pts. |

The above-mentioned components were blended and powdered, and a small amount of water was added thereto, stirred, further blended and kneaded. Using an granulator, the mixture was granulated and dried to give granules.

| Formulation Example 8: Granule | |
|---|---|
| Compound No. 1 of this invention | 1.0 pts. |
| Compound (A) | 0.07 pts. |
| DBSN | 3 pts. |
| Epoxidated Soybean Oil | 1 pts. |
| Bentonite | 30 pts. |
| Talc | 64.93 pts. |

The above-mentioned components were blended and powdered, and a small amount of water was added thereto and kneaded. Using an extrusion granulator, the mixture was granulated and dried to give granules.

Compound (A) is pyrazosulfuron ethyl (common name); and DBSN is sodium dodecylbenzenesulfonate.

Where the above-mentioned wettable powder, emulsion, flowable liquid and granular wettable powder are actually used, they are diluted with water to 1/50 to 1/1000 dilutions, and the dilution may be applied in a dose of from 0.001 to 50 kg/ha, preferably from 0.01 to 10 kg/ha, as the active ingredient.

The herbicides containing the compounds of the present invention may be applied to paddy fields both for soil treatment and for foliage treatment.

As examples of paddy weeds, mentioned are weeds of the family Alismataceae such as *Alisma canaliculatum, Sagittaria trifolia, Sagittaria pygmaea*, etc.; weeds of the family Cyperaceae such as *Cyperus difformis, Cyperus serotinus, Scirpus juncoides, Eleocharis kuroguwai*, etc.; weeds of the family Scrothulariaceae such as *Lindemia pyxidaria*, etc.; weeds of the family Potenderiaceae such as *Monochoria vaginalis*, etc.; weeds of the family Potamogetonaceae such as *Potamogeton distinctus*, etc.; weeds of the family Lythraceae such as *Rotala indica*, etc.; and weeds of the family Gramineae such as *Echinochloa crus-galli*, etc.

The compounds of the present invention are also usable as herbicides for soil treatment, soil incorporation treatment and foliage treatment. Furthermore, they may also be applied to control various weeds in non-agricultural fields, such as playgrounds, vacant lands, railroad sides, etc., in addition to agricultural and horticultural fields such as paddy fields, upland fields, orchards, etc.

The following test examples concretely demonstrate the usefulness of the compounds of the present invention as herbicides.

Test Example 1:

Test of compounds of the invention as to their herbicidal effect, by soil treatment under paddy field condition:

An Alluvium soil was put in 1/5000 are-Wagner pots, and water was added thereto to knead the soil therein. Accordingly, a paddy field condition was prepared, having a depth of water of 4 cm. Seeds of *Echinochloa crus-galli, Monochoria vaginalis, Rotala indica* and *Scirpus juncoides* were sown mixedly in the pots, and 2.5 leaves-stage rice plants were transplanted therein. The pots were put in a greenhouse at 25° to 30° C. so as to grow the plants. On the first day after the seeding, pre-determined doses of the compounds of the present invention, that had been prepared into herbicidal formulations in accordance with the formulation examples mentioned above, were applied on the water surfaces in the pots. Three weeks after the application, the herbicidal effect of the test compounds against the rice plants and the weeds was checked. The effect was evaluated by 5-rank evaluation, in which "0" means that the compound had no influence on the plants while "5" means that the plants were completely withered. The test results are shown in Table 5 below.

Test Example 2:

Test of compounds of the invention as to their herbicidal effect, by foliage treatment under paddy field condition.

An Alluvium soil was put in 1/5000 are-Wagner pots, and water was added thereto to knead the soil therein. Accordingly, a paddy field condition was prepared, having a depth of water of 4 cm. Seeds of *Echinochloa crus-galli, Monochoria vaginalis, Rotala indica* and *Scirpus juncoides* were sown mixedly in the pots, and 2.5 leaves-stage rice plants were transplanted therein. The pots were put in a greenhouse at 25° to 30° C. so as to grow the plants. After the weeds of Echinochloa crus-galli, Monochoria vaginalis, Rotala indica and Scirpus juncoides had grown to one leaf- to two leaves-stage and the rice plants to four leaves-stage, predetermined amount of the compounds of the present invention, that had been prepared into herbicidal formulations in accordance with the formulation examples mentioned above, were applied over the plants in the pots. Three weeks after the application, the herbicidal effect of the test compounds against the rice plants and the weeds was checked. The effect was evaluated in the same manner as in Test Example 1. The test results are shown in Table 6 below.

In the following tables, A means *Echinochloa crus-galli;* B means *Scirpus juncoides,* C means *Monochoria vaginalis,* D means *Rotala indica,* and a means rice plants.

TABLE 5

| Compound No. | Amount of Compound g/a | A | B | C | D | a |
|---|---|---|---|---|---|---|
| 1 | 10 | 5 | 5 | 5 | 5 | 0 |
| 2 | 10 | 5 | 5 | 5 | 4 | 0 |
| 3 | 10 | 5 | 5 | 5 | 5 | 0 |
| 4 | 10 | 5 | 5 | 5 | 5 | 0 |
| 5 | 10 | 5 | 5 | 5 | 5 | 0 |
| 7 | 10 | 5 | 5 | 5 | 4 | 0 |
| 8 | 10 | 5 | 5 | 4 | 2 | 0 |
| 9 | 10 | 5 | 5 | 5 | 4 | 0 |
| 10 | 10 | 5 | 4 | 5 | 2 | 0 |
| 11 | 10 | 5 | 4 | 5 | 5 | 0 |
| 12 | 10 | 5 | 2 | 5 | 4 | 0 |
| 13 | 10 | 5 | 4 | 5 | 4 | 0 |
| 14 | 10 | 5 | 4 | 5 | 4 | 0 |
| 16 | 10 | 5 | 5 | 5 | 4 | 0 |
| 18 | 10 | 5 | 4 | 4 | 4 | 0 |
| 19 | 10 | 5 | 4 | 4 | 4 | 0 |
| 22 | 10 | 5 | 5 | 5 | 5 | 0 |
| 25 | 10 | 5 | 5 | 5 | 5 | 0 |
| 26 | 10 | 5 | 5 | 5 | 5 | 0 |
| 27 | 10 | 5 | 5 | 5 | 5 | 0 |
| 33 | 10 | 5 | 5 | 5 | 5 | 0 |
| 34 | 10 | 5 | 5 | 5 | 5 | 0 |
| 37 | 10 | 5 | 5 | 4 | 4 | 0 |
| 38 | 10 | 5 | 5 | 4 | 4 | 0 |
| 39 | 10 | 5 | 5 | 5 | 5 | 0 |
| 40 | 10 | 5 | 5 | 4 | 4 | 0 |
| 44 | 10 | 5 | 5 | 4 | 5 | 0 |
| 45 | 10 | 5 | 5 | 5 | 4 | 0 |
| 50 | 10 | 5 | 5 | 4 | 4 | 0 |
| 55 | 10 | 5 | 5 | 4 | 4 | 0 |
| 57 | 10 | 5 | 5 | 4 | 5 | 0 |
| 58 | 10 | 5 | 5 | 5 | 5 | 0 |
| 59 | 10 | 5 | 5 | 5 | 5 | 0 |
| 60 | 10 | 5 | 5 | 5 | 5 | 0 |
| 61 | 10 | 5 | 5 | 4 | 4 | 0 |
| 62 | 10 | 5 | 5 | 5 | 4 | 0 |
| 63 | 10 | 5 | 5 | 5 | 4 | 0 |
| 64 | 10 | 5 | 5 | 5 | 4 | 0 |
| 65 | 10 | 5 | 5 | 5 | 4 | 0 |
| 66 | 10 | 5 | 5 | 5 | 4 | 0 |
| 67 | 10 | 5 | 5 | 5 | 5 | 0 |
| 87 | 10 | 5 | 5 | 5 | 5 | 0 |
| 88 | 10 | 5 | 5 | 5 | 5 | 0 |
| 92 | 10 | 5 | 5 | 5 | 5 | 0 |
| 95 | 10 | 5 | 5 | 4 | 4 | 0 |
| 97 | 10 | 5 | 5 | 5 | 5 | 0 |
| 98 | 10 | 5 | 5 | 5 | 5 | 0 |
| 99 | 10 | 5 | 5 | 5 | 5 | 0 |
| 100 | 10 | 5 | 5 | 5 | 5 | 0 |
| 101 | 10 | 5 | 5 | 5 | 5 | 0 |
| 104 | 10 | 5 | 5 | 5 | 4 | 0 |
| 105 | 10 | 5 | 5 | 5 | 4 | 0 |
| 106 | 10 | 5 | 5 | 5 | 4 | 0 |
| 107 | 10 | 5 | 5 | 5 | 4 | 0 |
| 108 | 10 | 5 | 5 | 5 | 5 | 0 |
| 116 | 10 | 5 | 5 | 5 | 4 | 0 |
| 124 | 10 | 5 | 5 | 5 | 5 | 0 |
| 125 | 10 | 5 | 5 | 5 | 5 | 0 |
| 127 | 10 | 5 | 5 | 5 | 5 | 0 |
| 128 | 10 | 5 | 5 | 4 | 4 | 0 |
| 133 | 10 | 5 | 5 | 5 | 5 | 0 |
| 136 | 10 | 5 | 5 | 5 | 5 | 0 |
| 138 | 10 | 5 | 5 | 5 | 4 | 0 |
| 146 | 10 | 5 | 5 | 5 | 5 | 0 |
| 149 | 10 | 5 | 5 | 5 | 5 | 0 |
| 170 | 10 | 5 | 5 | 5 | 4 | 0 |
| 171 | 10 | 5 | 5 | 5 | 4 | 0 |
| 173 | 10 | 5 | 5 | 5 | 5 | 0 |
| 174 | 10 | 5 | 5 | 5 | 4 | 0 |

TABLE 6

| Compound No. | Amount of Compound g/a | A | B | C | D | a |
|---|---|---|---|---|---|---|
| 4 | 10 | 5 | 4 | 4 | 3 | 0 |
| 34 | 10 | 5 | 4 | 4 | 4 | 0 |
| 38 | 10 | 5 | 4 | 3 | 4 | 0 |
| 59 | 10 | 5 | 4 | 4 | 2 | 0 |
| 63 | 10 | 5 | 4 | 4 | 4 | 0 |
| 65 | 10 | 5 | 5 | 4 | 4 | 0 |
| 66 | 10 | 5 | 5 | 4 | 4 | 0 |
| 88 | 10 | 5 | 5 | 4 | 4 | 0 |
| 92 | 10 | 5 | 4 | 4 | 4 | 0 |
| 98 | 10 | 5 | 4 | 5 | 5 | 0 |
| 99 | 10 | 5 | 4 | 5 | 4 | 0 |
| 100 | 10 | 5 | 4 | 5 | 4 | 0 |
| 101 | 10 | 5 | 5 | 5 | 4 | 0 |
| 105 | 10 | 5 | 4 | 4 | 4 | 0 |
| 107 | 10 | 5 | 4 | 4 | 4 | 0 |
| 108 | 10 | 5 | 4 | 4 | 4 | 0 |
| 125 | 10 | 5 | 4 | 5 | 4 | 0 |
| 128 | 10 | 5 | 4 | 4 | 4 | 0 |
| 134 | 10 | 5 | 4 | 4 | 4 | 0 |
| 136 | 10 | 5 | 5 | 5 | 4 | 0 |
| 138 | 10 | 5 | 4 | 4 | 4 | 0 |
| 146 | 10 | 5 | 5 | 5 | 5 | 0 |
| 149 | 10 | 5 | 5 | 5 | 5 | 0 |
| 173 | 10 | 5 | 5 | 5 | 5 | 0 |
| 174 | 10 | 5 | 4 | 5 | 3 | 0 |

We claim:

1. A pyrazole-glycolic acid amide of formula (1):

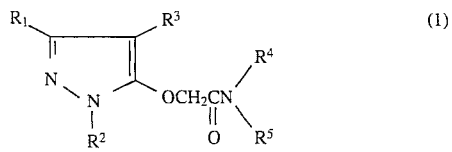

wherein

R$^1$ represents a C$_{1-4}$ haloalkyl group, a cyano group, or a halogen atom;

R$^2$ represents an unsubstituted phenyl group or an unsubstituted pyridyl group;

R$^3$ represents a halogen atom;

R$^4$ and R$^5$ form, along with the nitrogen atom to which they bond, a 5-membered to 8-membered ring, wherein the ring may contain one or more nitrogen atoms and the ring may be substituted by a C$_{1-4}$ alkyl group.

2. A herbicidal composition comprising one or more pyrazole-glycolic acid amide(s) as claimed in claim 1 as the active ingredient(s).

3. A method for controlling or inhibiting the growth of weeds by applying thereto a herbicidally effective amount of one or more pyrazole-glycolic acid amide(s) as claimed in claim 1.

* * * * *